United States Patent
Schroeder et al.

(10) Patent No.: US 7,270,730 B2
(45) Date of Patent: *Sep. 18, 2007

(54) HIGH-THROUGHPUT ELECTROPHYSIOLOGICAL MEASUREMENT SYSTEM

(75) Inventors: Kirk S. Schroeder, Ann Arbor, MI (US); Bradley D. Neagle, Ann Arbor, MI (US)

(73) Assignee: Essen Instruments, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/236,684

(22) Filed: Sep. 5, 2002

(65) Prior Publication Data

US 2003/0070923 A1   Apr. 17, 2003

Related U.S. Application Data

(63) Continuation-in-part of application No. PCT/US02/16122, filed on May 21, 2002, and a continuation-in-part of application No. 09/862,056, filed on May 21, 2001, now Pat. No. 7,067,046, and a continuation-in-part of application No. 09/631,909, filed on Aug. 4, 2000, now Pat. No. 6,488,829.

(60) Provisional application No. 60/383,196, filed on May 22, 2002, provisional application No. 60/317,112, filed on Sep. 6, 2001.

(51) Int. Cl.
*G01N 33/487* (2006.01)

(52) U.S. Cl. .................. 204/403.01; 435/287.1

(58) Field of Classification Search ......... 204/403.01; 435/287.1, 287.5, 817; 422/63, 65
See application file for complete search history.

(56) References Cited

U.S. PATENT DOCUMENTS 3,856,633 A   12/1974   Fletcher, III (Continued)

FOREIGN PATENT DOCUMENTS

AU   75770/91 V   2/1995

(Continued)

OTHER PUBLICATIONS

Kostyuk et al, Nature, vol. 257, pp. 691-693, 1975.*
Hamill et al, Pflugers Arch, vol. 391, pp. 85-100, 1981.☐☐.*
Rae et al, J. Neuroscience Methods, vol. 37, pp. 15-26, 1991.*
Haptotaxis and the Mechanism of Cell Motility, Carter, Nature, pp. 256-261, Jan. 21, 1967.

(Continued)

*Primary Examiner*—Kaj K. Olsen
(74) *Attorney, Agent, or Firm*—Morgan, Lewis & Bockius LLP; David J. Brezner; Victor E. Johnson

(57) ABSTRACT

Systems, including apparatus and methods, for performing electrophysiological measurements on membranous samples, including living cells, isolated cell fragments (such as organelles), and/or artificial membranes (such as vesicles). The apparatus may include a high-throughput electrophysiological measurement system, and components thereof. This measurement system may include, among others, (1) a fluidics head for transferring samples and/or other compounds to a perforated measurement substrate, (2) a pressure-regulated plenum system for positioning samples on the substrate and subsequently forming a high-resistance electrical seal, (3) an activation system (such as a computer-controlled pulsed UV illumination module) for activating caged compounds, (4) an electronics head for applying and/or measuring voltage and/or current, and/or (5) a computer-controlled analysis system for collecting and/or analyzing data. The methods may include methods for performing high-throughput electrophysiological measurements on transporters and/or voltage or ligand-gated ion channels, sequentially and/or simultaneously.

44 Claims, 27 Drawing Sheets

U.S. PATENT DOCUMENTS

| | | | |
|---|---|---|---|
| 4,055,799 A | 10/1977 | Coster et al. ............. 324/71 R |
| 4,062,750 A | 12/1977 | Butler |
| 4,071,315 A | 1/1978 | Chateau .................... 23/230 B |
| 4,128,456 A | 12/1978 | Lee et al. |
| 4,225,410 A | 9/1980 | Pace |
| 4,231,660 A | 11/1980 | Remy et al. |
| 4,441,507 A | 4/1984 | Steflin |
| 4,456,522 A | 6/1984 | Blackburn |
| 4,490,216 A | 12/1984 | McConnell |
| 4,510,442 A | 4/1985 | Neher |
| 4,661,321 A | 4/1987 | Byrd et al. |
| 4,661,451 A | 4/1987 | Hansen |
| 4,803,154 A | 2/1989 | Uo et al. |
| 4,894,343 A | 1/1990 | Tanaka et al. ............... 435/301 |
| 4,911,806 A | 3/1990 | Hofmann |
| 4,912,060 A | 3/1990 | Fein |
| 4,952,518 A | 8/1990 | Johnson et al. ............. 436/518 |
| 5,009,846 A | 4/1991 | Gavet et al. |
| 5,041,266 A | 8/1991 | Fox |
| 5,055,263 A * | 10/1991 | Meltzer ........................ 422/65 |
| 5,111,221 A | 5/1992 | Fare et al. |
| 5,164,319 A | 11/1992 | Hafeman et al. |
| 5,169,600 A | 12/1992 | Ishizaka et al. ................ 422/66 |
| 5,187,096 A * | 2/1993 | Giaever et al. .......... 435/287.1 |
| 5,204,239 A | 4/1993 | Gitler et al. |
| 5,225,374 A | 7/1993 | Fare et al. |
| 5,229,163 A | 7/1993 | Fox |
| 5,234,566 A | 8/1993 | Osman et al. |
| 5,262,128 A | 11/1993 | Leighton et al. ............. 422/100 |
| 5,310,469 A | 5/1994 | Cunningham et al. |
| 5,378,342 A | 1/1995 | Ikematsu et al. |
| 5,393,401 A | 2/1995 | Knoll |
| 5,443,955 A | 8/1995 | Cornell et al. |
| 5,446,186 A | 8/1995 | Ellis-Davies et al. |
| 5,506,141 A * | 4/1996 | Weinreb et al. .......... 435/309.1 |
| 5,508,200 A | 4/1996 | Tiffany et al. ................. 436/44 |
| 5,510,628 A | 4/1996 | Georger, Jr. et al. |
| 5,512,489 A | 4/1996 | Girault et al. |
| 5,532,128 A | 7/1996 | Eggers et al. |
| 5,563,067 A | 10/1996 | Sugihara et al. |
| 5,605,662 A | 2/1997 | Heller et al. |
| 5,632,957 A | 5/1997 | Heller et al. ................. 422/68.1 |
| 5,750,015 A | 5/1998 | Soane et al. |
| 5,780,752 A | 7/1998 | Okubo et al. |
| 5,810,725 A | 9/1998 | Sugihara et al. |
| 5,858,804 A | 1/1999 | Zanzucchi et al. |
| 5,889,216 A | 3/1999 | Okubo et al. |
| 5,904,824 A | 5/1999 | Oh |
| 5,911,871 A | 6/1999 | Preiss et al. |
| 5,936,728 A | 8/1999 | Bouzid ........................ 356/318 |
| 5,955,352 A | 9/1999 | Inoue et al. |
| 5,958,345 A | 9/1999 | Turner et al. |
| 5,962,081 A | 10/1999 | Öhman et al. |
| 5,981,268 A | 11/1999 | Kovacs et al. |
| 6,008,010 A | 12/1999 | Greenberger et al. |
| 6,015,714 A | 1/2000 | Baldarelli et al. |
| 6,027,695 A | 2/2000 | Oldenburg et al. |
| 6,032,062 A | 2/2000 | Nisch |
| 6,033,916 A | 3/2000 | Sieben et al. |
| 6,043,037 A | 3/2000 | Lucas |
| 6,048,722 A | 4/2000 | Farb et al. |
| 6,056,861 A | 5/2000 | Fuhr et al. |
| 6,063,260 A * | 5/2000 | Olesen et al. ................ 205/793 |
| 6,068,818 A | 5/2000 | Ackley et al. |
| 6,093,296 A | 7/2000 | Soane et al. |
| 6,099,803 A | 8/2000 | Ackley et al. |
| 6,103,479 A | 8/2000 | Taylor |
| 6,106,784 A | 8/2000 | Lund et al. |
| 6,113,768 A | 9/2000 | Fuhr et al. |
| 6,117,291 A | 9/2000 | Olesen et al. |
| 6,132,582 A | 10/2000 | King et al. .................. 204/604 |
| 6,143,496 A | 11/2000 | Brown et al. |
| 6,151,519 A | 11/2000 | Sugihara et al. |
| 6,156,181 A | 12/2000 | Parce et al. |
| 6,163,719 A | 12/2000 | Sherman |
| 6,177,000 B1 | 1/2001 | Peterson |
| 6,207,031 B1 | 3/2001 | Adourian et al. |
| 6,225,059 B1 | 5/2001 | Ackley et al. |
| 6,228,326 B1 | 5/2001 | Boxer et al. |
| 6,235,520 B1 * | 5/2001 | Malin et al. ............. 435/287.1 |
| 6,267,872 B1 | 7/2001 | Akeson et al. ............... 205/775 |
| 6,277,629 B1 | 8/2001 | Wolf et al. |
| 6,284,113 B1 | 9/2001 | Bjornson et al. |
| 6,284,872 B1 | 9/2001 | Celeste et al. ............. 530/399 |
| 6,287,517 B1 | 9/2001 | Ackley et al. |
| 6,315,940 B1 | 11/2001 | Nisch et al. ................. 264/600 |
| 6,329,209 B1 | 12/2001 | Wagner et al. |
| 6,355,491 B1 | 3/2002 | Zhou et al. |
| 6,365,129 B1 | 4/2002 | Fogarty |
| 6,368,851 B1 | 4/2002 | Baumann et al. ......... 435/285.2 |
| 6,376,233 B1 | 4/2002 | Wolf et al. |
| 6,377,057 B1 | 4/2002 | Borkholder ................. 324/692 |
| 6,379,916 B1 | 4/2002 | Meyer |
| 6,448,794 B1 | 9/2002 | Cheng et al. |
| 6,461,860 B2 | 10/2002 | Mathes et al. ........... 435/286.7 |
| 6,470,226 B1 | 10/2002 | Olesen et al. .................. 700/56 |
| 6,475,760 B1 | 11/2002 | Baumann et al. |
| 6,475,808 B1 | 11/2002 | Wagner et al. |
| 6,488,829 B1 | 12/2002 | Schroeder et al. ..... 204/403.01 |
| 6,596,143 B1 | 7/2003 | Wang et al. |
| 6,602,714 B1 | 8/2003 | Tagge et al. |
| 6,613,285 B1 | 9/2003 | Carnahan |
| 6,630,835 B2 | 10/2003 | Cheng et al. |
| 6,635,470 B1 | 10/2003 | Vann |
| 6,638,743 B2 | 10/2003 | Baumann et al. |
| 6,649,357 B2 | 11/2003 | Bryan et al. |
| 6,668,230 B2 | 12/2003 | Mansky et al. |
| 6,670,115 B1 | 12/2003 | Zhang |
| 6,682,649 B1 | 1/2004 | Petersen et al. |
| 6,699,697 B2 | 3/2004 | Klemic et al. |
| 6,762,036 B2 | 7/2004 | Farb et al. |
| 6,764,648 B1 * | 7/2004 | Roach et al. ................... 422/63 |
| 2001/0005489 A1 | 6/2001 | Roach et al. ................... 422/99 |
| 2001/0005774 A1 | 6/2001 | Kato et al. ................... 600/345 |
| 2001/0045359 A1 | 11/2001 | Cheng et al. |
| 2002/0063067 A1 | 5/2002 | Bech et al. |
| 2002/0072103 A1 | 6/2002 | Matsumoto et al. |
| 2002/0074227 A1 | 6/2002 | Nisch et al. |
| 2002/0076825 A1 | 6/2002 | Cheng et al. |
| 2002/0104757 A1 | 8/2002 | Schmidt |
| 2002/0108869 A1 | 8/2002 | Savtchenko |
| 2002/0119579 A1 | 8/2002 | Wagner |
| 2002/0137121 A1 | 9/2002 | Rubinsky et al. |
| 2002/0144905 A1 | 10/2002 | Schmidt |
| 2002/0155586 A1 | 10/2002 | Cheng et al. |
| 2002/0164777 A1 | 11/2002 | Kelly et al. |
| 2002/0182627 A1 | 12/2002 | Wang et al. |
| 2002/0190732 A1 | 12/2002 | Cheng et al. |
| 2002/0195337 A1 | 12/2002 | Osipchuk et al. |
| 2003/0022268 A1 | 1/2003 | Lepple-Wienhues |
| 2003/0052002 A1 | 3/2003 | Vogel et al. |
| 2003/0059936 A1 | 3/2003 | Baumann et al. |
| 2003/0070923 A1 | 4/2003 | Schroeder et al. |
| 2003/0080314 A1 | 5/2003 | Nisch et al. |
| 2003/0098248 A1 | 5/2003 | Vogel et al. |
| 2003/0104512 A1 | 6/2003 | Freeman et al. |
| 2003/0121778 A1 | 7/2003 | Dodgson et al. |
| 2003/0129581 A1 | 7/2003 | Owen et al. |
| 2003/0132109 A1 | 7/2003 | Bullen et al. |
| 2003/0134416 A1 | 7/2003 | Yamanishi et al. |
| 2003/0138767 A1 | 7/2003 | Bullen et al. |
| 2003/0139336 A1 | 7/2003 | Norwood et al. |
| 2003/0146091 A1 | 8/2003 | Vogel et al. |
| 2003/0153067 A1 | 8/2003 | Stett et al. |

| | | | | | | |
|---|---|---|---|---|---|---|
| 2003/0219884 | A1 | 11/2003 | Lison et al. | WO | WO 01/34764 | 5/2001 |
| 2004/0062685 | A1 | 4/2004 | Norton et al. | WO | WO 01/48474 | 7/2001 |
| 2004/0251145 | A1 | 12/2004 | Robertson | WO | WO 01/48475 V | 7/2001 |
| | | | | WO | WO 01/59153 | 8/2001 |
| | | | | WO | WO 01/59447 | 8/2001 |

FOREIGN PATENT DOCUMENTS

| | | | | | |
|---|---|---|---|---|---|
| DE | 4115414 | 11/1992 | WO | WO 01/69241 | 9/2001 |
| DE | 19605830 V | 2/1997 | WO | WO 01/71349 | 9/2001 |
| DE | 19628928 | 1/1998 | WO | WO 01/75438 | 10/2001 |
| DE | 19646505 V | 5/1998 | WO | WO 01/81425 | 11/2001 |
| DE | 19712309 V | 5/1998 | WO | WO 01/86290 | 11/2001 |
| DE | 19815882 V | 10/1999 | WO | WO 01/94939 | 12/2001 |
| DE | 19827957 V | 12/1999 | WO | WO 02/00217 | 1/2002 |
| DE | 19936302 | 2/2001 | WO | WO 02/02608 | 1/2002 |
| DE | 19948473 | 4/2001 | WO | WO 02/03058 | 1/2002 |
| DE | 19961951 | 6/2001 | WO | WO 02/04656 | 1/2002 |
| DE | 10008373 | 9/2001 | WO | WO 02/08748 V | 1/2002 |
| DE | 10022772 V | 11/2001 | WO | WO 02/10747 | 2/2002 |
| DE | 10047390 V | 4/2002 | WO | WO 02/12896 | 2/2002 |
| DE | 10061347 V | 6/2002 | WO | WO 02/16936 | 2/2002 |
| DE | 20220299 V | 5/2003 | WO | WO 02/27909 | 4/2002 |
| DE | 10218325 | 11/2003 | WO | WO 02/28523 | 4/2002 |
| DE | 10254158 | 6/2004 | WO | WO 02/29402 | 4/2002 |
| DE | 10320899 | 12/2004 | WO | WO 02/31505 | 4/2002 |
| EP | 0094193 | 5/1983 | WO | WO 02/52045 V | 7/2002 |
| EP | 0299778 V | 1/1989 | WO | WO 02/59597 | 8/2002 |
| EP | 0299779 | 1/1989 | WO | WO 02/59598 | 8/2002 |
| EP | 0162907 V | 1/1992 | WO | WO 02/59603 U | 8/2002 |
| EP | 0639768 V | 2/1995 | WO | WO 02/65092 | 8/2002 |
| EP | 0960933 V | 5/1999 | WO | WO 02/66596 V | 8/2002 |
| EP | 0962524 V | 9/1999 | WO | WO 02/73159 | 9/2002 |
| EP | 1035918 V | 9/2000 | WO | WO 02/74983 | 9/2002 |
| EP | 1040349 V | 10/2000 | WO | WO 02/77259 | 10/2002 |
| EP | 1178315 V | 2/2002 | WO | WO 02/77627 | 10/2002 |
| EP | 1203823 V | 5/2002 | WO | WO 02/082046 | 10/2002 |
| EP | 0689051 | 11/2002 | WO | WO 02/095357 | 11/2002 |
| EP | 1333279 V | 8/2003 | WO | WO 02/103354 | 12/2002 |
| EP | 1418427 | 5/2004 | WO | WO 03/021230 V | 3/2003 |
| FR | 2659347 V | 9/1991 | WO | WO 03/046216 V | 6/2003 |
| GB | 2360162 V | 5/2001 | WO | WO 03/047738 | 6/2003 |
| GB | 2355354 V | 4/2002 | WO | WO 03/067251 | 8/2003 |
| GB | 2 371 626 V | 7/2002 | WO | WO 03/089564 | 10/2003 |
| GB | 2401689 | 11/2004 | WO | WO 03/093494 | 11/2003 |
| JP | 4-204211 V | 7/1992 | WO | WO 2004/011084 | 2/2004 |
| JP | 4-204244 V | 7/1992 | WO | WO 2004/018690 | 3/2004 |
| JP | 4-338240 V | 11/1992 | WO | WO 2004/021002 | 3/2004 |
| JP | 2003-307481 | 10/2003 | WO | WO 2004/034052 | 4/2004 |
| JP | 2004301529 | 10/2004 | WO | WO 2004/038410 | 5/2004 |
| WO | WO85/02201 V | 5/1985 | WO | WO 2004/044574 | 5/2004 |
| WO | WO89/01159 V | 2/1989 | WO | WO 2004/074829 | 9/2004 |
| WO | WO91/13977 V | 9/1991 | WO | WO 2004/100229 | 11/2004 |
| WO | WO92/21020 | 11/1992 | WO | WO 2005/007866 | 1/2005 |
| WO | WO94/15701 | 7/1994 | WO | WO 2005/012554 | 2/2005 |
| WO | WO94/25862 V | 11/1994 | | | |
| WO | WO96/13721 V | 5/1996 | | | |
| WO | WO97/17426 V | 5/1997 | | | |
| WO | WO97/22875 | 6/1997 | | | |
| WO | WO97/25616 | 7/1997 | | | |
| WO | WO97/40104 V | 10/1997 | | | |
| WO | WO97/46882 | 12/1997 | | | |
| WO | WO97/49987 | 12/1997 | | | |
| WO | WO98/01150 | 1/1998 | | | |
| WO | WO98/22819 V | 5/1998 | | | |
| WO | WO98/47003 | 10/1998 | | | |
| WO | WO98/54294 | 12/1998 | | | |
| WO | WO98/58248 V | 12/1998 | | | |
| WO | WO99/31503 * | 6/1999 | | | |
| WO | WO99/34202 | 7/1999 | | | |
| WO | WO99/66329 | 12/1999 | | | |
| WO | WO 00/25121 | 5/2000 | | | |
| WO | WO 01/07585 | 2/2001 | | | |
| WO | WO 01/25769 | 4/2001 | | | |
| WO | WO 01/27614 | 4/2001 | | | |

OTHER PUBLICATIONS

Adhesion of Cells to Surfaces Coated with Polylysine, Mazia et al., *Journal of Cell Biology*, vol. 66, pp. 198-200, 1975.

The Feynman Lectures on Physics, Feynman et al., pp. 10-1 through 10-5, © Feb. 1977.

Role of Electrogenic Sodium Pump in Slow Synaptic Inhibition is Re-evaluated, Kostyuk et al., *Nature*, vol. 267, May 5, 1977.

Fusion of Phospholipid Vesicles with Planar Phospholipid Bilayer Membranes, Cohen et al., *J. Gen. Physiol.*, vol. 75, pp. 251-270, Mar. 1980.

Preparation of Large Unilamellar Vesicles, Hub et al., *FEBS Letters*, vol. 140, No. 2, pp. 254-256, Apr. 1982.

Formation and Properties of Cell-Size Lipid Bilayer Vesicles, Mueller et al., *Biophysics Journal*, vol. 44, pp. 375-381, Dec. 1983.

Perfusion of Oocytes, Yoshii et al., *Intracellular Perfusion of Excitable Cells*, pp. 77-89, 1984.

*Intracellular Perfusion of Excitable Cells*, Kostyuk et al., pp. 35-51, 1984.

Novel Method of Cell Fusion in Field Constriction Area in Fluid Integrated Circuit, Masuda et al., *IEEE Trans. IAS*, XP-002181725, pp. 1549-1553, Oct. 1987.
A Membrane Fusion Strategy for Single-Channel Recordings of Membranes Usually Non-Accessible to Patch-Clamp Pipette Electrodes, Criado et al., *FEBS Letters*, vol. 224, No. 1, pp. 172-176, Nov. 1987.
Muscarinic Activation of Ionic Currents Measured by a New Whole-Cell Recording Method, Horn et al., *Journal of General Physiology*, vol. 92, pp. 145-159, Aug. 1988.
Controlled Outgrowth of Dissociated Neurons on Patterned Substrates, Kleinfeld et al., *The Journal of Neuroscience*, vol. 8, No. 11, pp. 4098-4120, Nov. 1988.
Single Channel Recordings of Reconstituted Ion Channel Proteins: An Improved Technique, Keller et al., *Pflügers Arch.*, vol. 411, pp. 94-100, 1988.
Anti-T2 Monoclonal Antibody Immobilization on Quartz Fibers: Stability and Recognition of T2 Mycotoxin, Williamson et al., *Analytical Letters*, vol. 22, No. 4, pp. 803-816, 1989.
Current-Voltage Relationships of a Sodium-Sensitive Potassium Channel in the Tonoplast of Chara Corallina, Bertl, *Journal of Membrane Biology*, vol. 109, pp. 9-19, 1989.
Properties and Uses of Photoreactive Caged Compounds, McCray, *Annu. Rev. Biophys. Chem.*, vol. 18, pp. 239-270, 1989.
Optimizing Planar Lipid Bilayer Single-Channel Recordings for High Resolution with Rapid Voltage Steps, Wonderlin et al., *Biophysics Journal*, vol. 58, pp. 289-297, Aug. 1990.
Patch Clamp of Cation Channels, Lewis et al., *Current Topics in Membranes and Transport*, vol. 37, pp. 215-245, 1990.
Reconstitution of Epithelial Ion Channels, Bridges et al., *Current Topics in Membranes and Transport*, vol. 37, pp. 283-312, 1990.
Receptor Screening and the Search for New Pharmaceuticals, Hodgson, *Bio/Technology*, vol. 10, pp. 973-980, Sep. 1992.
Functional Reconstitution of the Nicotinic Acetylcholine Receptor by CHAPS Dialysis Depends on the Concentrations of Salt, Lipid, and Protein, Schürholz et al., *Biochemistry*, vol. 31, pp. 5067-5077, 1992.
Patch Voltage Clamping with Low-Resistance Seals: Loose Patch Clamp, Roberts et al., *Methods in Enzymology*, vol. 207, pp. 155-176, 1992.
Insertion of Ion Channels into Planar Lipid Bilayers by Vesicle Fusion, Labarca et al., *Methods in Enzymology*, vol. 207, pp. 447-463, 1992.
Patch Clamp Techniques: An Overview, Cahalan et al., *Methods in Enzymology*, vol. 207, pp. 3-14, 1992.
Glass Technology for Patch Clamp Electrodes, Rae et al., *Methods in Enzymology*, vol. 207, pp. 66-92, 1992.
Planar Lipid Bilayers on Patch Pipettes: Bilayer Formation and Ion Channels Incorporation, Ehrlich, *Methods in Enzymology*, vol. 207, pp. 463-470, 1992.
*The Axon Guide for Electrophysiology and Biophysics Laboratory Techniques*, Axon Instruments, Inc., Jun. 1993.
*Molecular Biology of the Cell*, Third Edition, Alberts et al., pp. 178-189, © 1994.
Modeling Success and Failure of Langmuir-Blodgett Transfer of Phospholipid Bilayers to Silicon Dioxide, Osborn et al., *Biophysical Journal*, vol. 68, pp. 1364-1373, Apr. 1995.
Patterning Self-Assembled Monolayers Using Microcontact Printing: A New Technology for Biosensors?, Mrksich et al., *TBTech*, vol. 13, pp. 228-235, Jun. 1995.
Lipid Vesicle Adsorption Versus Formation of Planar Bilayers on Solid Surfaces, Nollert et al., *Biophysical Journal*, vol. 69, pp. 1447-1455, Oct. 1995.
Phenomenology and Kinetics of Lipid Bilayer Spreading on Hydrophilic Surfaces, Rädler et al., *Langmuir*, vol. 11, No. 11, pp. 4539-4548, 1995.
A Highly Stable and Selective Biosensor Using Modified Nicotinic Acetylcholine Receptor (nAChR), Eray et al., *BioSystems*, vol. 35, pp. 183-188, 1995.
G Proteins and Regulation of Adenylate Cyclase (Nobel Lecture), Gilman, *Angew. Chem. Int. Ed. Engl.*, vol. 34, pp. 1406-1419, 1995.
Signal Transduction: Evolution of an Idea (Nobel Lecture), Rodbell, *Angew. Chem. Int. Ed. Engl.*, vol. 34, pp. 1420-1428, 1995.

Shape Change and Physical Properties of Gian Phospholipid Vesicles Prepared in the Presence of an AC Electric Field, Mathivet et al., *Biophysical Journal*, vol. 70, pp. 1112-1121, Mar. 1996.
McCrone "Microscopy" from Kirk-Othmer, *Encyclopedia of Chemical Technology*, pp. 651, 658-659, 1995.
Positive Chronotropic Responses of Rabbit Sino-Atrial Node Cells to Flash Photolysis of Caged Isoproterenol and Cyclic AMP, Tanaka et al., *Prc. R. Soc. Lond. B. Biol. Sci.*, vol. 263, No. 1368, pp. 241-248 (abstract only), Mar. 1996.
Ion Channels from Synaptic Vesicle Membrane Fragments Reconstituted into Lipid Bilayers, Kelly et al., *Biophysical Journal*, vol. 70, pp. 2593-2599, Jun. 1996.
Controlling Cell Attachment on Contoured Surfaces with Self-Assembled Monolayers of Alkanethiolates on Gold, Mrksich et al., *Proc. Natl. Acad. Sci. USA*, vol. 93, pp. 10775-10778, Oct. 1996.
Preparation of Giant Liposomes in Physiological Conditions and Their Characterization Under an Optical Microscope, Akashi et al., *Biophysical Journal*, vol. 71, pp. 3242-3250, Dec. 1996.
Preparation of Giant Myelin Vesicles and Proteoliposomes to Register Ionic Channels, Regueiro et al., *Journal of Neurochemistry*, vol. 67, No. 5, pp. 2146-2154, 1996.
Critical Dependence of the Solubilization of Lipid Vesicles by the Detergent CHAPS on the Lipid Composition. Functional Reconstitution of the Nicotinic Acetylcholine Receptor Into Preformed Vesicles Above the Critical Micellization Concentration, Schürholz, *Biophysical Chemistry*, vol. 58, pp. 87-96, 1996.
A Novel Chloride Channel in *Vicia faba* Guard CellVacuoles Activated by the Serine/Threonine Kinase, CDPK, Pei et al., *EMBO Journal*, vol. 15, No. 23, pp. 6564-6574, 1996.
Investigating Channel Activity, Aidley et al., *Ion Channels: Molecules in Action*, pp. 33-57, 1996.
Comparison of Na+/K+-ATPase Pump Currents Activated by ATP Concentration or Voltage Jumps, Friedrich et al., *Biophysical Journal*, vol. 73, pp. 186-194, Jul. 1997.
A Cyclic Nuecleotide-Dependent Chloride Conductance in Olfactory Receptor Neurons, Delay et al., *Journal of Membrane Biology*, vol. 159, No. 1, pp. 53-60, (abstract only), Sep. 1997.
Single Binding Versus Single Channel Recordings: A New Approach to Study Ionotropic Receptors, Edelstein et al., *Biochemistry*, vol. 36, No. 45, pp. 13755-17650, 1997.
Restricted Photorelease of Biologically Active Molecules Near the Plasma Membrane, Suga et al., *Biochemical and Biophysical Research Communications*, vol. 253, Issue 2, pp. 423-430 (abstact only), Dec. 1998.
UV Photolysis Using a Micromanipulated Optical Fiber to Deliver UV Energy Directly to the Sample, Parpura et al., *Journal of Neuroscience Methods*, vol. 87, issue 1, pp. 25-34 (abstract only), Feb. 1999.
Nystatin/Ergosterol Method for Reconstituting Ion Channels into Planar Lipid Bilayers, Woodbury, *Methods in Enzymology*, vol. 294, pp. 319-350, 1999.
Isolation of Transport Vesicles that Deliver Ion Channels to the Cell Surface, Sattsangi et al., *Methods in Enzymology*, vol. 294, pp. 339-350 (abstract only), 1999.
*New UC Berkeley "Bionic Chip" Features Living Biological Cell Successfully Merged With Electronic Circuitry*, University of California Berkeley, Press Release, Feb. 25, 2000.
*Researchers Make 'Bionic Chip,'* Edwards, Associated Press, Feb. 25, 2000.
A Chip-Based Biosensor for the Functional Analysis of Single Ion Channels, Schmidt et al., *Angew. Chem. Int. Ed 2000*, vol. 39, No. 17, pp. 3137-3140, 2000.
Osmotically Evoked Shrinking of Guard-Cell Protoplasts Causes Vesicular Retrieval of Plasma Membrane into the Cytoplasm, Kubitscheck et al., *Planta*, vol. 210, 423-431, 2000.
Hungary Patent Document No. HU 200000996, dated Nov. 28, 2001.
The Lipid Bilayer Concept and its Experimental Realization: From Soap Bubbles, Kitchen Sink, to Bilayer Lipid Membranes, Tien et al., *Journal of Membrane Science*, vol. 189, pp. 83-117, 2001.
*NEURON Programming Tutorial #1*, Martin, Internet pp. 1-7, Mar. 3, 2002.

*Introduction to Voltage Clamp and Current Clamp*, Purves, Internet pp. 1-2, Mar. 3, 2002.
Microfluidics-Based lab-on-a-chip Systems, Weigl, *IVDT*, pp. 1-6, internet reprint Apr. 11, 2002.
*Patch Clamping Directly Measures Ionic Current*, Sophion Bioscience, Internet pp. 1-2, May 1, 2002.
*Patch Clamp Technique*, Nanion Products, Internet pp. 15, May 1, 2002.
Patch Clamp on a Chip, Sigworth et al., *Biophysical Journal*, vol. 82, pp. 2831-2832, Jun. 2002.
*A Microfabricated Chip for the Study of Cell Electroporation*, Huang et al., pp. 1-4, undated.
HTS Approaches to Voltage-Gated Ion Channel Drug Discovery, Denyer et al., *Drug Discovery Today*, vol. 3, No. 7, pp. 323-332, Jul. 1998.
Cell-Based Assays and Instrumentation for Screening Ion-Channel Targets, Gonzalez et al., *Drug Discovery Today*, vol. 4, No. 9, pp. 431-439, Sep. 1999.
Microstructured Glass Chip for Ion-Channel Electrophysiology, Fertig et al., *Physical Review E*, vol. 64, No. 4, Part 1, pp. 040901-1 to 040901-4, Sep. 2001.
Ion-Channel Assay Technologies: Quo Vadis?, Xu et al., *Drug Discovery Today*, vol. 6, No. 24, pp. 1278-1287, Dec. 2001.
Whole Cell Patch Clamp Recording Performed on a Planar Glass Chip, Fertig et al., *Biophysical Journal*, vol. 82, pp. 3056-3062, Jun. 2002.
Micromolded PDMS Planar Electrode Allows Patch Clamp Electrical Recordings From Cells, Klemic et al., *Biosensors and Bioelectronics*, vol. 17, pp. 597-604, Jun. 2002.
An Interview with Kirk S. Schroeder, President, Essen Instruments, *Assay and Drug Development Technologies*, vol. 1, No. 1-1, pp. 3-8, 2002.
IonWorks™ HT: A New High-Throughput Electrophysiology Measurement Platform, Schroeder et al., *Journal of Biomolecular Screening*, vol. 8, No. 1, pp. 50-64, Feb. 2003.
Characterization of a Micromachined Planar Patch Clamp for Cellular Electrophysiology, Matthews et al., *1st International IEEE EMBS Neural Engineering Conference*, pp. 1-4, Mar. 20-22, 2003.
Automated Electrophysiology: High Throughput of Art, Wang et al., *Assay and Drug Development Technologies*, vol. 1, No. 5, pp. 695-708 (reprint pp. 1-13), Oct. 2003.
High Throughput Ion-Channel Pharmacology: Planar-Array-Based Voltage Clamp, Kiss et al., *Assay and Drug Development Technologies*, vol. 1, No. 1, Part 2, pp. 127-135, Feb. 2003.
Patchers v. Screeners: Divergent Opinion on High Throughput Electro-physiology, Comley, *Drug Discovery World*, pp. 47-57, Fall 2003.
High Throughput Electrophysiology: New Perspectives for Ion Channel Drug Discovery, Willumsen, *Receptors and Channels*, vol. 9, No. 1, pp. 3-12, 2003.
High Throughput Electrophysiology Using a Fully Automated, Multiplexed Recording System, Trumbull et al., *Receptors and Channels*, vol. 9, No. 1, pp. 19-28, 2003.
Microstructured Apertures in Planar Glass Substrates for Ion Channel Research, Fertig et al., *Receptors and Channels*, vol. 9, No. 1, pp. 29-40, 2003.
Upscaling and Automation of Electrophysiology: Toward High Throughput Screening in Ion Channel Drug Discovery, Asmild et al., *Receptors and Channels*, vol. 9, No. 1, pp. 49-58, 2003.
CYTOCENTERING: A Novel Technique Enabling Automated Cell-by-Cell Patch Clamping with the CYTOPATCH™ Chip, Stett et al., *Receptors and Channels*, vol. 9, No. 1, pp. 59-66, 2003.
Screening Technologies for Ion Channel Targets in Drug Discovery, Zheng et al., *American Pharmaceutical Review*, pp. 85-92, 2003.
Intracellular Perfusion of Helix Giant Neurons, Kryshtal et al., *Neirofiziologiya*, vol. 7, No. 3, pp. 327-329 (reprinted in English as pp. 258-259), May-Jun. 1975.
Current Fluctuations, Associated with the Activation of Calcium Channel Mechanism in the Membrane of Nerve Cells, Kristhal et al., *USSR Academy of Science Report*, vol. 231, No. 5, 1976.
Asymmetrical Displacement Currents in Nerve Cell Membrane and Effect of Internal Fluoride, Kostyuk et al., *Nature*, vol. 267, pp. 70-72, May 5, 1977.

Separation of Sodium and Calcium Currents in the Somatic Membrane of Mollusc Neurones, Kostyuk et al., *J. Physiol.*, vol. 270, pp. 545-568, 1977.
Properties of Internally Perfused, Voltage-Clamped, Isolated Nerve Cell Bodies, Lee et al., *Journal of General Physiology*, vol. 71, pp. 489-507, 1978.
Ionic Currents in the Neuroblastoma Cell Membrane, Kostyuk et al., *Neuroscience*, vol. 3, pp. 327-332, 1978.
The Extracellular Patch Clamp: A Method for Resolving Currents Through Individual Open Channels in Biological Membranes, Neher et al., *Pflugers Arch.*, vol. 375, pp. 219-228, 1978.
*Effects of Internal Free Calcium Upon the Sodium and Calcium Channels in the Tunicate Egg Analysed by the Internal Perfusion Technique*, Takahashi et al., vol. 279, pp. 519-549, 1978.
Single Acetylcholine-Activated Channels Show Burst-Kinetics in Presence of Desensitizing Concentrations of Agonist, Sakmann et al., *Nature*, vol. 286, pp. 71-73, Jul. 3, 1980.
Single Na+ Channel Currents Observed in Cultured Rat Muscle Cells, Sigworth et al., *Nature*, vol. 287, pp. 447-449, Oct. 2, 1980.
A Receptor for Protons in the Nerve Cell Membrane, Krishtal et al., *Neuroscience*, vol. 5, pp. 2325-2327, 1980.
Fluctuations in the Microsecond Time Range of the Current Through Single Acetylcholine Receptor Ion Channels, Colquhoun et al., *Nature*, vol. 294, pp. 464-466, Dec. 3, 1981.
Intracellular Perfusion, Kostyuk et al., *Journal of Neuroscience Methods*, vol. 4, pp. 201-210, 1981.
Receptor for Protons in the Membrane of Sensory Neurons, Krishtal et al., *Brain Research*, vol. 214, pp. 150-154, 1981.
A 'Receptor' for Protons in Small Neurons of Trigeminal Ganglia: Possible Role in Nociception, Krishtal et al., *Neuroscience Letters*, vol. 24, pp. 243-246, 1981.
Intracellular Perfusion, Kostyuk, *Ann. Rev. Neurosci.*, vol. 5, pp. 102-120, 1982.
Science and Technology of Patch-Recording Electrodes, Corey et al., *Single-Channel Recording*, pp. 53-68, 1983.
Perfusion of Isolated Neurons Fixed in Plastic Film, Kostyuk et al., *Intracellular Perfusion of Excitable Cells*, pp. 35-51, 1984.
Electrical Measurements on Perfused Cells, Osipchuk et al., *Intracellular Perfusion of Excitable Cells*, pp. 103-129, 1984.
The Patch Clamp is More Useful Than Anyone had Expected, Sigworth, *Federation Proceedings*, vol. 45, No. 12, pp. 2673-2677, Nov. 1986.
Quantitative Video Microscopy of Patch Clamped Membranes Stress, Strain, Capacitance, and Stretch Channel Activation, Sokabe et al., *Biophysical Journal*, vol. 59, pp. 722-728, Mar. 1991.
Perfusion of Nerve Cells and Separation of Sodium and Calcium Currents, Kostyuk, *Cellular Neurobiology: A Practical Approach*, pp. 121-135, 1991.
The Patch Clamp Technique, Neher et al., *Scientific American*, vol. 266, pp. 44-51, Mar. 1992.
A Novel Method for Glass Micropipette Polishing for Electropatch Clamp Recording Using Oxygen Plasma, Itoh et al., *Biochemical and Biophysical Research Communications*, vol. 191, No. 2, pp. 447-452, 1993.
Fast 3D Laser Micromachining of Silicon for Micromechanical and Microfluidic Applications, Mullenborn et al., *The 8th International Conference on Solid-State Sensors and Actuators, and Eurosensors IX*, pp. 166-169, Jun. 25-29, 1995.
A Practical Guide to Patch Clamping, Penner, *Single-Channel Recording*, pp. 3-30, 1995.
Geometric Parameters of Pipettes and Membrane Patches, Sakmann et al., *Single-Channel Recording*, pp. 637-650, 1995.
Glass-Funnel Technique for the Recording of Membrane Currents and Intracellular Perfusion of Xenopus Oocytes, Shuba et al., *Pflugers Arch.—Eur. J. Physiol.*, vol. 432, pp. 562-570, 1996.
Seal-Promoting Solutions and Pipette Perfusion for Patch Clamping Plant Cells, Maathuis et al., *The Plant Journal*, vol. 11, No. 4, pp. 891-896, 1997.
A 0.1-700 Hz Current Through a Voltage-Clamped Pore: Candidate Protein for Initiator of Neural Oscillations, McGeoch et al., *Brain Research*, vol. 766, pp. 188-194, 1997.

Fabrication of a Novel Microsystem for the Electrical Characterisation of Cell Arrays, Hediger et al., *Sensors and Actuators*, vol. 56, pp. 175-180, 1999.

Electroporation of Cells and Tissues, Weaver, *IEEE Transactions on Plasma Science*, vol. 28, No. 1, pp. 24-33, Feb. 2000.

Characterization of Single-Cell Electroporation by Using Patch-Clamp and Fluorescence Microscopy, Ryttsen et al., *Biophysical Journal*, vol. 79, pp. 1993-2001, Oct. 2000.

Biological-to-Electronic Interface with Pores of ATP Synthase Subunit C in Silicon Nitride Barrier, McGeoch et al., *Medical & Biological Engineering & Computing*, vol. 38, pp. 113-119, 2000.

Planar Patch Clamping not an Automatic Choice, Shah. *Drug Discovery & Development*, pp. 59-63, Jul. 2004.

Characterization, Toxicity and Therapeutic Efficacy of Adriamycin Encapsulated in Liposomes, Olson et al., *European Journal of Cancer & Clinical Oncology*, vol. 18, No. 2, pp. 167-176, Feb. 1982 (abstract only).

Impedance Analysis of Support Lipid Bilayer Membranes: A Scrutiny of Different Preparation Techniques, Steinem et al., *Biochimica et Biophysica Acta*, vol. 1279, pp. 169-180, 1996.

Planar Lipid Bilayers on Solid Supports From Liposomes—Factors of Importance for Kinetics and Stability, Puu et al., *Biochimica et Biophysica Acta*, vol. 1327, pp. 149-161, 1997.

Automated Patch-Clamps Enable Faster Ion Screening, McGee, *Drug Discovery & Development*, pp. 51-53, Jan. 2005.

Characterization of a hERG Screen Using the IonWorks HT: Comparison to a hERG Rubidium Efflux Screen, Sorota et al., *Assay and Drug Development Technologies*, vol. 3, No. 1, pp. 47-57, 2005.

Cloe Screen™ HERG Safety Single Cell Planar Patch Clamp Method article/information pages, Cyprotex, undated (internet print date May 4, 2005).

* cited by examiner

Experimental-Protocol Properties

Name File | Start --> Seal Test | Access --> End | Analyze Data

Select a File-Naming Method

○ Date Prefix
  — Files will be named MMDDYYYY_n#.ihe
  Example: "08242002_n64.ihe"

● Custom Prefix: [Aug22]
  — Files will be named CCCCC_n#.ihe
  Example: "MyData_n1.ihe"

○ Prompt at Run Time
  — User is prompted for a file prefix when the experiment begins. Files will be named CCCCC.ihe
  Example: "MyPrefix.ihe"

Select a folder for saving experimental data: [Browse for Folder...]
C:\Data\Aug22__Essen

[OK]  [Cancel]  [Apply]  [Help]

Experiment Summary

Fluid-handling and coverage:
Single addition using the whole plate

| Experiment Step | Step Duration |
|---|---|
| Start | 0m, 27s |
| Prime Plate | 4m, 30s |
| Add Cells | 1m, 45s |
| Seal Test | 4m, 10s |
| Min: -100 mV, Max: -90 mV, Period: 160 msec | |
| Wait 200 sec before running the test | |
| Obtain Access | 10m, 50s |
| 1. Pause for 120 sec | |
| 2. Introduce Agent for 70 sec | |
| 3. Circulate fluid for 240 sec | |
| 4. Pause for 220 sec | |
| Measure Currents | 16m, 36s |
| Apply signal: once with no repetitions | |
| Command voltage time = 120 msec | |
| Pre/Post Holding time = 30/0 sec; Sample interval = 0.1 msec | |
| Offset-voltage correction (mV): Pre = -10, Post = -5 | |
| Draw compounds from Plate 1: | |
| - COSTAR Half-Area, 96 wells | |
| Compound Incubation Time = 180 sec | |
| Use a "Half-at-Once" scan | |
| Clean Up | 2m, 9s |
| Estimated Experiment Time = | 40m, 27s |

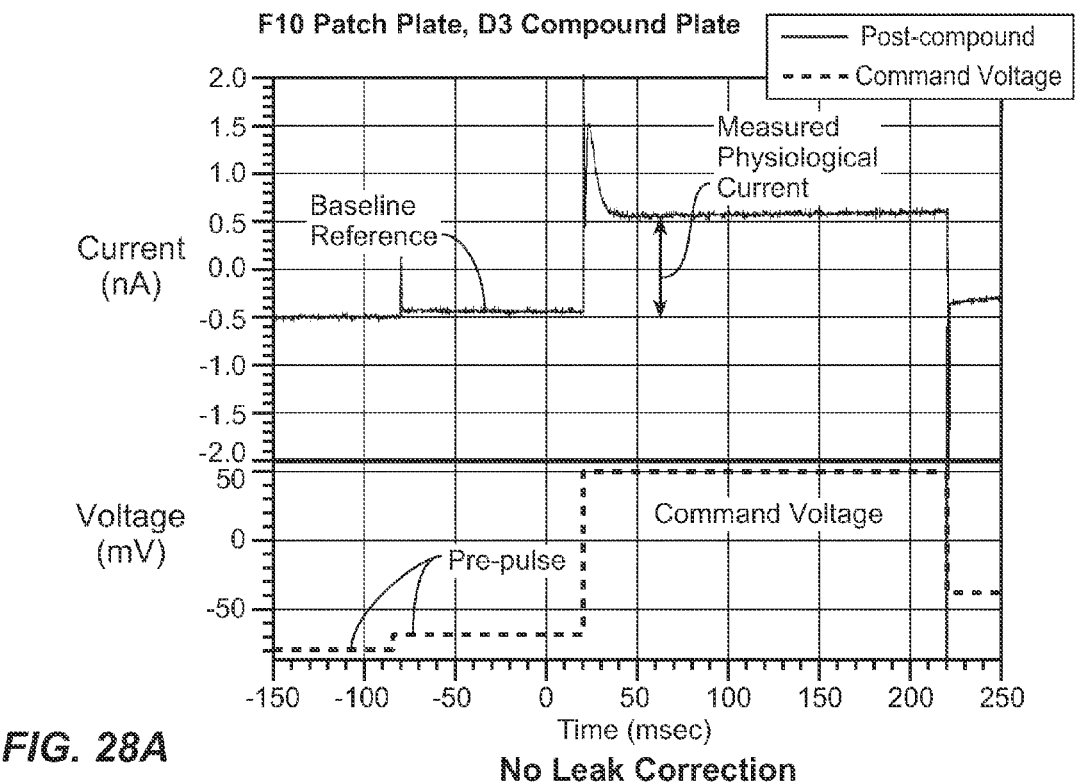
FIG. 28A  No Leak Correction
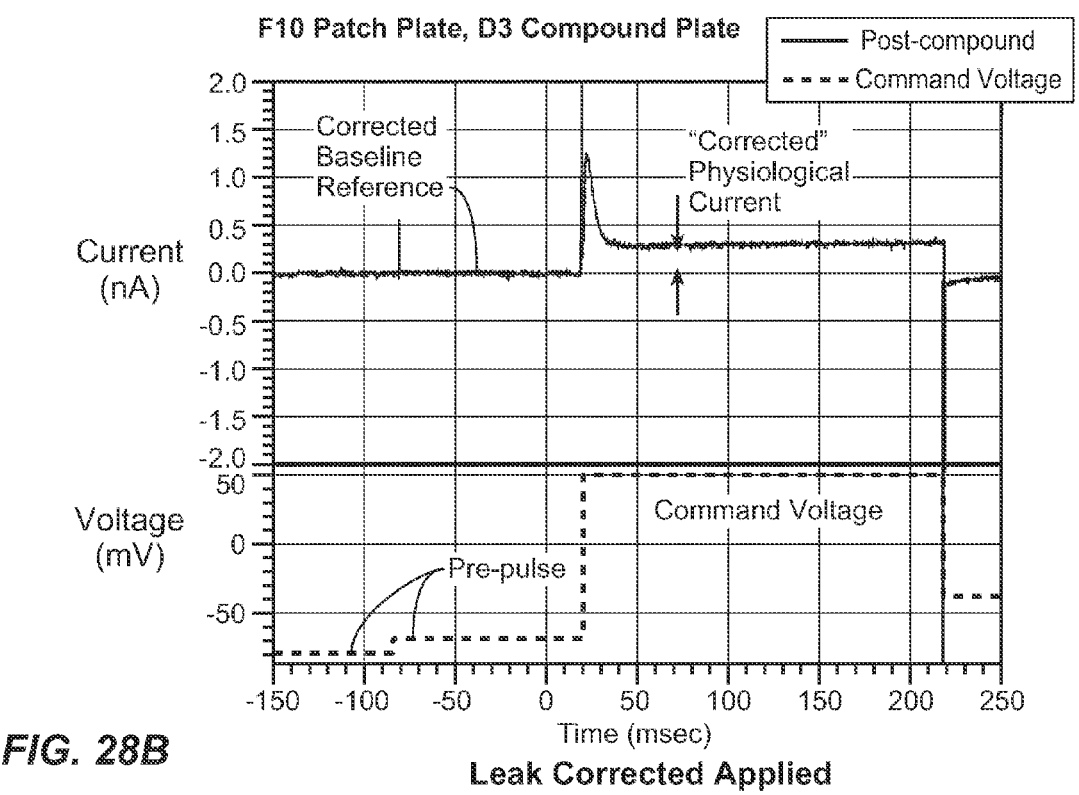
FIG. 28B  Leak Corrected Applied

HIGH-THROUGHPUT ELECTROPHYSIOLOGICAL MEASUREMENT SYSTEM

CROSS-REFERENCES TO RELATED APPLICATIONS

This application is a continuation-in-part of the following patent applications: U.S. patent application Ser. No. 09/631,909, filed Aug. 4, 2000, now U.S. Pat. No. 6,488,829; U.S. patent application Ser. No. 09/862,056, filed May 21, 2001, now U.S. Pat. No. 7,067,046; and PCT Patent Application Serial No. PCT/US02/16122, filed May 21, 2002. This application also claims the benefit under 35 U.S.C. § 119(e) of the following U.S. provisional patent applications: Ser. No. 60/317,112, filed Sep. 6, 2001; and Ser. No. 60/383,196, filed May 22, 2002.

U.S. patent application Ser. No. 09/631,909, in turn, claims the benefit under 35 U.S.C. § 119(e) of the following U.S. provisional patent applications: Ser. No. 60/147,253, filed Aug. 5, 1999; and Ser. No. 60/176,698, filed Jan. 18, 2000.

U.S. patent application Ser. No. 09/862,056, in turn, is a continuation-in-part of U.S. patent application Ser. No. 09/631,909, which, in turn, claims priority directly from two U.S. provisional patent applications, as indicated above.

PCT Patent Application Serial No. PCT/US02/16122, in turn, is a continuation-in-part of U.S. patent application Ser. No. 09/862,056, filed May 21, 2001, which, in turn, claims priority directly and indirectly from several U.S. and provisional patent applications, as indicated above.

The above-identified U.S., PCT, and provisional priority patent applications are all incorporated herein by reference in their entirety for all purposes.

CROSS-REFERENCES TO ADDITIONAL MATERIALS

This application incorporates by reference in their entirety for all purposes the following publications: Richard P. Haugland, HANDBOOK OF FLUORESCENT PROBES AND RESEARCH CHEMICALS ($6^{th}$ ed. 1996); and Joseph R. Lakowicz, PRINCIPLES OF FLUORESCENCE SPECTROSCOPY ($2^{nd}$ ed. 1999).

FIELD OF THE INVENTION

The invention relates to electrophysiology. More particularly, the invention relates to systems for performing electrophysiological measurements, typically in parallel, and typically without direct human intervention, especially to understand the properties and/or interactions of specific membrane components, such as ligand-gated ion channels and/or transporters.

BACKGROUND OF THE INVENTION

The electrical behavior of cells and cell membranes is of profound importance in basic research as well as in modern drug development. A specific area of interest in this field is in the study of ion channels and transporters [1]. Ion channels are protein-based pores found in the cell membrane that are responsible for maintaining the electrochemical gradients between the extracellular environment and the cell cytoplasm. These channels quite often are selectively permeable to a particular type of ion, e.g., calcium, chloride, potassium, or sodium. The channels generally comprise two parts: (1) the pore itself, and (2) a switch mechanism that regulates the conductance of the pore. The switch mechanism may be controlled by transmembrane voltage changes, covalent modification, mechanical stimulation, and/or chemical ligands (e.g., through the activation or deactivation of an associated membrane receptor), among others. Ion channels are passive elements in that, once opened, ions flow in the direction of existing electrochemical gradients. Ion transporters are similar to ion channels in that they are involved in the transport of ions across cell membranes; however, they differ from ion channels in that they require energy for their function and in that they tend to pump actively against established electrochemical gradients.

Ion channels are prevalent in the body and are necessary for many physiological functions, including the beating of the heart, the contraction of voluntary muscles, and the signaling of neurons. They also are found in the linings of blood vessels, allowing for physiological regulation of blood pressure, and in the pancreas, allowing for the control of insulin release. As such, the study of ion channels is a very diverse and prolific area encompassing basic academic research as well as biotechnical and pharmaceutical research. Experiments on ion channels may be performed on cell lines that endogenously express the ion channel of interest ("native channels") as well as on recombinant expression systems such as the *Xenopus oocyte* or mammalian cell lines (e.g., CHO, HEK, etc.) that have been transiently or stably transfected to express the ion channel by well-known techniques [2, 3]. Electrophysiology also is performed on isolated cell membranes or vesicles as well as on synthetic membranes where solubilized channels are reconstituted into a manufactured membrane [4].

I. Instrumentation

To date, the most useful and widely utilized tool for the study of ion channels and transporters is a technique called "patch clamping." This technique was first introduced almost 25 years ago [5-7], and consists of using a small glass capillary to function as an electrode in measuring currents and voltages from individual cells. FIG. 1 shows a typical patch clamp measurement geometry. A glass capillary 2 is first heated and pulled to a fine tip. The capillary is then filled with a saline buffer solution 4 and fitted with a Ag/AgCl electrode 6. The function of the Ag/AgCl electrode is to provide an electrical connection to a wire via the reversible exchange of chloride ions in the pipette solution.

Through the use of a microscope and micromanipulating arm (not shown), the user finds a biological cell or cell membrane 8 containing ion channels 10 of interest and gently touches the cell membrane with the pipette. The measurement circuit is completed via the external ionic solution 12 and a second Ag/AgCl bath electrode 14. A high-impedance operational amplifier 16 senses the current flowing in the circuit, which is subsequently recorded and analyzed with a data recording system 18. A key to the successful function of the technique is the ability to form a high electrical resistance (~1 GΩ) seal between the glass pipette and the cell membrane 20, so that the current recorded by the amplifier is dominated by ions 22 flowing through the cell membrane and not by ions flowing around the glass pipette directly into the bath solution.

Once a high-resistance seal is achieved between the pipette and the cell membrane, there are many measurement configurations that the system can take, including the "whole-cell," "perforated-patch," and "inside-out" patch clamp configurations. The whole-cell voltage clamp is one of the more common configurations. In the whole-cell voltage clamp, the portion of membrane at the end of the pipette 24 is permeabilized so as effectively to place the pipette electrode inside the cell. This, in turn, allows for an external voltage command 26 to be placed between the intracellular pipette electrode and the extracellular bath electrode, thereby providing control of the cell's transmembrane voltage potential. The term "whole cell" is derived from the fact that, with this configuration, the instrument measures the majority of the currents in the entire cell membrane.

The electrical permeabilization of the membrane at the end of the pipette can be induced in many ways. Permeabilization often is achieved by using voltage pulses of sufficient strength and duration that the membrane inside the pipette physically breaks down. This approach is well known in the field and is commonly referred to as "zapping" [8]. Permeabilization also may be achieved by using certain antibiotics, such as Nystatin and Amphotericin B [9]. These antibiotics work by forming chemical pores in the cell membrane that are permeable to monovalent ions, such as chloride. Since chloride is the current-carrying ion for the commonly used Ag/AgCl electrode, these antibiotics can produce a low resistance electrical access to the interior of the cell. The advantage of the chemical technique is that the membrane patch remains intact so that larger intracellular molecules remain inside the cell, rather than being flushed out by the pipette solution as with the zapping technique. This approach also is well known in the field and is commonly referred to as a "perforated patch" [8-10].

The formation of high-resistance electrical seals enables the measurement system to detect very small physiological membrane currents (e.g., $\sim 10^{-12}$ A). In addition, by perforating a portion of the cell membrane either electrically or chemically, it is possible to control the voltage (voltage clamp) or current (current clamp) across the remaining intact portion of the cell membrane. This greatly enhances the utility of the technique for making physiological measurements of ion channel/transporter activity, since quite often this activity is dependent on transmembrane voltage. By being able to control the trans-membrane voltage (or current), it is possible to stimulate or deactivate ion channels or transporters with great precision and as such greatly enhance the ability to study complex drug interactions.

The development of the patch clamp technique revolutionized the field of electrophysiology, allowing for the direct electrical measurement of ion channel/transporter events in living cells, cell membranes, and artificial membranes. However, existing patch clamp techniques require operators with high levels of manual dexterity who must learn to record data from single cell or membrane preparations using a small glass capillary positioned under a microscope by a micromanipulating arm. Moreover, even skilled operators typically require tens of minutes to complete a single recording session, while, in the case of drug screening, it generally is preferable to obtain a new cell sample for each different chemical entity to be tested. Thus, existing techniques are not capable of looking at thousands of different conditions (e.g., chemical stimuli) per day, a common need in the biotechnical or pharmaceutical industry.

U.S. Pat. No. 6,063,260 to Olesen describes a system intended to improve the throughput and decrease the fluid volume required of standard patch clamp technology. The improvement relies on using a standard HPLC autosampler apparatus integrated into a standard patch clamp arrangement to more easily inject multiple fluids samples into the measurement system. The invention claims to increase throughput by making multiple sequential fluid additions to the same biological membrane faster and easier. However, the Olesen invention is deficient in several respects. First, it does not allow for a plurality of different biological samples to be measured simultaneously. Second, it does not eliminate the labor-intensive aspects of micromanipulation involved in standard patch clamp electrophysiology. Third, it does not address cases in biological drug screening where multiple chemical reagent additions to the same biological sample are to be avoided (as in the case of high-throughput drug screening).

Published PCT Application No. WO 99/66329 discusses the use of a perforated screen to conduct tests on biological materials, but the proposed system has significant, severe limitations in terms of practical implementation. For example, all embodiments discussed in the WO 99/66329 application utilize multiple apertures per fluid well, placing reliance on the growth of confluent cell matrices to effectuate sealing of the multiple perforations formed in relatively thick material. In addition, although the published application makes reference to automation, no workable, fully integrated systems are disclosed that are capable of high throughput and reliability.

The invention may address these and/or other shortcomings by providing instrumentation for automated, high-throughput studies of ion channels.

II. Ion Channel Assays

The rapid and diverse signaling kinetics of ion channels makes their study both interesting and technically challenging. Many ion channels can be activated and then deactivated in a few milliseconds. This rapid time scale implies that the instrumentation used to study channel kinetics should have a fairly high frequency bandwidth, for example, on the order of 10 kHz. Fortunately, such bandwidths are attainable, since high-bandwidth operational amplifiers are readily available. Unfortunately, this rapid time scale further implies that the method of stimulating ion channel events also should be fast.

The needed time scale of the stimulus depends in part on whether the channels are voltage gated or ligand gated. Voltage gated channels are activated or deactivated by changes in transmembrane voltage, as mentioned previously. For these channels, the same electronics used to record ion channel currents also can be used to control the voltage stimulus, since the time bandwidth of the stimulus, an electrical signal, is inherently fast enough to avoid degrading the kinetics of the voltage-gated ion channel signals. In contrast, ligand-gated channels are activated or deactivated by chemical or ligand binding. These channels may be gated by specific chemical messengers, such as the release of intracellular calcium, adenosine 3',5'-monophosphate (cyclic AMP or cAMP), or acetylcholine (ACh), among others. In some cases, the chemical activation of an ion channel is extracellular in its initiation, and, in other cases, the chemical activation is intracellular. This implies that it is important that the compound not only can be released on the time scale of tens of milliseconds, but in some cases that the compound can be introduced within the membrane of a living cell.

The invention may address these and/or other shortcomings by providing channel assays for automated, high-throughput studies of voltage and/or ligand-gated ion channels.

SUMMARY OF THE INVENTION

The invention provides systems, including apparatus and methods, for performing electrophysiological measurements on membranous samples, including living cells, isolated cell fragments (such as organelles), and/or artificial membranes (such as vesicles). The apparatus may include a high-throughput electrophysiological measurement system, and components thereof. This measurement system may include, among others, (1) a fluidics head for transferring samples and/or other compounds to a perforated measurement substrate, (2) a pressure-regulated plenum system for positioning samples on the substrate and subsequently forming a high-resistance electrical seal, (3) an activation system (such as a computer-controlled pulsed UV illumination module) for activating caged compounds, (4) an electronics head for applying and/or measuring voltage and/or current, and/or (5) a computer-controlled analysis system for collecting and/or analyzing data. The methods may include methods for performing high-throughput electrophysiological measurements on transporters and voltage or ligand-gated ion channels, sequentially and/or simultaneously.

BRIEF DESCRIPTION OF DRAWINGS

FIG. 20 is a screen shot from an exemplary graphical user interface regarding data file naming conventions, directory handling, and display of experiment summaries, in accordance with aspects of the invention.

FIG. 22 is a screen shot from an exemplary graphical user interface regarding the setup and timing of the addition of a perforation agent to the experimental protocol, along with experiment "type" definitions, in accordance with aspects of the invention.

FIG. 24 is a screen shot from an exemplary graphical user interface regarding the setup and timing of the fluidics head compound additions and manual voltage offset corrections used in high-throughput electrophysiological recordings, in accordance with aspects of the invention.

FIG. 25 is a screen shot from an exemplary graphical user interface regarding the display of compiled success rates and plate "hits" for a high-throughput electrophysiological data set, in accordance with aspects of the invention.

FIG. 27 is a screen shot from an exemplary graphical user interface regarding the setup and definition processing "metrics" used in data reduction analysis of high-throughput electrophysiological recordings, in accordance with aspects of the invention.

FIG. 28 are time traces of electrophysiological data showing the effects of resistance leak correction on a high-throughput electrophysiological data trace, in accordance with aspects of the invention.

DETAILED DESCRIPTION

Figure 1:
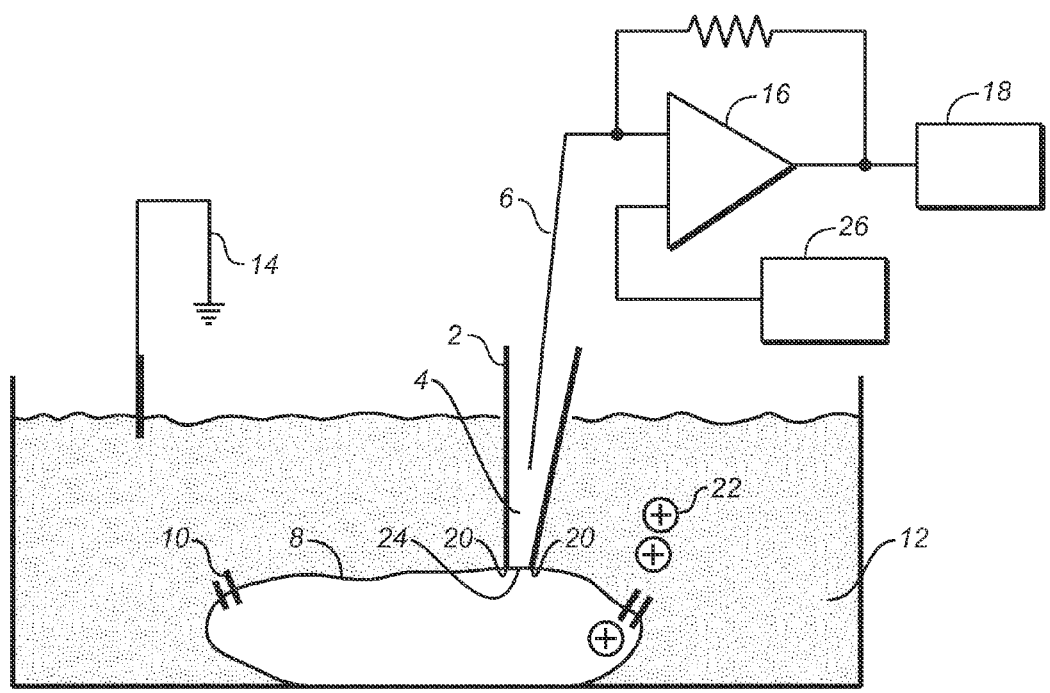
FIG. 1 is a schematic view of a prior-art patch clamp electrophysiology configuration, showing measurement geometry.

The invention provides systems, including apparatus and methods, for performing electrophysiological measurements on membranous samples, including living cells, isolated cell fragments (such as organelles), and/or artificial membranes (such as vesicles). The apparatus may include a high-throughput electrophysiological measurement system, and components thereof. This measurement system may include, among others, (1) a fluidics head for transferring samples and/or other compounds to a perforated measurement substrate, (2) a pressure-regulated fluidics system for positioning samples on the substrate and subsequently forming a high-resistance electrical seal, (3) an activation system (such as a computer-controlled pulsed UV illumination module) for activating caged compounds, (4) an electronics head for applying and/or measuring voltage and/or current, and/or (5) a computer-controlled analysis system for collecting and/or analyzing data. The methods may include methods for performing high-throughput electrophysiological measurements, for example, using activatable or caged compounds to study ligand-gated ion channels and transporters, sequentially and/or simultaneously.

The systems provided by the invention may allow electrophysiological measurements to be performed more quickly and/or easily than with standard patch clamp techniques, such that thousands of single-cell electrophysiological recordings may be acquired in a single day. In particular, in contrast to standard patch clamp techniques, in which a glass pipette is used to form a high-resistance electrical seal with a biological membrane, the systems provided by the invention preferably utilize a single, small (e.g., several micron diameter) aperture in an at least substantially planar substrate to provide the sealing function. Moreover, the systems may allow cells or biological membranes to be maneuvered to the aperture by fluid flow. Thus, these systems may not only make the measurement easier, by reducing or eliminating the need for a direct human operator, a microscope, and/or a micromanipulating arm, but they also may provide a format suitable for achieving multiple electrical seals in parallel, thereby increasing the measurement throughput of the device.

The systems provided by the invention may be capable of forming high-resistance electrical seals, on the order of tens of MΩ to 1 GΩ, for example, through appropriate selection and processing of the substrate material, aperture geometry, and attention to the way in which the biological membrane interacts with the substrate. Preferred substrates include thin plastic films, in which small apertures have been photomachined using a laser. These substrates optionally may be vacuum deposited with thin layers of glass to aid in the formation of the high-resistance seal. Additional, suitable substrates may include silicon wafers, in which small apertures have been produced using standard photolithographic/wet etching techniques. In any case, individual cells may be positioned onto isolated apertures using a suitable positioning method, such as differential pressure.

The system and aspects thereof are described below in more detail, including, among others, (I) single-sample measurement chambers, (II) preferred substrate/aperture geometries, (III) high-throughput measurement systems, (IV) channel/transporter assays, and (V) examples.

I. Single-Sample Measurement Chambers

Figure 2:
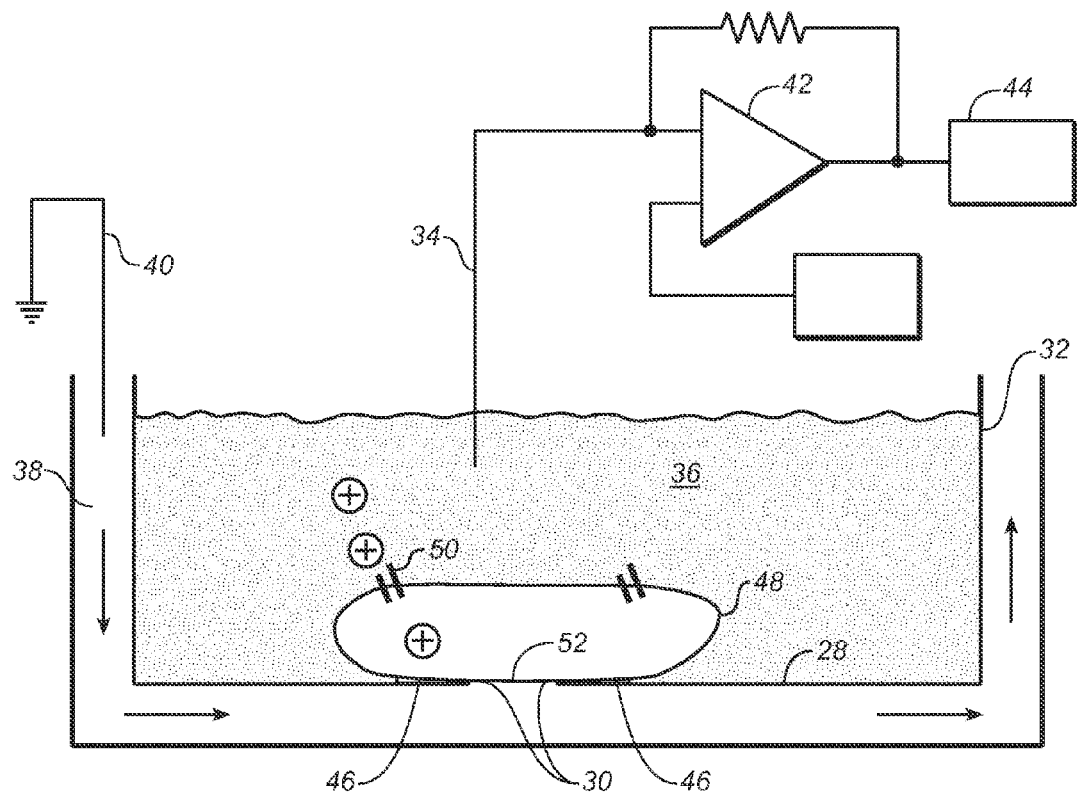
FIG. 2 is a schematic view of the formation of an electrical seal between a single cell and a single hole in a substrate, in accordance with aspects of the invention.

FIG. 2 depicts a measurement geometry with for a single measurement chamber, in accordance with aspects of the invention. Starting with a thin (<25 μm thickness) substrate 28, a single hole 30 (~1 to 3 μm diameter) is formed in the bottom of a chamber 32. An electrical circuit is implemented through the use of a Ag/AgCl sensing electrode 34 in contact with an ionic saline solution 36. A second isolated fluid chamber 38 allows fluid access to a bottom side of hole 30 in conjunction with a bath electrode 40, thereby completing the measurement circuit. The current flowing in the circuit is sensed by a high-impedance operational amplifier 42 and recorded by a computer controlled data acquisition system 44.

An important aspect of the invention is the ability to form a high-resistance electrical seal 46 between the surface of substrate 28 and a biological membrane 48 without micromanipulation by a skilled technician. To achieve this, the sample such as a cell containing the membrane is placed in suspension in top chamber 36, and drawn to hole 30 through the use of differential pressure applied between bottom chamber 38 and top chamber 36. It has been found and demonstrated that once a cell reaches a properly chosen and engineered substrate, an electrical seal of tens of MΩ to greater than 1 GΩ is achievable. Given this high seal resistance level, it is then possible to isolate and measure typical physiological whole cell currents (>50 pA) that occur when the ion channels in the cell membrane are activated. The high electrical resistance seal also allows for the ability to control the voltage of the cell, a very useful feature in analyzing ion channel activity.

To achieve voltage clamp of the membrane, an electrode must be placed in electrical contact with the inside of the cell. This requires electrically permeabilizing the part of the cell membrane 52 separating the two fluid chambers. This permeabilization has been effected in the present device in two ways: (1) voltage pulses ("zapping") generated by electrodes 34 and 40; and (2) flowing proper concentrations of antibiotics (Nystatin or Amphotericin B) in bottom chamber 38. There also are many other types of chemicals (e.g., gramicidin, ATP, valinomycin, etc.) that could be used to provide electrical access to the cell interior.

II. Preferred Substrate/Aperture Geometries

The apparatus may be used with any suitable cell, organelle, vesicle, or other membrane system. Exemplary mammalian cell lines of interest in ion channel expression systems include Chinese Hamster Ovary (CHO) cells and Human Embryo Kidney (HEK) cells. These cells have mean diameters in the range of 10-20 μm. Optimum hole size in the substrate is governed by several considerations. Holes that are too large can allow cells to pass through the hole (as opposed to sealing) when differential pressure is applied. In addition, holes that are too large can impede formation of higher seal resistances. On the other hand, holes that are too small can produce a higher electrical access resistance to the interior of the cell once an electrical seal is formed. This higher access resistance degrades the time resolution and voltage control performance of the system. Given these trade-offs, a preferred implementation features hole diameters in the range of 1-3 μm, although a wider range of hole diameters (e.g., 1-10 μm) is feasible depending on cell type.

Given that the preferred hole diameter is on the order of a few micrometers, it is preferable that the unperforated substrate be thin (e.g., <25 μm), at least near the hole periphery. The reasons for this are several. Thick substrates introduce the problem of a very narrow pore relative to the substrate thickness, which in turn makes it more difficult to achieve fluid access to the membrane. Fluid contact is necessary to provide an electrical pathway to measure ion channel currents, as well as to provide the cell with a normal physiological environment. Also, when attempting to gain electrical access to the interior of the cell, a long narrow channel derived from using a thicker substrate will produce a higher electrical access resistance than that provided by a thinner substrate. As mentioned previously, a higher access resistance degrades system time resolution and the ability to voltage clamp the cell. In addition, any technique to machine the hole in the substrate is more difficult, time consuming, and costly when starting with a thicker substrate. As such, substrate materials utilized in these embodiments preferably had a thickness of less than 25 µm in their entirety or at least near the periphery of the hole.

Accordingly, an important consideration of this invention is in the choice of the substrate used, the manner in which the substrate is processed to form the hole and the specific geometry utilized to make the concept workable in a high-throughput instrument. With regards to the choice and manufacture of the substrate, two specific embodiments of the device have been demonstrated in our laboratory.

II.A Substrate Embodiment 1—Thin Plastic Films

In one embodiment, thin plastic films were used as a substrate. Two types of thin films were tested, polyethylene terephthalate (PET) (Dupont Mylar) and polyimide (Dupont Kapton), although in principle any thin plastic film (e.g., polycarbonate, polypropylene, polyethylene, etc.) may be used. The small 1-3 µm diameter holes then were photomachined into the plastic film using one of two exemplary processes, although more generally any suitable process may be used.

Holes were photomachined using a pulsed YAG laser operating at 355 nm. In this arrangement, a single laser beam drills an isolated hole, one at a time. This beam is then scanned, typically using a galvanometric mirror scanning system to raster scan the incident beam over the substrate creating an array of photo-machined holes. Such systems often employ an F-Theta lens system, which focuses as well as redirects the scanned laser beam so that the beam remains perpendicular to the target. The throughput of the scanning arrangement thus is governed by the time to drill one hole and the speed of the optical scanner. It also is possible to produce an array of holes by scanning the film or substrate (instead of the incident beam) and leaving the optical illumination system fixed. Again, the throughput of this type of system is determined by the speed of the scanning system and the time to drill a single hole.

Holes also were photomachined using an excimer laser operating at 248 nm. In this arrangement, a photo-mask is imaged onto the substrate, and the surface is ablated where the unmasked optical energy is allowed to pass through to the substrate. Using a proper mask design, the excimer imaging process can machine single or multiple holes in the substrate simultaneously depending on the mask configuration. Typically, a table scanning system is then used to move the substrate to create a larger two-dimensional pattern of photo-machined holes.

In one implementation, after the photo-machining process, the substrates were cleaned and subjected to a physical vapor deposition (PVD) of a silicon oxide $SiO_2$ coating using an RF sputtering process. The process involved pumping the system down to $~4\times10^{-6}$ torr using a cryo-pump, and subsequently backfilling the chamber with 7 mtorr of Argon. The high RF field generated between two electrode plates then interacts with the Argon to produce an ion bombardment of a $SiO_2$ target. The dislodged $SiO_2$ then is deposited onto the thin plastic film that is placed on a rotating platter running at 20 rpm. All operations are run at room temperature. Coating thicknesses implemented were in the range of 500 to 1000 angstroms.

It was determined experimentally that the $SiO_2$ coating of the plastic film significantly enhanced the electrical sealing properties between the substrate and the cell membrane, increasing the seal resistance from tens to hundreds of MΩ for the bare plastic film to resistances on the order of 1 GΩ with the deposited glass coating. Other implementations of the coating process may be possible, such as using different thicknesses, different constituents (e.g., boron doped), and different deposition techniques (e.g., chemical vapor deposition). The specific implementation described here should not limit the scope of the invention.

Figure 3:
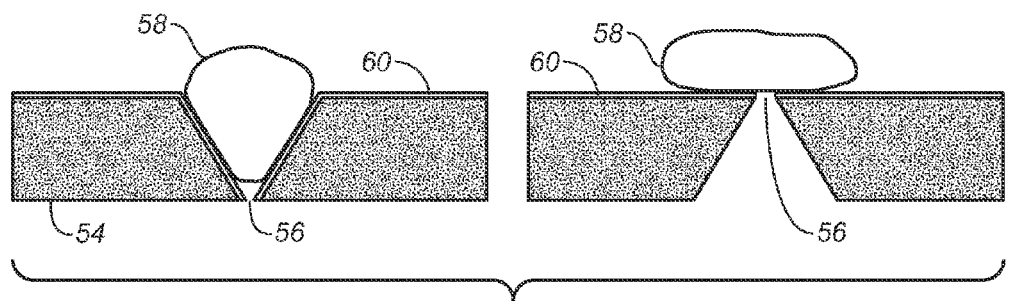
FIG. 3 is a schematic view of aperture geometry, showing two configurations for seal formation, in accordance with aspects of the invention.

FIG. 3 depicts two separate examples of a cell 58 positioned over a hole 56 in a thin layer substrate 54. As shown, due to the nature of the photomachining process, the holes are larger on one side than the other; the diameter on the smaller side of the pore is in the range of 1-3 µm. In each of these cases, a $SiO_2$ coating 60 is applied to the cell-side surface to improve seal formation. Both geometries have proven to be viable in achieving good electrical resistance between the cell membrane and the substrate.

Figure 4A:
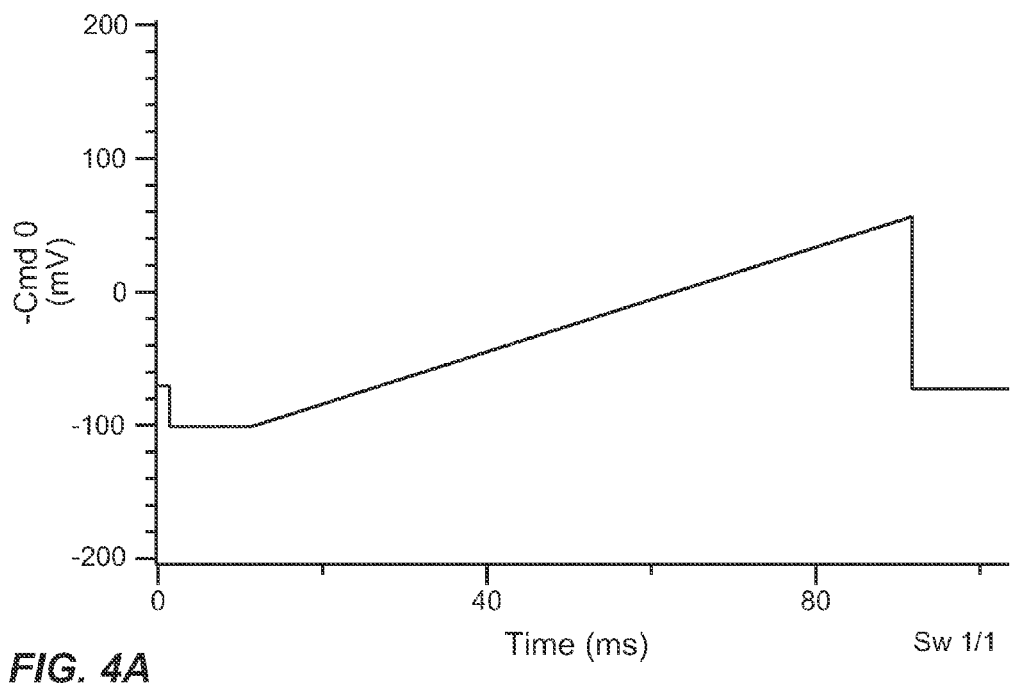
FIG. 4 is a graph showing command voltage protocol and measured electrical leak resistance between a transfected CHO cell and a $SiO_2$-coated Kapton-film aperture.
Figure 4B:
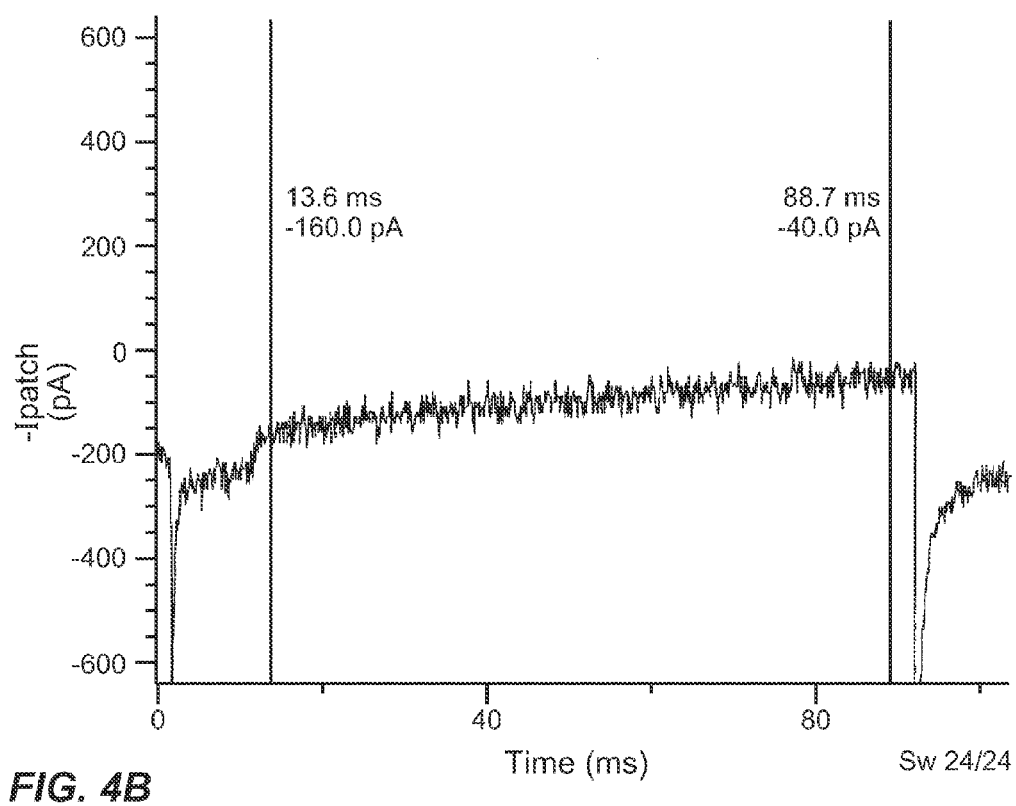
Figure 5A:
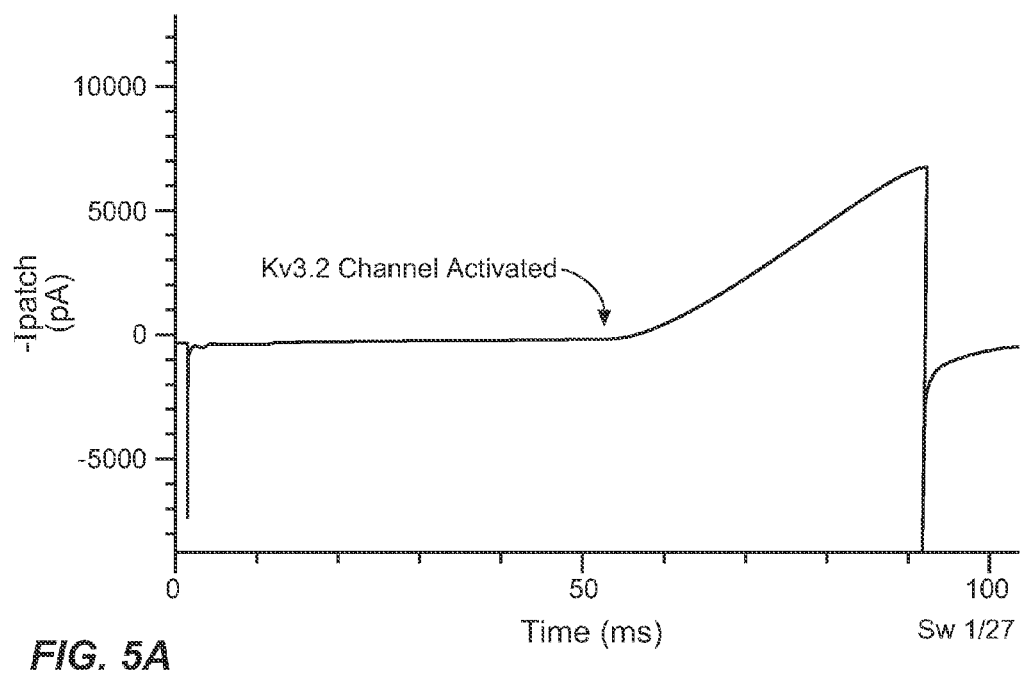
FIG. 5 is a graph showing whole cell physiological currents measured on CHO cells transfected with the voltage-gated potassium channel Kv3.2, for a voltage sweep from −100 mV to +60 mV, and for a voltage step protocol from −70 mV to various step voltages.
Figure 5B:
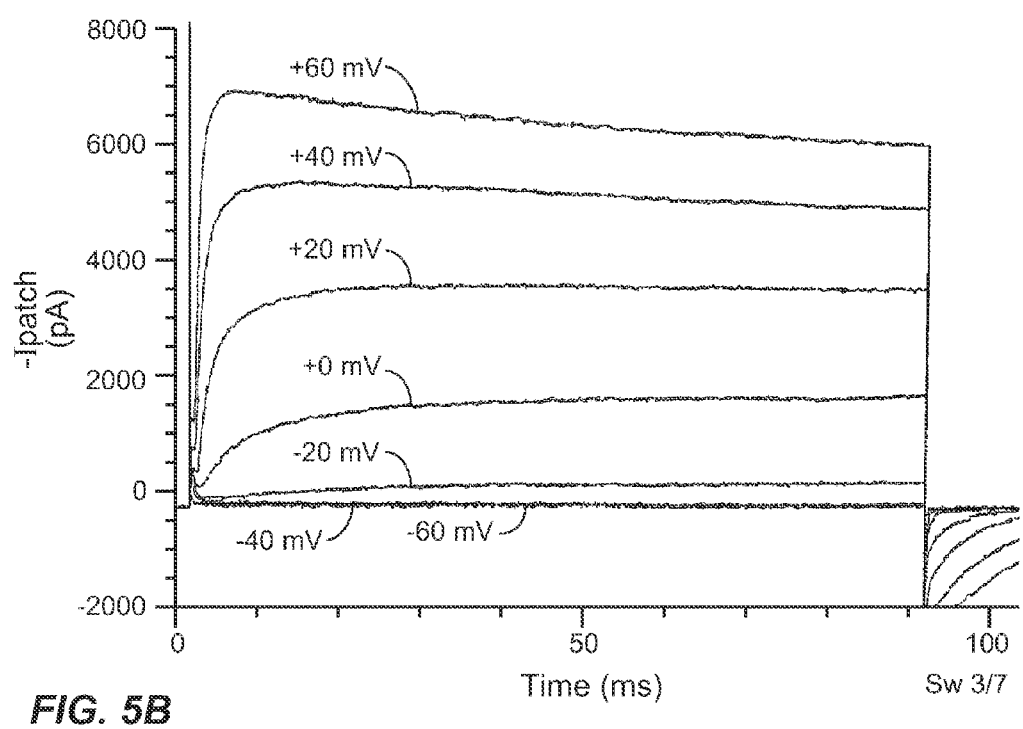

FIGS. 4 and 5 demonstrate typical whole-cell electrophysiological data acquired on CHO cells transfected with the voltage gated potassium channels Kv3.2. In this case the substrate material was Kapton, the hole was photomachined with an excimer laser (~3 µm diameter), and the resultant substrate was coated with a 500 angstrom $SiO_2$ coating. The cell was positioned onto the hole in the substrate using differential pressure of approximately 5 inches of $H_2O$. After contacting the membrane, a seal resistance of approximately 1.3 GΩ was measured.

FIG. 4 contains two data graphs relating to measured electrical leak resistance between a transfected CHO cell and a $SiO_2$ coated Kapton® polyimide film membrane pore. The top graph represents the applied command voltage placed on the measurement electrode. As shown, the voltage sweeps from −100 mV to +60 mV (range of 160 mV) over approximately a 90-msec time course. The bottom graph represents measured current after the electrical seal was formed. As shown. the current over the same time course increased approximately 120 pA. Since the resistance of the cell membrane itself without ion channel activation is on the order of 10 GΩ, the measured current in this example is primarily due to leak resistance. The leak resistance, which is a measure of the electrical seal between cell membrane and the substrate, is computed from the data as (160 mV/120 pA)=1.3 GΩ.

To demonstrate voltage control of the cell and physiological currents, the whole-cell configuration was implemented using the antibiotic amphotericin B to chemically permeabilize the part of the membrane covering the hole. This was accomplished by flowing amphotericin B at a concentration of 200 µg/ml to the underneath side of the hole. The mode of action of this compound is then to partition into cell membranes, where it interacts with cholesterol to form tiny channels permeable to monovalent ions. This provides a low-resistance electrical access to the interior of the cell and in turn allows for control of the transmembrane voltage over the remaining unpermeabilized cell membrane.

FIG. 5 contains two data graphs relating to the physiological measurement of the Kv3.2 channel activity after the application of amphotericin B and under "whole cell" conditions. The top graph represents the applied voltage sweep, which ranged from −100 mV to +60 mV (same sweep as that of FIG. 4), providing a measure of the voltage activity of the channel. As shown, there is practically no current present until approximately 50 msec into the sweep (transmembrane voltage of −10 mV), at which time the potassium channels open and a positive current (out of the cell) is recorded. The bottom graph represents measured current generated by channel activity, where the voltage clamp was stepped sequentially for 90 msec intervals from a resting potential of −70 mV to the different respective voltages labeled on the graph. As shown, for this particular channel, current is slightly activated at a membrane potential of −20 mV, and is greatly activated at more positive potentials.

Although the data represented in FIGS. 4 and 5 was gathered from a single cell on a single hole, the substrate, processing, and experimental method utilized is entirely amenable to one where multiple cells could be measured in a parallel architecture.

II.B Substrate Embodiment 2—Silicon Wafers

In another embodiment, standard solid-state process techniques to produce a perforated membrane substrate. The processing started with <100> p-type silicon wafers that had been polished on both sides. After cleaning, a 4000 Å layer of silicone oxide ($SiO_2$) was thermally grown on both sides of the wafer. This layer then was followed by a 2000 Å layer of silicon nitride ($Si_3O_4$) and a second 4000 Å layer of $SiO_2$, each of which was deposited using LPCVD on both sides. The front side of the wafer then was patterned with photoresist to allow for the removal of a 1 mm square section of all three oxide layers through Reactive Ion Etching (RIE). The back side of the wafer then was patterned to allow for the removal of a coincident 4 µm diameter section of the oxides, again through a reactive ion etch.

After stripping and cleaning, an anisotropic wet etch was performed in EDP to produce a pyramidal shaped hole from the front side of the wafer (1 mm square) to the oxide layers on the back side of the wafer. This resulted in a 1-µm thick, 300-µm square membrane of oxides with a 4-µm diameter hole in the center. This process may be extended to produce wafer substrates exhibiting 1 or 2-dimensional patterns of hundreds to thousands of holes. Individual cells then were positioned onto the individual etched holes using differential pressure, as described previously.

III. High-throughput Measurement System Description

This section describes systems for conducting electrophysiological measurements, serially and/or simultaneously, on a plurality of samples. These systems may include (A) a multiaperture substrate, (B) a plenum fluidics system (C) a plenum vacuum regulation system, (D) a sample handling/fluidics system, (E) an electronics/measurement system, (F) an activation system, and/or (G) a controller system, among others.

III.A System Overview

Figure 6:
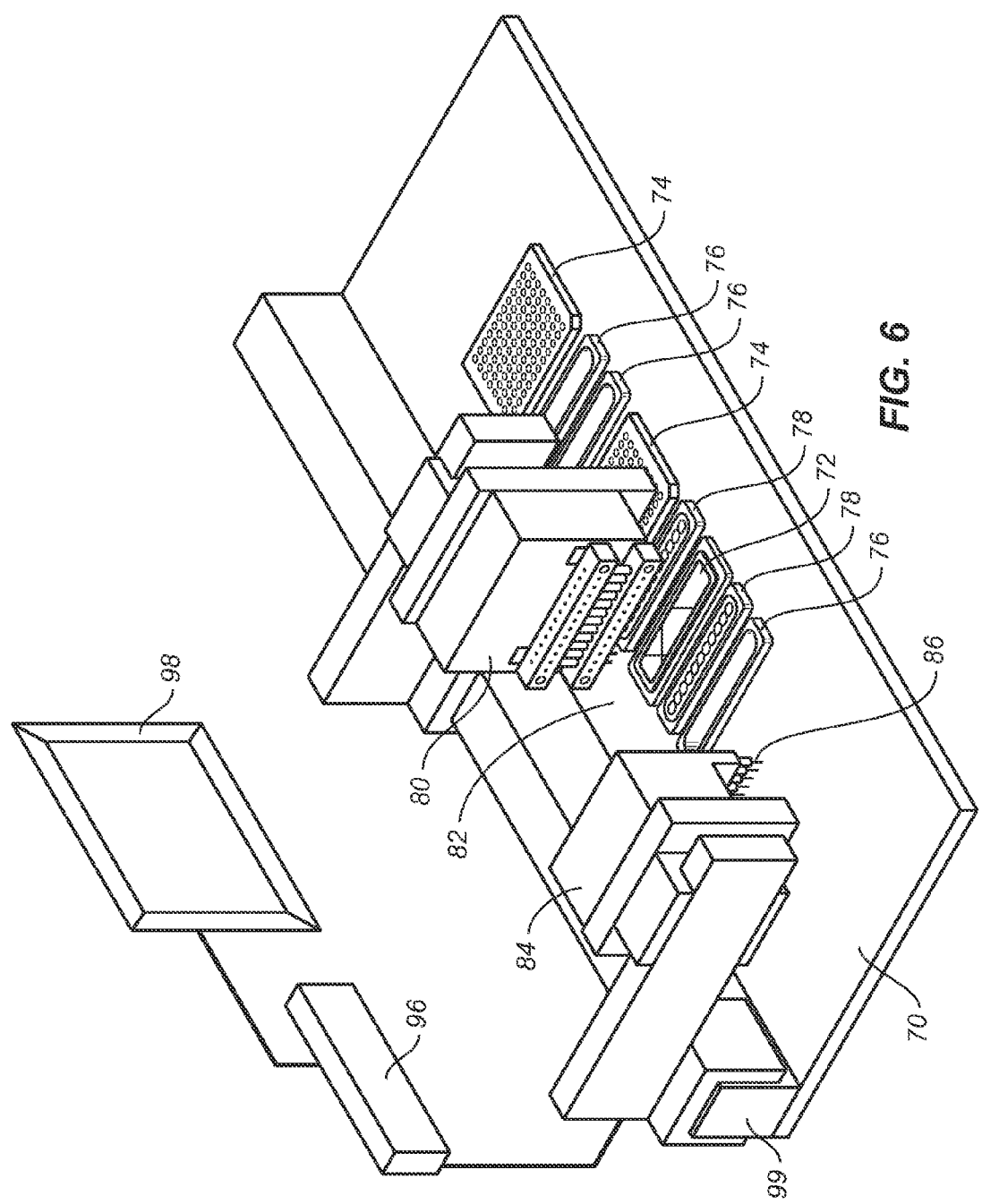
FIG. 6 is a partially schematic view of an exemplary system platform layout for conducting high-throughput electrophysiological measurements, in accordance with aspects of the invention.

FIG. 6 shows an exemplary multiaperture system, adapted to conduct simultaneous measurements on a plurality (e.g., an n×m grid) of samples, in accordance with aspects of the invention. This system includes a measurement platform 70 for supporting various components of the system. These components include a plurality of function stations, including an analysis station 72 and one or more input stations 74, renewal stations 76, and/or cleaning stations 78, among others. These components also include a sample handling fluidics head 80 having a plurality of dispense elements 82, an electronics head 84 having a plurality of electrodes 86.

The multiaperture system of FIG. 6 may be controlled via any suitable method, such as an external microcomputer 96, CRT display 98, and software user interface. The system further may incorporate an embedded microcontroller, interfaced to the external microcomputer, for controlling real-time functional aspects of the instrument, including motion control, fluidics control, and electrical data recording.

The controller further may be interfaced with a three-dimensional mechanical gantry system 99 capable of independently moving the fluidics head (80) and the electronics head (84). The fluidics and electronics heads may, without loss of function, independently comprise single probes, n×1 (1-dimensional) probes, as shown here, or n×m (2-dimensional) probes. Thus, the combination of the controller and gantry systems allows for the spatially selectable transfer of potential drug candidates to the various n×m "wells" of the multi-well measurement substrate using the fluidics head, the spatially selectable activation of caged compounds, and/or the spatially selectable electrical recording from samples using the electronics head.

The system components, most generally, be configured for independent and/or coordinated movement, with the individual components (or portions thereof) moveable and/or fixed, as desired, consistent with an ability to bring components into registration or alignment as needed for particular functions. For example, the fluidics head and a sample holder may be brought into register by moving the fluidics head, the sample holder, or both, using any suitable registration device or mechanism.

III.B Measurement Platform

The measurement platform generally comprises any mechanism such as a planar surface for supporting and/or maintaining the spatial arrangement between some or all of the components of the measurement system.

Figure 7:
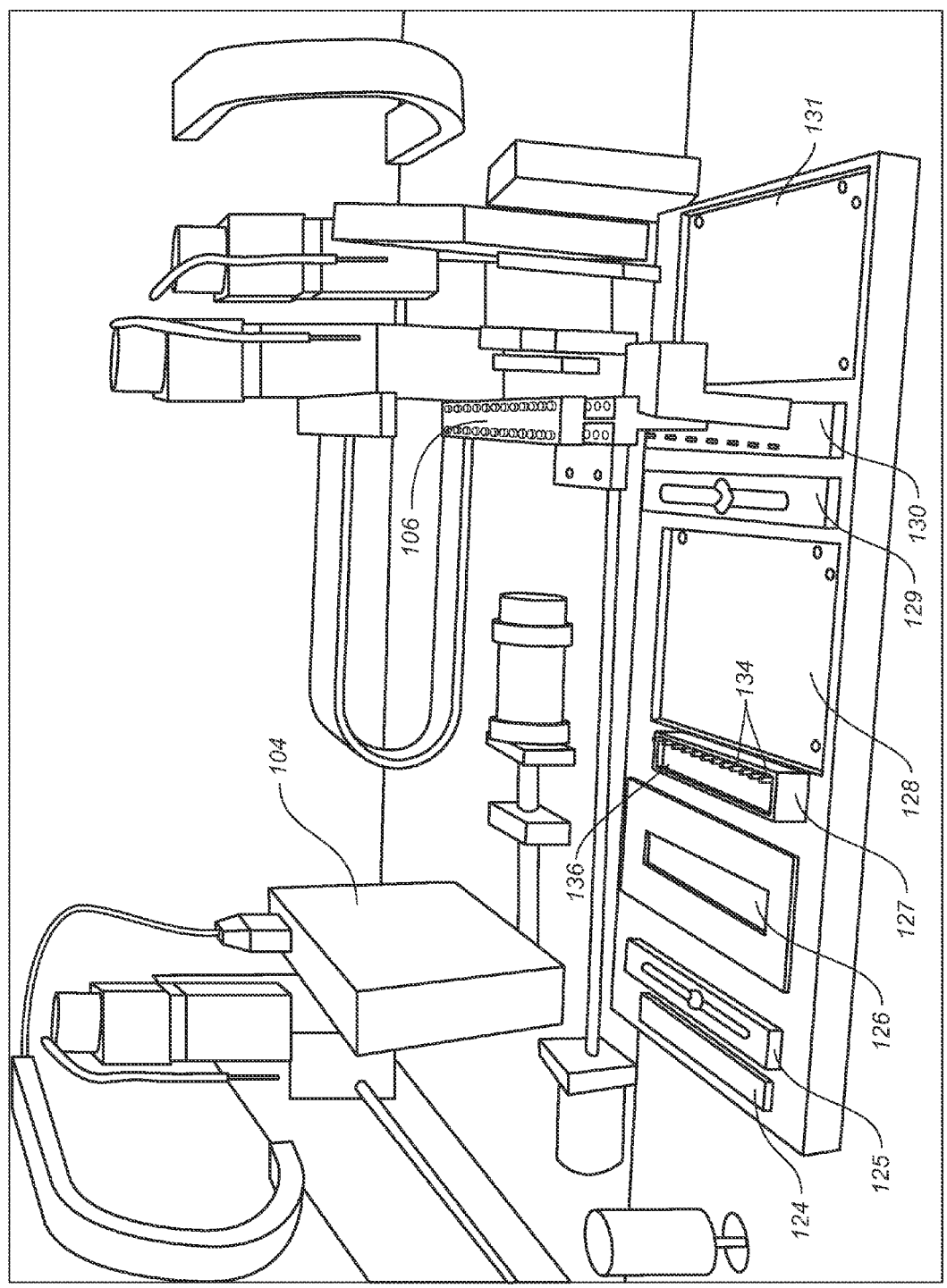
FIG. 7 is a picture of the system platform layout of FIG. 6, showing additional features of the layout.
Figure 8:
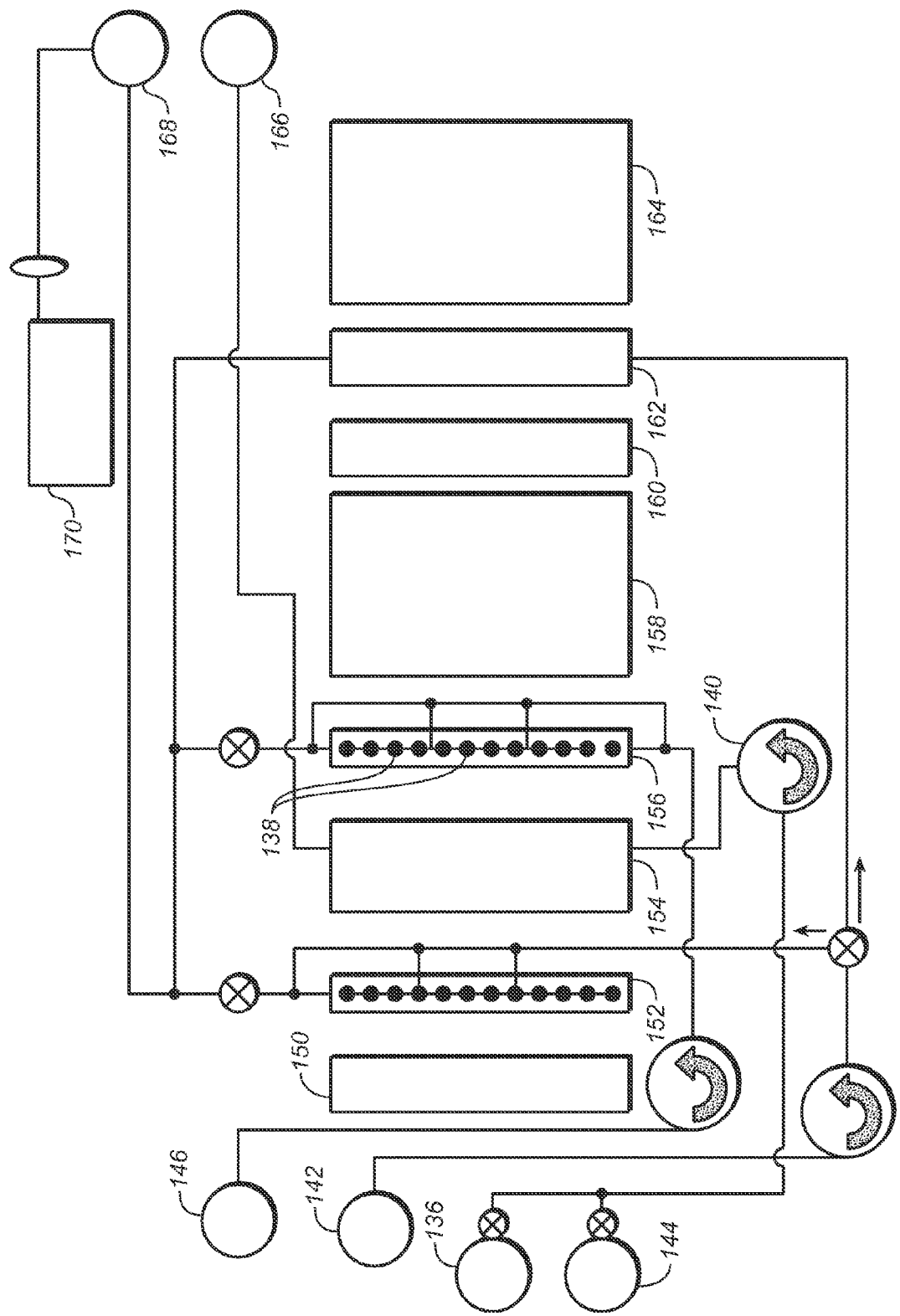
FIG. 8 is an alternative schematic view of the system platform layout of FIG. 6, showing additional features of the layout.

FIG. 7 is a top side view of one implementation of the measurement platform for use in high-throughput electrophysiological measurements, in accordance with aspects of the invention. This layout includes eight separate linearly disposed fixture positions 124-131. The electrical sensing head (104) can access three positions (124-126), the multi-channel dispensing head (106) can access six positions (126-131), and both heads can access one position (126). More generally, the system platform layout may include any suitable number of positions, for any suitable functions, disposed and accessed in any suitable manner.

Position 126 is an analysis station, referred to as the plenum, which in turn is used to support the individual measurement substrates containing samples. This position may be accessed by the multi-channel dispensing head, to dispense samples, screening compounds, and the like, and by the electrical sensing head, to make electrophysiological measurements. The plenum system reservoir creates an air-tight seal by locking the measurement substrate into position atop the plenum using a vacuum-induced differential pressure between the measurement substrate carrier and an o-ring situated on the plenum. This air-tight seal allows fluid in the plenum reservoir to be maintained at slightly less than atmospheric pressure, thereby introducing a differential pressure across the membrane that forces fluid from the top chamber through the individual apertures into the common lower reservoir. The resulting flow pulls individual suspended cells (or cell membranes) in multi-well compartments down onto the individual apertures in parallel, without direct human intervention. In addition, once the cells contact the membrane surface, the continued use of differential pressure enhances the formation of high-resistance electrical seals between the substrate material and the cell membrane.

Positions 128 and 131 are input stations, from which potential biological screening compounds may be obtained. The footprint for these positions preferably is compatible with 96, 384, and/or 1536-well microplates, as these are common receptacles for potential drug candidates (agonists or antagonists) used by the pharmaceutical industry.

Position 130 is another input station, from which extracellular fluid may be obtained. This fluid preferably comprises a physiological saline solution for transfer by the fluidics head to the top side of the measurement substrate at position 126. The station may include a removable boat that holds the saline solution; alternatively, or in addition, the station may be automated by priming it for automatic fill and drain via a peristaltic pump and a vacuum-assisted waste bottle.

Position 129 is yet another input station, from which cells or other biological samples may be obtained. This station also may include a removable boat that contains cells or other user-prepared biological material in suspension for transfer by the multi-channel fluidics head to the top side of the measurement substrate. Cellular samples may be maintained as a slurry, for example, with cell densities on the order of about $10^6$ cells/ml. The volume of cell slurry required for an experiment depends on the number of wells used in the experiment and on the volume of fluid dispensed into each well; for 384 wells, with 3-4 µl dispenses, the volume of slurry required is less than about 1.5 ml.

Position 124 is a renewal station for replenishing the chloride coating of the electrodes. This station may include a removable boat that contains a solution (commonly bleach) for depositing chloride on the sensing pins of the multi-channel electrical read head. More generally, the station may include any apparatus or material suitable for maintaining, replenishing, and/or rejuvenating the electrodes.

Positions 125 and 127 are cleaning or wash stations for the electrical head and the multi-channel fluidics head, respectively. The electrical and fluidics heads should be cleaned whenever they come into contact with potentially biologically active test compounds, to reduce or prevent carryover that may affect future measurements. The two cleaning stations each include a manifold of input ports that preferably matches the dimensionality of the associated electronics or fluidics head, or a portion thereof (here, both 12 channels). The two stations employ a design whereby cleaning fluid is pumped using a peristaltic pump from a source bottle through individual access ports 134 to overflow into a respective catch basins 136. The stations may use any suitable cleaning solution to clean both the sensing pins from the electrical head and the dispense elements of the multi-channel fluidics head, for example, water and a cleaning solvent such as 10% ethanol for the fluidics head and a saline solution for the electronics head. The inside of the needles from the fluidics head may be washed by performing fast aspirate/dispense cycles in association with flowing fluid through the individual wash input ports 134. Compartmentalizing the individual wash ports reduces wash volume and the potential for well-to-well contamination. It also forces fluid around the outside of the individual dispense needles of the fluidics head. The waste basins drains directly into a vacuum-assisted waste bottle. The close proximity of the wash stations (125 and 127) to the analysis chamber (126) reduces overall assay time by reducing the distance the respective electronics head (104) and fluidics head (106) must travel in performing repetitive and time-consuming washing steps during biological assay protocols.

The input fluids typically include two saline solutions, at least for general electrophysiological experiments. The first saline solution (source 136) comprises a mixture of salts that mimics the internal cytoplasm of a living cell e.g., containing high potassium. This solution (denoted "internal:" buffer) may be used on the bottom side of the plenum fixture 154, which is the side by which electrical access to the interior of the cell is achieved. This solution is analogous to the fluid inside the pipette in classical electrophysiology, and may be pumped in and out of the plenum system by a peristaltic pump 140. The second saline solution (source 142) comprises a mixture of salts that mimics the extracellular solution, e.g., containing low concentrations of potassium. This solution (denoted "external" buffer) may be used on the top side of the measurement substrate, and may be added by the multi-channel fluidics head to the separate wells of the measurement substrate by accessing at position 162 and dispensing into the top side of the multi-well carrier at position 154. In operation, the constituents of both the internal and external saline solutions may vary greatly, as is common in classical electrophysiology.

The input fluids also typically include a perforation solution (source 144), which can be accessed by the plenum pump 140 through proper valve actuation. This causes the perforation solution to flow into contact with the bottom side of the membrane substrate and thus to the biological membrane. Through chemical permeation, this solution serves to provide a low-resistance electrical pathway to the interior of the cell membrane. The perforation solution preferably comprises an "internal" (high potassium) saline solution, mixed with an appropriate concentration of a chemical that subsequently provides a low electrical resistance access to the cell. This chemical may include, among others, amphotericin B, nystatin, gramicidin D, paradaxin, ATP, and so forth. The system may replace the initial plenum solution 136 with this new solution 144 using the plenum peristaltic pump 140. Preferably, the fluid in the lower chamber of the plenum may be exchanged without introducing significant pressure pulsation or static pressure changes that could disrupt the process of high-resistance seal formation between the biological membrane and the multi-well substrate. During plenum fluid exchange, or at the end of the experiment, the expelled plenum solution is pumped out to a separate waste container 166 using pump 140.

This example shows only two plenum input solutions 136, 144; however, in practice, it is possible to include as many input solutions as necessary or desired. The ability to exchange multiple internal solutions, i.e., the solution that has access to the inside of the cell, is not available in classical electrophysiology using a standard pipette.

Figure 9:
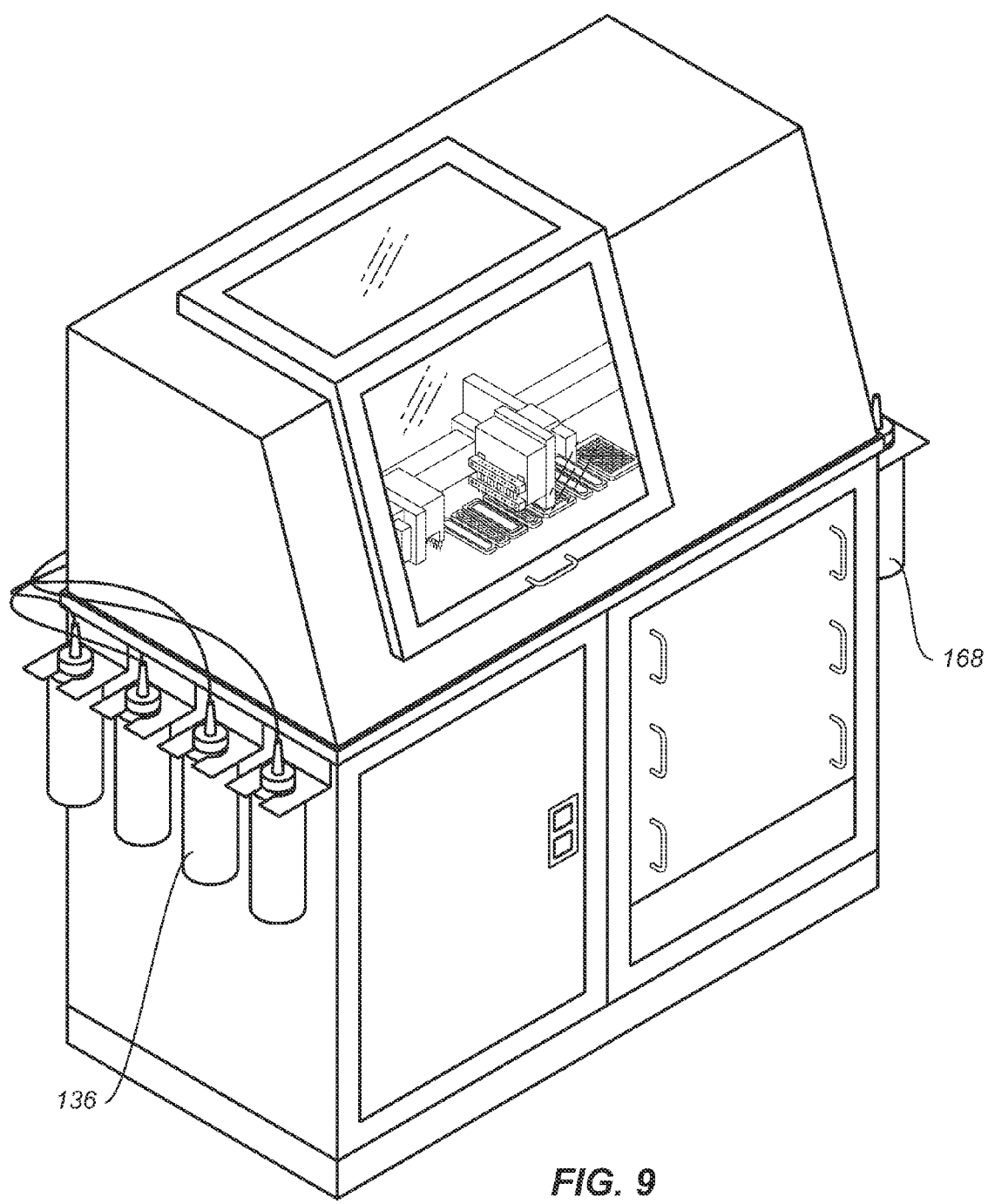
FIG. 9 is a picture of a system cabinet and bottle layout for conducting high-throughput electrophysiological measurements, in accordance with aspects of the invention.

FIG. 9 shows the location of input 136 and output 168 reservoirs, relative to an instrument housing. Here, without limitation, to facilitate use, the input fluids are located on the left side of the instrument, and the output (waste) fluids are located on the right side of the instrument layout. The system as shown includes four fluid inputs and two fluid outputs, but more generally may include as few or as many of each as necessary or desired.

III.C Multi-Well Substrate and Carrier

The multiaperture substrate generally comprises any mechanism having a plurality of holes or apertures about which a corresponding plurality of samples may be positioned and/or sealed for analysis. The substrate preferably has one aperture per sample well, although in some configurations there may be two or more apertures per sample. The substrate also preferably allows each sample to be independently exposed to reagents, candidates, and/or other materials, for example, via separate sample wells in fluid isolation from other sample wells, at least on one side of the substrate.

Figure 10:
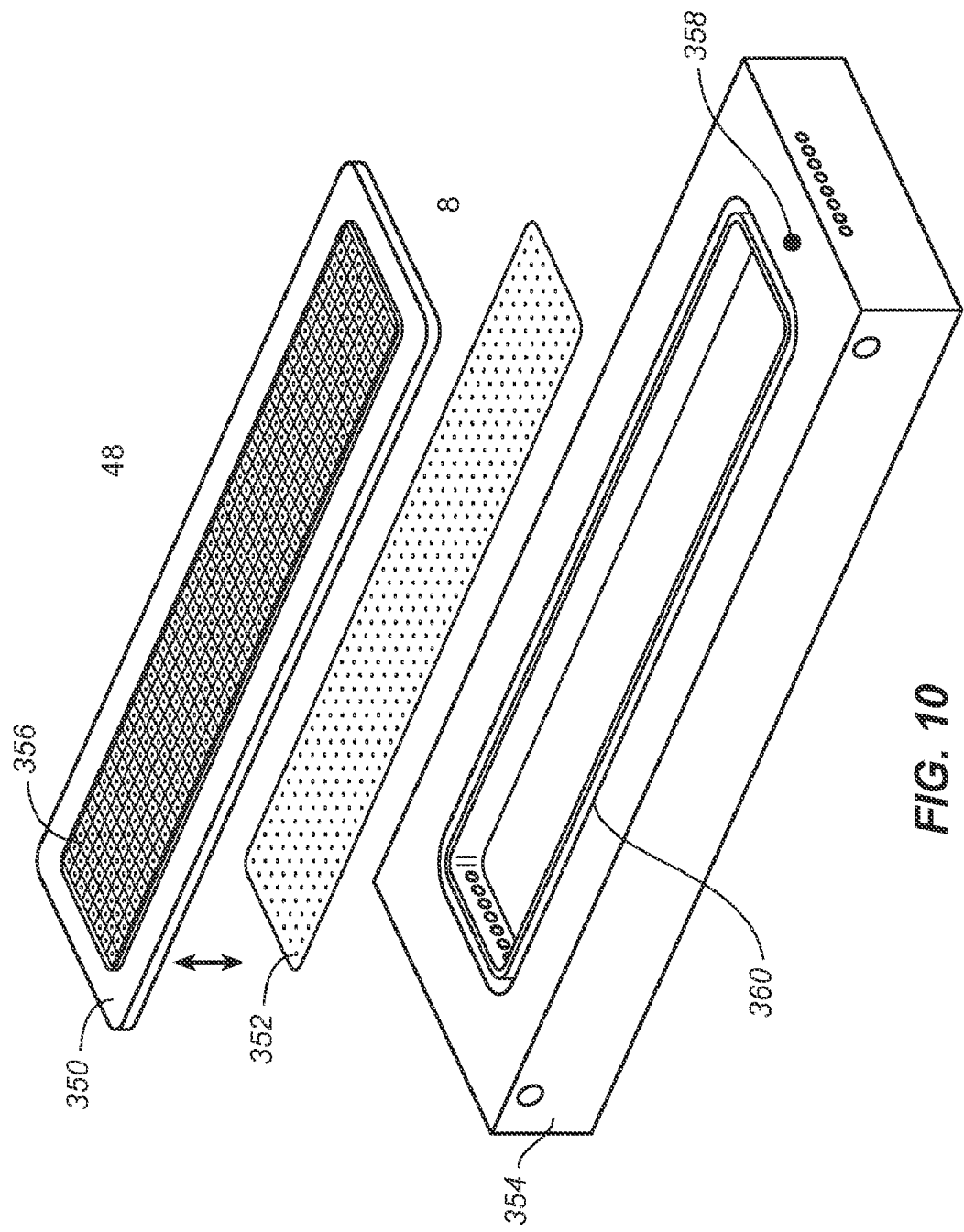
FIG. 10 is an exploded perspective view of an exemplary membrane carrier, membrane substrate, and plenum, in accordance with aspects of the invention.

FIG. 10 shows an exemplary multiaperture substrate, comprising a multi-well membrane carrier 350, a thin membrane substrate 352, and the receiving plenum fixture 354. The carrier 350 comprises the top, well-containing portion of the multiaperture substrate. The carrier may be formed of any suitable material, by any suitable process, for example, injection-molded polystyrene. The membrane substrate 352 comprises the surface and associated apertures onto which samples are sealed for analysis. This substrate also may be formed of any suitable material, by any suitable process. Typically, the substrate is formed of a thin plastic film (such as a Kapton® polyimide film or a Mylar® polyester film) that has been photo-machined (or otherwise provided) with an array of single apertures that match the geometry of the carrier, i.e., one aperture per well. The carrier and cleaned, machined membrane substrate may be joined using any suitable mechanism (e.g., by a non-toxic adhesive or ultrasonic bond), forming an electrically isolated fluid chamber 356 on top of each aperture in the membrane. For example, this bonding may be achieved by applying a layer of adhesive between the membrane and carrier, which then is cured through a combination of time, heat, and/or ultraviolet light. The assembly of carrier and membrane then forms a single substrate assembly that is assembled and packaged, preferably in a hermetically sealed pouch, in a clean room. Clean-room techniques are advantageous to reduce or eliminate foreign debris that may otherwise be introduced into the individual wells and potentially plug the small aperture at the bottom of each well during initial fluid flow.

The exemplary system described here includes a rectangular grid of 48×8 apertures that forms a 384-well substrate. The apertures have a 2.25-mm center-to-center spacing, and the well volume that is formed by the carrier and membrane holds approximately 15 µl. This geometry is only one of many that could be implemented in building such a device. For example, the illustrated design could be extrapolated to form an array of 48×32 apertures (1536) wells having a 2.25-mm spacing. The choice of center-to-center well spacing ideally should conform to a standard microplate format, so that the multi-channel fluidics head readily can access both compound plates and the membrane carrier. The industry standard microplates have 96, 384, and 1536 wells with 9, 4.5, and 2.25 mm center-to-center well spacings, respectively.

As shown in FIG. 10, upon use, the multi-well assembly is lowered into the top access of the plenum 354, where it may be clamped via a vacuum port 358 and o-ring assembly 360 located on the top surface of the plenum. The seal achieved between the o-ring and the outer rim of the membrane carrier isolates the internal chamber of the plenum. This, in turn, allows regulation and alteration of the internal plenum fluidics path at pressures slightly below atmosphere, as just described. The use of a vacuum chuck arrangement is a convenient (fast and efficient) interface for loading membrane/carrier substrates into the plenum fixture.

III.D Plenum System

The plenum system generally comprises any mechanism for adding, removing, and/or replacing fluids and associated materials from the bottom side of one or more sample wells, sequentially and/or simultaneously, while typically providing a means to control the differential pressure across the substrate. The plenum system preferably is closed, so that a differential pressure can be introduced, controlled, and/or regulated between the top side of the measurement substrate, which is at atmospheric pressure, and the bottom side of the measurement substrate, which generally is held at a slight vacuum. This differential pressure may be used, as described above, to position a cell, vesicle, and/or other sample that is in the fluid on the top side of the membrane onto the small pore(s) located in each respective well of the measurement substrate. In addition, by controlling the differential pressure very precisely, and with the appropriate timing, this pressure can be used to facilitate formation of a high resistance electrical seal between the biological membrane and the measurement substrate.

The plenum system also may be used to replace air that initially is in the system with fluids from one or more fluid inputs. This replacement is necessary to provide a continuous fluid path, which allows a complete electrical circuit to be formed between the solutions above and below the membrane. To accomplish this task, air must be removed from the various fluid pathway lines, as well as from the small aperture in the measurement substrate. Removing the air from the substrate is a difficult proposition, because the microscopic geometry of the aperture typically is a long narrow channel.

The plenum system also may be used to replace one fluid in the system with another during the measurement process, after electrical seals have formed. To do this effectively, without unduly disrupting the seal, the plenum system should be able to reduce or minimize pressure perturbations, as well as to control the differential pressure during the exchange process. These and other aspects of the plenum system are described below, including (1) the plenum fluidics subsystem, and (2) the plenum vacuum regulation subsystem.

III.D.1 Plenum Fluidics System

Figure 11:
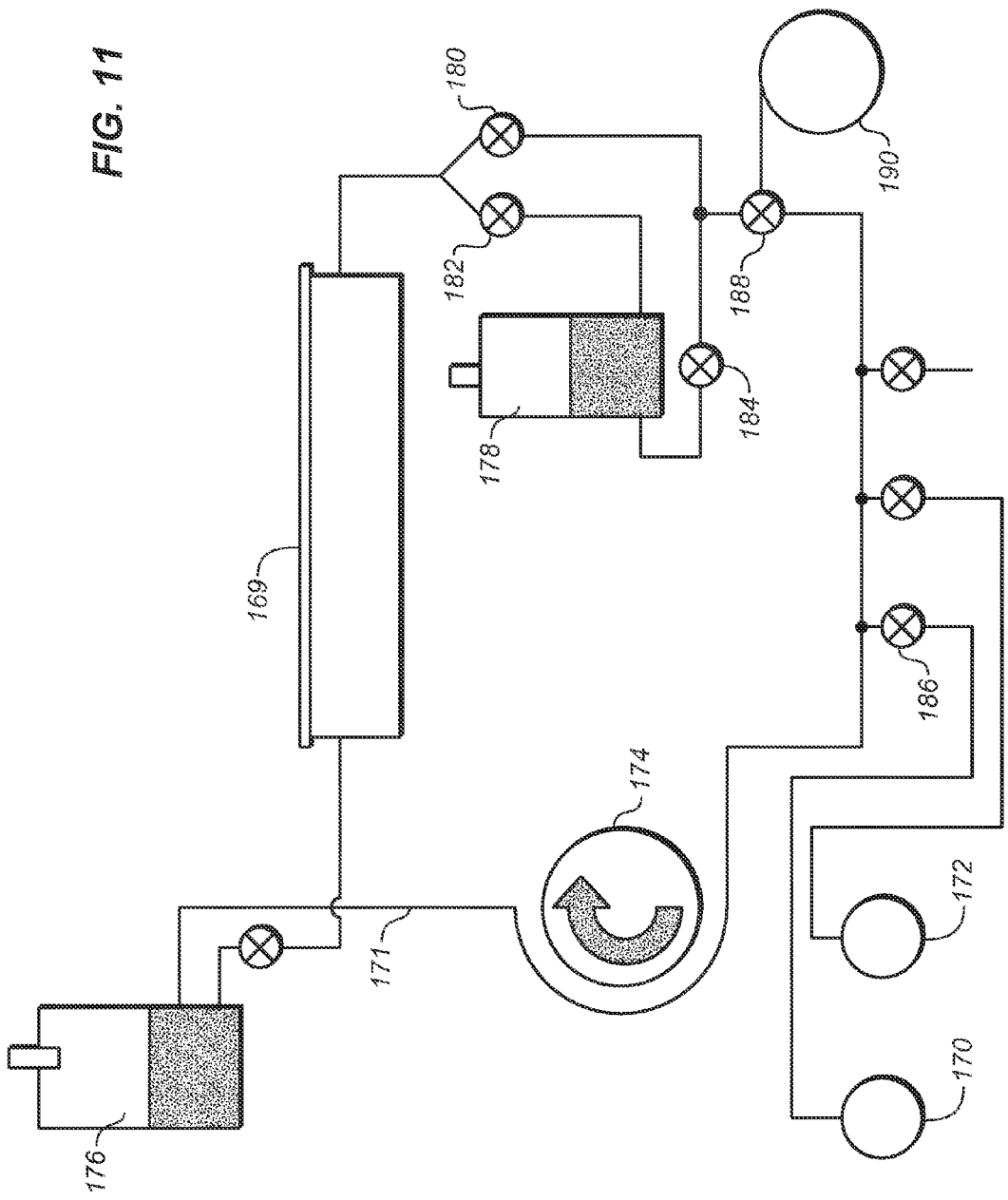
FIG. 11 is a schematic view of an exemplary plenum fluidics system, in accordance with aspects of the invention.

FIG. 11 is a schematic representation of an exemplary plenum fluidics system, in accordance with aspects of the invention. This system generally comprises any mechanism for regulating fluid access to the bottom side of the measurement substrate. The system includes a plurality of fluid pathways (solid lines 171), preferably constructed of flexible silicone tubing and pneumatic pinch valves. This arrangement allows for a stable, biologically inert pathway, which, with proper maintenance, can be kept clean, since the fluid is confined to the silicone tubing and not exposed to other valve components. The pumping action may be provided by any suitable mechanism, such as a dual, 4-roller peristaltic pump 174. This allows for the maximum pumping efficiency, while minimizing the "pulsing" of the fluid flow as the rotor turns over the tubing.

The system also includes two debubblers 176 and 178, positioned on opposite sides of the plenum (169). These debubblers have several functions. First, and foremost, they are a convenient way to remove macroscopic bubbles from the system. Specifically, as a bubble floats into the partially filled debubbler tube, the bubble will float to the top and be removed from the fluid path. Second, the debubblers also serve as convenient control points for vacuum control. Third, the debubblers also act as a capacitive reduction to kinetic perturbations in pressure introduced by the pump during fluid flow.

The system may be filled with fluid by an appropriately sequenced actuation of various valves, in combination with pump flow. To remove bubbles in the system that cling to the tubing or the plenum itself, a "pulsing" procedure may be implemented. This procedure may involve (1) running the pump at a moderate speed, (2) initiating an increase in positive pressure in the plenum by closing off the output side of the plenum at valves 180 182 and 184, and (3) relieving the increase in positive pressure by opening valve 180 temporarily. The resulting pressure pulse may clear bubbles out of the system, which fluid flow via the peristaltic pump alone typically is not sufficient to do. This debubbling is performed prior to adding cells or other samples to the system, since the pressure perturbations induced during this "priming" procedure may be too great to maintain an electrical seal between cell and membrane. The pulsing may be performed while maintaining a negative absolute differential pressure in the system, even during the pulses, ensuring flow from the top side to the bottom side, so that potentially recycled and "dirty" solution from the bottom side of the plate should not flow backwards to the topside, thereby plugging the hole.

The fluid in the system may be exchanged with other fluids, also by an appropriate use of various valves and pump flow. To exchange fluids, the plenum system may be opened at an input point, to accept new fluid, and at an exit point, to expel current fluid. For example, to replace fluid from a bottle 170, which previously has been added to the plenum, with fluid from another bottle 172, a valve 186 may be opened, and a 3-way valve 188 may be switched from the closed-loop flow position to the open-to-waste position. To reduce or eliminate pressure perturbations, and to control differential pressure during the "exchange" procedure, it often is useful to control the vacuum pressure in the waste bottle 190 and to maintain it a proper relative height to the other control points in the system.

III.D.2 Plenum Vacuum Regulation System

Figure 12:
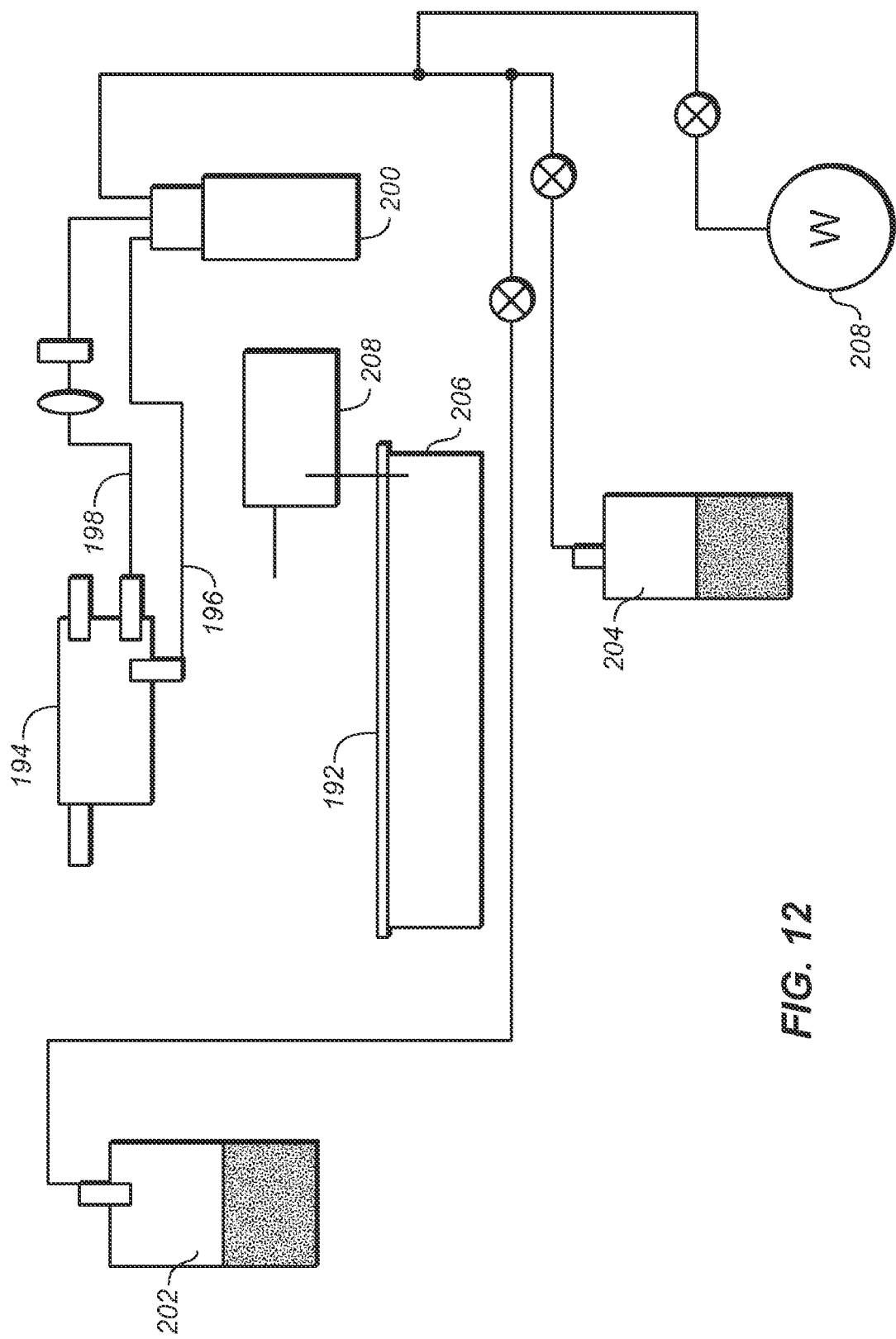
FIG. 12 is a schematic view of an exemplary plenum vacuum regulation system, in accordance with aspects of the invention.
Figure 13A:
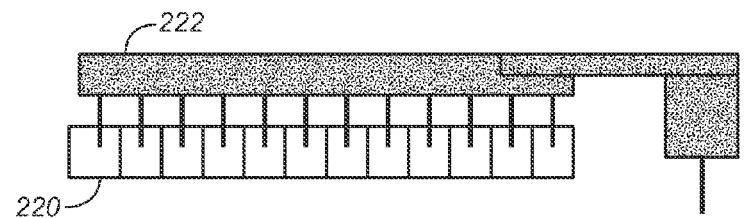
FIG. 13 is a set of views of an exemplary sample-handling fluidics head, in accordance with aspects of the invention.
Figure 13B:
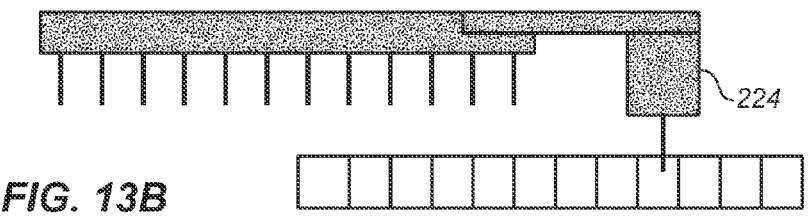
Figure 13C:
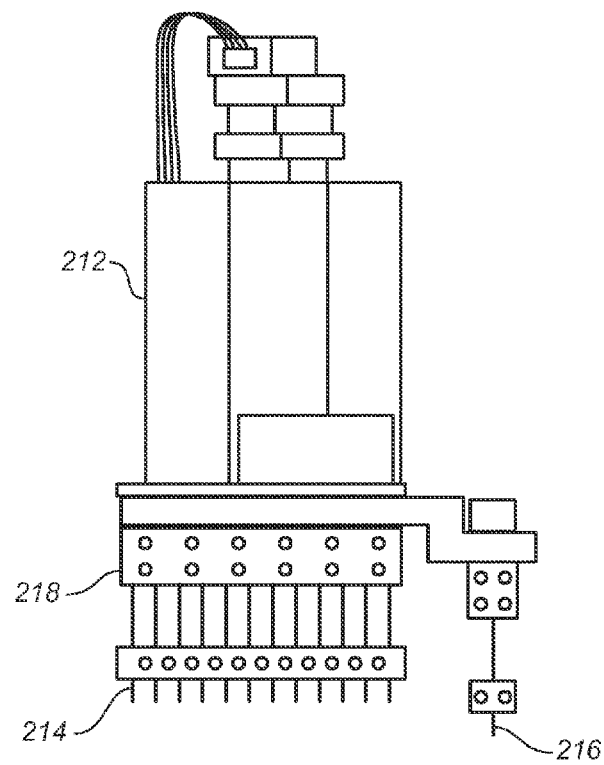

FIG. 12 is a schematic representation of an exemplary plenum vacuum regulation system. The plenum vacuum regulation system generally comprises any mechanism for controlling (e.g., maintaining, regulating, and/or monitoring) the differential pressure across the measurement substrate 192. This differential pressure generally may assume any value consistent with its intended function(s), which may include facilitating sealing of samples across the aperture and/or disrupting or destroying the portion of the sample sealed across the aperture. The differential pressure for proper high-resistance seal formation typically assumes values in a range between 0 to 10 inches of water of vacuum with respect to atmosphere, with a precision of about 0.05 inches of water. This vacuum range encompasses the range that typically is applied to the pipette during seal formation in classical electrophysiology.

The plenum vacuum regulation system may include, among others, one or more of each of the following components: (1) a vacuum (or pressure) sensor, for sensing pressure, (2) a vacuum (or pressure) regulator, for controlling vacuum, (3) a debubbler(s), for reducing or eliminating bubbles, (4) a pump, for applying pressure, (5) a line, for routing fluid between sources, sinks, the plenum, and/or other positions, and (6) an environmental sensor and/or controller, for sensing and/or controlling environmental conditions, such as temperature, pH, and the like.

The exemplary regulation system includes an electronically voltage-controlled vacuum regulator 194 for controlling the differential pressure in the plenum in the desired range. A regulated vacuum output line 196 responds to a vacuum sensing line 198 to maintain a desired vacuum level, as set by an analog voltage control. Both the regulated output line and the sense line are connected to a trap bottle 200, which serves as a protection mechanism for the sensor, as well as a form of ballast to aid the dynamics of the control system. The outputs of the regulator are fed to two debubblers 202 and 204 (as referenced in FIG. 11) in the plenum system, and to a plenum waste bottle 208, to maintain proper vacuum control points throughout the plenum system.

Control of the vacuum regulation system is made difficult by the small desired control range, typically 0 to 10 inches of water vacuum, relative to atmosphere. To facilitate control, the pre-debubbler 202 control point is located approximately 3 inches above the plenum interface, thereby providing 3 inches of water positive pressure offset (when the system is primed and filled with fluid) between the debubbler control point and the plenum 206. This provides a convenient control offset, such that the regulator works in a stable, linear range during normal operation at about 3 inches $H_2O$ of vacuum. This, in turn, allows the regulator system to control the differential pressure in the plenum accurately all the way to zero differential pressure relative to atmosphere.

The regulation system also may include a gauge or sensor 208, such as an analog gauge, that measures, in real time, the pressure differential between atmospheric pressure and the plenum. This gauge may be used for feedback to the vacuum regulator or as a quality control system monitor to indicate to the user that all systems are operational and functioning properly. For example, if the membrane substrate is not sealed properly to the plenum, thereby allowing air into the system, the gauge will provide a mechanism for determining that the system is not at the proper differential pressure and so can be used to warn the user of a potential problem.

III.E Sample-Handling Fluidics Head

The sample-handling/fluidics system generally comprises any mechanism for adding, removing, replacing, and/or transferring fluids including samples, reagents, and/or drug candidates to the top side of one or more sample wells, sequentially and/or simultaneously.

The sample handling fluidics system is configured to introduce materials independently into the respective wells of the measurement substrate, as desirable in an instrument designed for parallel simultaneous measurements. These materials may include, among others, (1) physiological saline buffer, (2) suspended cells, cell membranes, vesicles, or beads with adherent membranes, and/or (3) experimental chemical entities, for example, for the purpose of analyzing their effect on the electrophysiology of the biological membrane. The measurement fluidics system may obtain fluid from a source reservoir or multiwell plate and then dispense the same fluid in a destination reservoir, e.g., the multi-well carrier, using one or more pipette channels. Once cells are added to each well, "cell positioning" may be accomplished using any suitable method, for example, by applying differential pressure across the substrate to increase fluid flow through each aperture, as described earlier. The cells then are carried by the fluid flow to the single aperture in each well of the multi-well chamber, at which time an electrical seal can form.

The accuracy, precision, and volume specifications of the fluidics head may be selected as necessary or desired, depending on the types of samples under study, the intended throughput of the instrument, and the intended quality of the measurements. In a preferred embodiment, the fluidics head is capable of accurate (~2%) and precise (<2% CV) fluid aspiration and dispense cycles, at volumes of about 3 to 4 µl. The ability to dispense fluids with accuracy and precision is motivated by the desirability of adding known concentrations of given biologically active compounds to the sample compartments to facilitate repeatable, comparative biological assays, as well as to provide for well-to-well comparison of compound activity. The ability to dispense low volumes of fluid is motivated or necessitated by the geometry of the membrane carrier, which in the preferred embodiment has a full-well capacity of about 15 µl, and by the functional requirements of the assay, which may involve making 3-4 additions per assay.

FIG. 11 shows an exemplary fluidics head 212, in accordance with aspects of the invention. This head includes twelve (12) dispensing elements 214 and an "extra" cherry-picking dispense element 216 off to the side. Here, the dispense elements comprise stainless steel needles, coated both inside and out with Teflon® tetrafluoroethylene polymer to reduce the effects of compounds adhering to the surface of the needle and causing a carry-over problem for subsequent runs. Fluid transfer (e.g., the process of loading and/or-dispensing fluids) may be accomplished using any suitable mechanism, including contact and/or noncontact dispensing. Fluid transfer preferably is accomplished using a piston/o-ring manifold assembly 218, driven by a microstepping motor and precision lead screw assembly, that deposits fluid in individual sample compartments 220. This motor and other stepping motors in the system are disabled before making electrical measurements, to reduce noise.

The "extra" dispense element in this design covers cases in which it is necessary or desirable for the instrument to perform single channel head pipetting. For example, in the screening mode, not all individual wells of the membrane substrate will form high resistance electrical seals and provide physiologically relevant data. Moreover, individual cells or membranes may vary in their ion channel expression levels, so that not all of the biological samples will contain the ion channel of interest.

If the compounds are added to the measurement substrate quickly using a multi-channel pipettor, without regard to which wells are physiologically viable, then it is likely that some of the test compounds will not reach a physiologically viable well. The probability of such an event depends on the probabilities of the cell forming a high-resistance seal in each individual well, the cell and other components of the system allowing electrical access to the cell to clamp the voltage, the cell having the ion channel(s) of interest, and the amount of replication used in adding the test compounds, among other factors.

One approach that may increase the probability of obtaining a valid test sample is to pre-sample the wells, and then only to add test compounds to those wells that are known to be physiologically viable. The drawback of this approach is that it requires extensive pre-testing and a lot of single channel pipetting, which may greatly increase the time necessary to sample the entire multi-well substrate.

Another approach that may increase the probability of obtaining a valid test sample is to add the test compounds from a multi-channel pipettor, without regard to which wells have adequate electrical seals and physiological currents. In particular, given a reasonable percentage of well hits, the most expedient way to cover the test wells is to add the compounds systematically to "most" of the plate using the multi-channel pipettor (in duplicate or triplicate perhaps) and then to go back after the experiment with a single channel pipettor to "re-test" (after the fact) those compounds that did not have a viable data point. This type of retest strategy relies on using a single channel pipettor during the "retest" phase so as not to corrupt neighboring test wells or to waste reagents and to use the remaining "good" wells efficiently, while minimizing the amount of single-channel pipetting that must occur.

The use of the fluidics head may be illustrated by an example. Suppose that all compounds from a 96-well drug plate were added in triplicate to 288 wells (3×96) of a 384 well membrane substrate. This operation could be performed quite quickly using a multi-channel pipettor. Now, further suppose that physiological currents were measured in 50% of the wells, i.e., that there were 192 "good" wells with high resistance electrical seals and measurable physiological currents. If this success rate were distributed randomly, we would then expect $1/8$ (12) of the compounds to have 3 good measurements, $3/8$ (36) of the wells to have 2 good measurement, $3/8$ (36) of the wells to have 1 good measurement, and $1/8$ (12) of the well have 0 good measurements. In addition, there would be 96 (i.e., 384-288) virgin (i.e., unused) wells left to be tested, which at a 50% success rate would leave 48 available wells for further testing. The strategy then would be to go back and pick up each of the 12 compounds that yielded 0 valid test points on the first pass and to add them systematically to tested viable wells one at a time. This could be done as singletons, duplicates, triplicates, or the like. If desired and timely, this procedure also could continue on to the compounds that have only one good measurement until all the "good" wells were utilized. The optimum strategy, of course, depends on the hit rate (here assumed 50%) and the amount of time allotted for the assay.

The problem with this approach is that it requires two separate fluidics heads: one multi-channel and the other single-channel. This necessitates using either two sets of four-axis motion controllers (X, Y, Z, dispense), one for each head, or one four-axis motion controller, with separate, individually docked heads. The fluidics head described here may overcome both of these complexities, by attaching a separate dispense element to the assembly, offset in X, Y, and Z (height). In multi-channel operation 222, this extra dispense element clears the other fluidics positions (due to the X Y Z offset). Conversely, in single-channel operation 224, the multi-channel head does not interfere with anything on the platform, and the single tip can access any position of the measurement substrate or compound plates (due to the clearance provided by the Z offset). The advantage of this approach is its simplicity in that it avoids having a multiplicity of motion control and/or docking systems. This approach and the preferred design are extendable to other one-dimensional or two-dimensional formats, including lines and grids.

III.F Electronics Measurement System

The electronics/measurement system generally comprises any mechanism for applying and/or measuring electrical potentials and/or currents from one or more samples, in one or more sample wells, sequentially and/or simultaneously.

Figure 14:
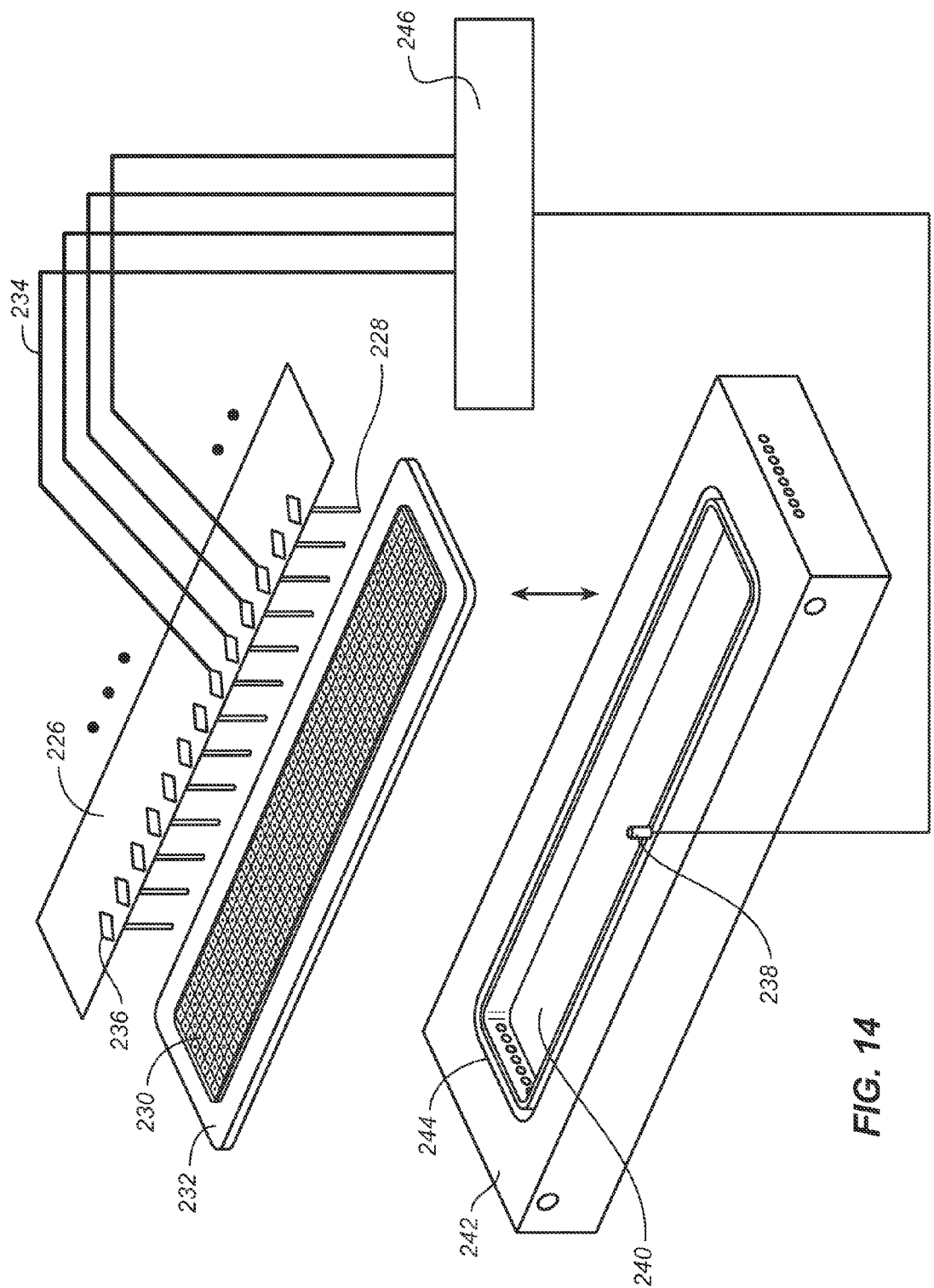
FIG. 14 is an exploded partially perspective, partially schematic view of an exemplary electronics head, in accordance with aspects of the invention.
Figure 15:
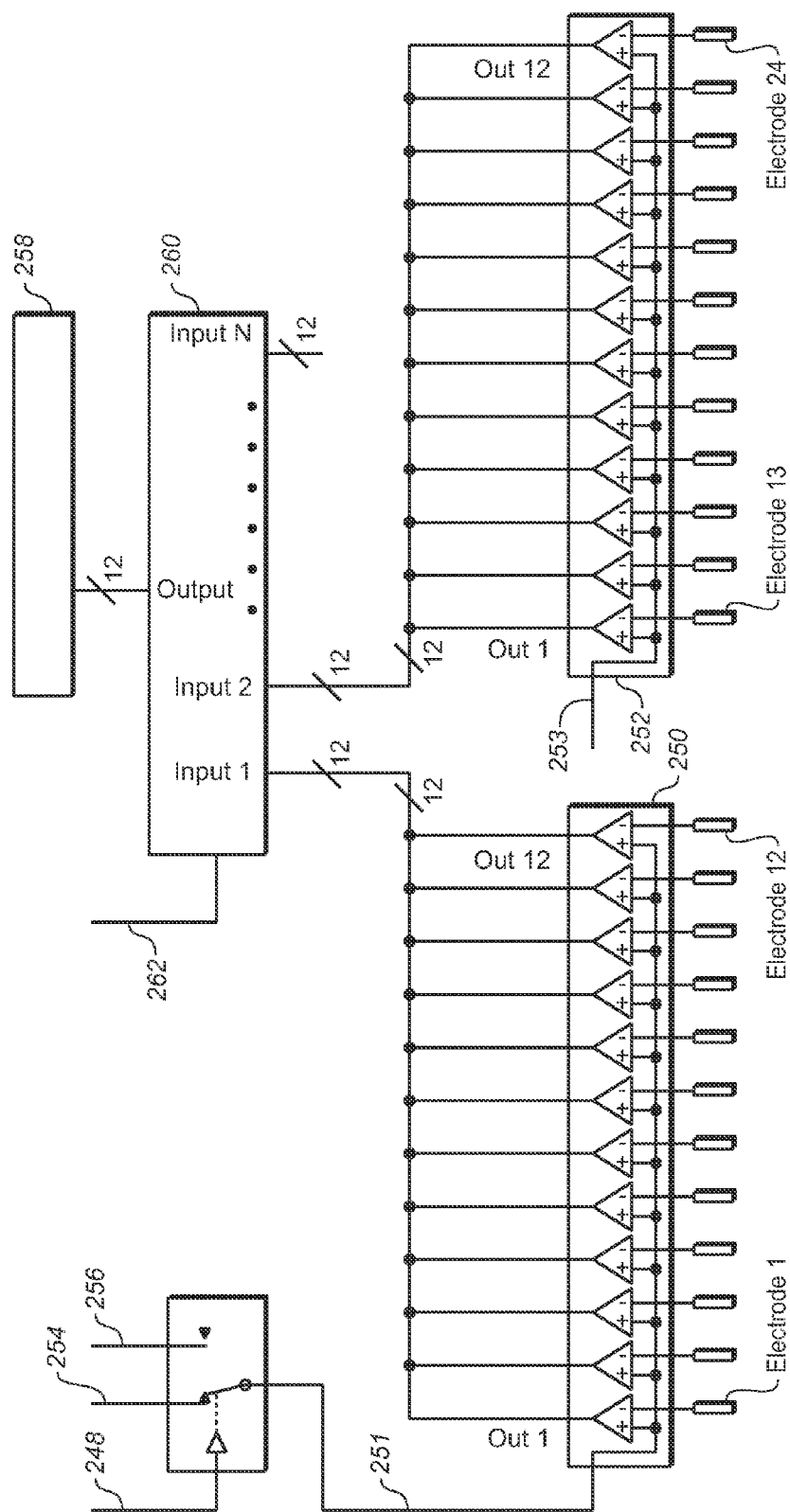
FIG. 15 is a schematic view of portions of the system of FIG. 14, showing the use of two separate banks of electrode pins.

FIGS. 14 and 15 show an exemplary electronics/measurement system, in accordance with aspects of the invention. Electrophysiological measurements may be performed on cells, using this system, by forming an electrical circuit across each individual aperture in the substrate. This may be accomplished using suitable electrodes, positioned on opposite sides of the membrane, for example, a sense electrode positioned above the membrane, and a ground electrode positioned below. For convenience, particularly in multi-channel embodiments, electrodes may be mounted and manipulated collectively using an electronics head. The electronics head may include a plurality of individual measurement probes, each capable of functioning as a sensing (or ground) electrode for an individual well of the measurement substrate, sequentially and/or simultaneously. These electrodes may be organized as an array (e.g., with m×n elements, where m, n=1, 2, 3, . . . ), preferably corresponding to the spacing of the measurement wells, or a multiple thereof, in at least a portion of the measurement substrate. The electronics head may be capable of two- or three-dimensional motion, enabling it to move between the various wells of the measurement substrate, as well as to a wash station, where the individual sensing electrodes can be washed between experimental runs. Each sensing electrode may be tied to its own high-impedance amplifier arrangement, consistent with that necessary for such measurements, preferably located in the housing of the electronics head. The analog output signals for each of the respective output amplifiers may be digitized by appropriate analog-to-digital (A/D) converters and transferred to an internal (onboard) computer and/or an external computer for further processing.

The individual circuits may be completed by the addition of a suitable electrolyte (e.g., saline) solution in each individual well of the measurement substrate above the membrane and by the introduction of saline solution below the membrane via a plenum, as described above. A common ground electrode may be located in the plenum fluid reservoir, thereby completing the measurement circuit.

FIG. 14 shows a partial schematic of an exemplary electronics head 226, in accordance with aspects of the invention. This exemplary electronics head is configured, consistent with the discussion above, to move a plurality of sensing electrodes 228 to the various wells 230 of the multi-well measurement substrate 232, thereby completing a separate electrical circuit 234 for each of the measurement wells. The electronics head includes several measurement "pins" 228. Each pin typically is a silver or silver-coated wire. In recent implementations, the pins have comprised silver-plated stainless steel to improve their rigidity. Any type of wire material that can be silver-plated could potentially suffice. This wire, in turn, is treated, typically with a hypochlorous acid, to give it a silver/silver chloride coating. The current-carrying mechanism between the biological cell or membrane and the pin then is transferred via a saline solution containing chloride ions, which react with the silver/silver chloride composite of each pin. The advantage of using the silver/silver chloride electrode is that it has an extremely low junction potential.

Once on the pin, this current may be converted to a voltage via a high-gain, low-noise trans-impedance amplifier 236. The voltage signal then is sent off to a multi-channel analog-to-digital A/D converter 246, which digitizes the voltage and saves it as a digital value in computer memory. Each electrode pin has its own channel; however, for the sake of simplicity, not all are shown in FIG. 14.

The ground side of each measurement circuit may be accomplished via a suitable electrode, such as a silver/silver chloride pellet 238 that is located in the bath solution 240 in the plenum. The bath solution in this embodiment should contain chloride ions for the silver/silver chloride electrode to function properly. Once the membrane carrier is sealed onto the plenum 242, for example, via the o-ring assembly 244, as previously described, the external saline solution may be introduced to each individual well (on the top side of the membrane carrier), and the internal saline solution may be introduced to the plenum (on the bottom side of the membrane carrier) via the main plenum channel, thereby completing the circuit.

The preferred functionality required of the electronics head is to make current measurements for each measurement well, as well as to maintain or alter the voltage across each individual well and therefore across the biological membrane. To be useful for measuring typical ion channel currents, this amplifier arrangement should be capable of clamping the voltage over physiological voltage ranges (at least about −100 to 100 mV), as well as be able to detect currents on the order of $10^{-12}$ Amps with a temporal bandwidth of about 10 kHz. These specifications are rather demanding, but may be attained using state-of-the-art operational amplifier circuits and printed circuit board layouts. In addition, depending on the number of measurements to be made in parallel, these specifications can place demanding requirements on the multi-channel A/D converter.

In some cases, it is necessary to maintain or hold the voltage across the biological membranes for a fixed period of time before actually making measurements. For example, many ion channels of interest require a "set-up" time at particular voltages to effect different conformational states of the channel prior to measurement. In some extreme cases, this "set-up" time may be as long as several minutes. This can have a detrimental impact on measurement throughput in cases in which the number of "wells" to be measured greatly exceeds the number of sensing electrodes.

Since it is much simpler to hold and maintain the voltage in a given measurement circuit, than it is to be able to actively change the voltage and in-turn digitize high-fidelity current measurements, a multiplexing scheme becomes attractive. In this geometry, some electrode pins are used to hold and maintain the voltage level across the membrane, while other sensing pins are using to make the high-bandwidth current measurements. When the functional aspects of the assay dictate, the roles of the "sensing pins" and the "holding pins" can be reversed thereby increasing the functionality of the device.

FIG. 15 shows an example of such a system, whereby two separate banks of electrode pins are utilized. A digital control line 248 controls the voltage input to two banks (250 and 252) of sensing pins via the selectable input lines 251 and 253. These input lines are connected directly to the non-inverting input of a low-noise operational amplifier. One control line 254 contains a voltage waveform going to the "active" sensing bank. The other input control line 256 is maintained at a fixed holding level. The respective outputs of the two amplifier banks then are multiplexed to a multi-channel A/D converter 258 via a multi-channel analog multiplexer 260 and digital multiplexer control line 262.

When amplifier "Bank 1" (250) is active, a time-varying voltage waveform can be input to the bank, and the output of the bank can be sent to be digitized via the A/D converter. At the same time, "Bank 2" (252) is maintained at a fixed voltage, and the outputs are disconnected from the A/D converter. These pins thus would be used to maintain a holding potential across the biological membrane during a pre-measurement set-up time. Upon initiation by the digital control lines, the two roles of the amplifier banks can then be reversed.

This type of multiplexing scheme has many advantages for high-throughput electrophysiological measurements. The ability to voltage clamp many wells simultaneously at the holding potential greatly increases throughput for assays requiring significant holding times. As an example, many sodium channels require 30 to 60 seconds of hold time at a negative voltage (e.g., −90 mV) before they will respond to a voltage stimulus. The ability to hold many samples simultaneously, and to multiplex the sensing electrodes between "output hold potentials" and "variable output/input sensing potentials," essentially removes this "inactivation state" in many wells in parallel, thereby improving the overall throughput of the measurements. The alternative would be sequential hold times and/or the necessity to move the electronics head between measurement locations.

In addition, electrically switching between amplifier banks is much faster than physically moving a single bank to a new set of measurement wells, also increasing throughput. Multiplexing the outputs at the electronics head itself, rather than at the A/D converter, which may be located some distance away, greatly simplifies the number of conductors that must be routed to the A/D converter. Lastly, this architecture is directly extendable to large numbers of electrodes, without making impractical demands on the number of channels and throughput of the A/D converter.

The electronics system described in this section more generally may be implemented for any suitable number and combination of amplifier banks (holding and active) and individual pin-counts (i.e., 12, 24, 48 etc.). The system may, for example, be used with a 1536-well measurement system and a 192-pin electronics head, among others, multiplexed to a 12, 16, or 48 channel A/D converter. This exemplary system would allow the voltage to be held on up to 192 wells, at the same time.

III.G Activation System

The activation system generally comprises any mechanism for rapidly activating (and/or deactivating) effector compounds in one or more sample wells, sequentially and/or simultaneously. For example, the system may use suitable light from a suitable light source to activate a photoactivatable compound, and/or a suitable voltage or change in voltage from a suitable voltage source to activate a voltage-activated compound, and so on. The system preferably uses light to "uncage" a photoactivatable "caged compound" comprising a ligand, a candidate ligand modulator, and/or the like.

Figure 16:
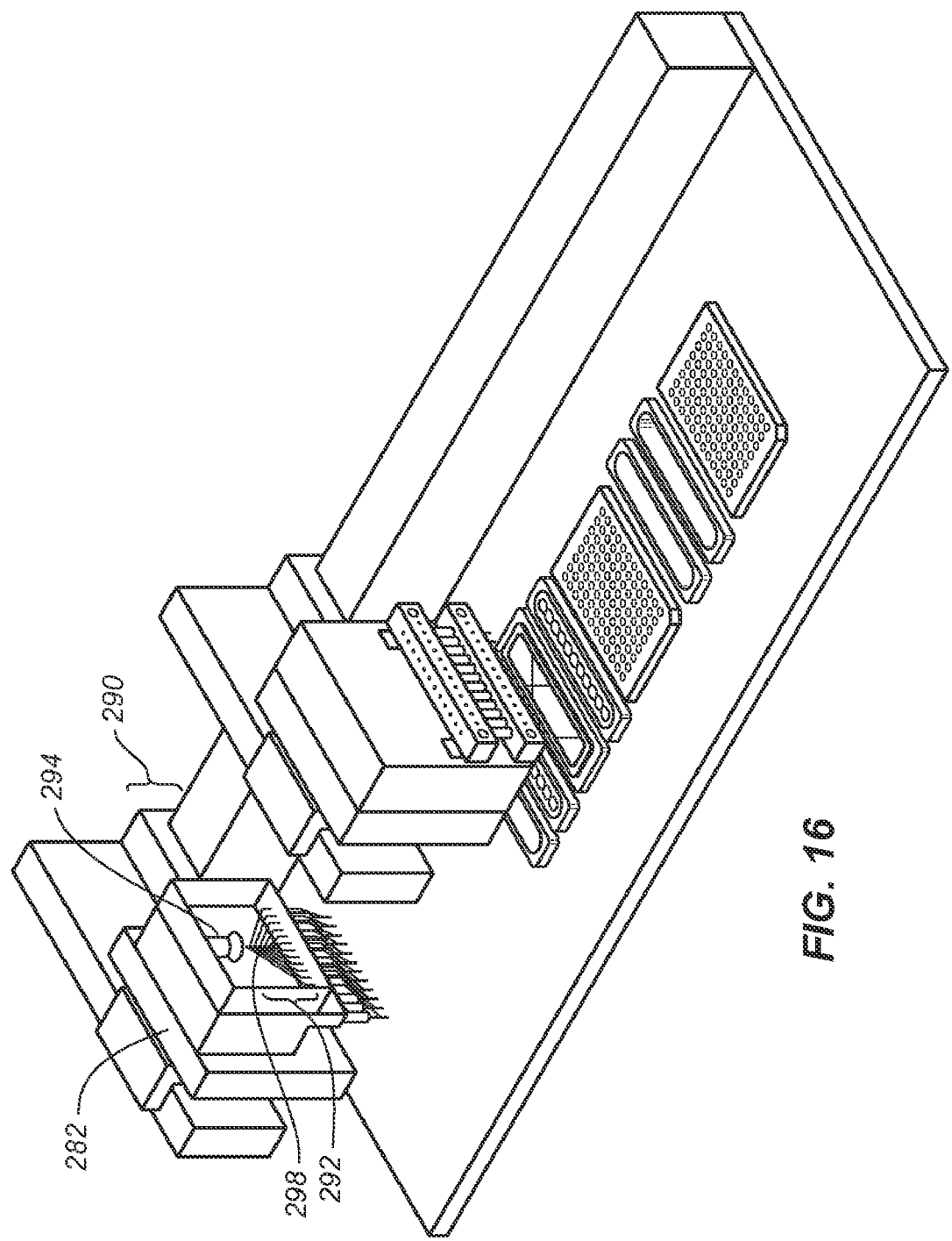
FIG. 16 is a schematic view of an exemplary activation system, showing how light energy may be directed via optical fibers to a plurality of biological samples, in accordance with aspects of the invention.

FIG. 16 shows an exemplary photoactivation system, in accordance with aspects of the invention. This system, which is associated here with an electronics head 282, includes a light source module 290 for generating light and a light coupler 292 for directing that light to one or more sample wells in a measurement substrate. The photoactivation system and the electronics/measurement system are adapted to work in concert to concurrently photoactivate compounds and record electronic signals such as voltages and/or currents from the same wells. This adaptation allows for the rapid and direct activation of effector compounds (e.g., through UV flash photolysis of a caged compound) and the simultaneous electrical recording of time-critical, ligand-activated ion channel or ion transporter events.

The light source module generally includes a light source 294 capable of generating light that in turn is capable of or adaptable to activate the photoactivatable compound. Suitable light sources may include continuous and/or time-varying sources, such as arc lamps, flash lamps, lasers, photodiodes, light-emitting diodes (LEDs), and/or electroluminescent lamps, among others. Preferred light sources for activating caged compounds include ultraviolet (UV) light sources, such as UV lasers and UV lamps. The light source module (and/or other components of the system) may control or modify one or more properties of the light outputted by the light source, such as its wavelength, intensity, polarization, and/or the like (e.g., using spectral filters, intensity filters, polarizers, and/or the like, respectively). The light source module (and/or other components of the system) also may control the timing of the delivery of the light onto the sample, including the start time and the duration of the illumination. This control may be achieved by pulsing the light source and/or by adding intervening gating optics, such as filters, shutters, acousto-optic modulators, and so on.

The light coupler generally comprises any mechanism for directing light from the light source onto one or more of the samples. Suitable light couplers may include optical fibers 298, free space optics, and/or evanescent wave coupling through the base of the substrate. Suitable light couplers further may include conventional optical elements such as mirrors, beam splitters, diffusers, collimators, telescopic optics, and/or the like, which may be used as appropriate in place of, or in addition to, the components previously described. The light may be directed onto the same well or sets of wells in contact with the electrical system, or a subset thereof, to facilitate coordinated activation and electrical measurement. For example, in FIG. 16, there is a one-to-one correspondence between electrodes and illuminable wells.

The photoactivation system may be controlled by a central processing unit (CPU). The CPU preferably is capable of controlling the optical pulse width and intensity of the source, so that the timing, duration, and light energy of the ultraviolet exposure can be controlled automatically.

III.H Exemplary Experimental Protocols

This section describes exemplary experimental protocols for using an electrophysiological measurement apparatus, in accordance with aspects of the invention.

The protocols begin with flushing and rinsing the instrument with the appropriate saline solutions, after which the user loads a multi-well carrier into the plenum fixture, which then is sealed by the application of high vacuum. This creates an air-tight vacuum controlled reservoir system on the bottom side of the membrane. The fluidics head then aspirates enough volume from the external (low-potassium) buffer reservoir to dispense approximately 3.5 μl into every well of the 384 (8×48) multi-well carrier. Once this is accomplished, the plenum fluidics system begins pumping high potassium (internal) saline solution into the plenum fluidics system. Using a combination of fluid flow and pressure pulsation, the plenum replaces the air in the plenum system reservoir with the high potassium solution. This procedure is carried out while maintaining a slight vacuum (~7-9 inches of $H_2O$) with respect to atmosphere in the plenum system, ensuring that any fluid flow across the measurement substrate is from the topside to the bottom side.

The fluidics head optionally may be set to dispense fluid into a user-selectable subset of the sample wells, such as one-fourth or one-half of the wells, among others. The partially filled plate then may be used for experiments, such as assay development, in which fewer (e.g., 96 or 192) measurements are necessary. The remaining, pristine portion of the plate then may be used for a subsequent assay, if at all.

Once the system is primed, the electronics head will sample each well of the multi-well substrate electrically to test for electrical continuity through the from the top side, through the photo-machined hole, to the bottom side ground electrode on each well of the substrate. This operation is reminiscent of the "bath test" in classical electrophysiology. Under normal operation, and with typical saline solutions, the equivalent resistance of each photo-machined hole is on the order of 2 to 4 MOhms, although other holes sizes and effective resistances could yield acceptable results. After the plate is primed, during the "hole test" measurement, the differential pressure across the measurement substrate is turned off, so as not to pull debris through the open hole during this phase of the experiment.

Figure 17:
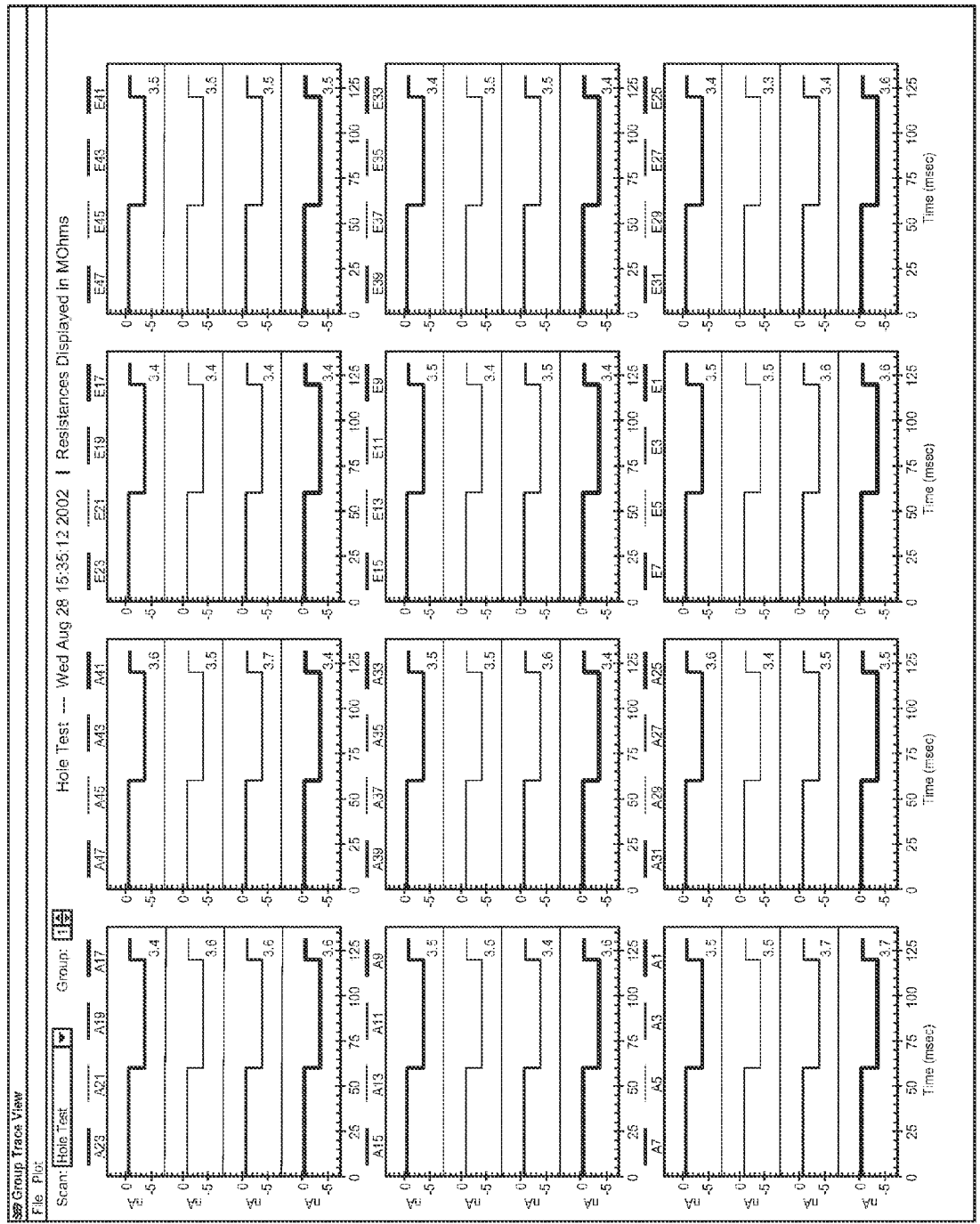
FIG. 17 is a screen shot from an exemplary graphical user interface showing 48 time traces from a "hole test" electrical measurement, in accordance with aspects of the invention

FIG. 17 is a screendump of an exemplary "hole test" from 48 wells of a measurement sequence. The hole test may be used to measure resistance by applying a small, square-wave test voltage to each pin of the electronics head, and measuring the resultant current from the respective trans-impedance amplifier. The individual plots show the measured current and the resulting resistance of each photo-machined hole in MOhms. The instrument uses these recordings to document the quality of the multi-well substrate and to verify that all systems are operational before proceeding with biological measurements. The instrument also uses these recordings to verify that each well of the multi-well substrate has effectively "primed," thereby yielding a measurable resistance. An air bubble present in a microhole at this point would yield an "open" circuit," resulting in a very large resistance measurement (e.g., several GOhms), and as such can be used to "flag" a problem in system performance. In addition, a statistical measure from the "hole test" measurements may be used to correct the subsequent voltage waveforms for voltage offsets present due to artifacts associated with liquid junction potentials (formed at the interface of the internal and external saline solutions) or day-to-day variations in the absolute silver/chloride electrode potentials.

Once the "hole test" procedure is finished, the fluidics head then proceeds to aspirate a sufficient volume from a (previously prepared) cell slurry reservoir to dispense approximately 3-4 µl of slurry into the top-side of every well of the multi-well carrier. This operation is performed while a slight differential vacuum is placed across the substrate, ensuring fluid flow (top to bottom) through each individual photo-machined hole in the substrate. This top to bottom flow ensures that during the sealing process only clean "external" buffer comes into contact with the microhole. Once the pipetting is finished, the system waits approximately 3-5 minutes, allowing differential pressure to pull a cell to each individual hole of the substrate and also allowing for high-resistance seal formation to take place. Once this time period is over, the electronics head performs a "seal test" by again applying a square-wave voltage (typically 10 mV amplitude), and measuring the resultant current from each respective trans-impedance amplifier.

Figure 18:
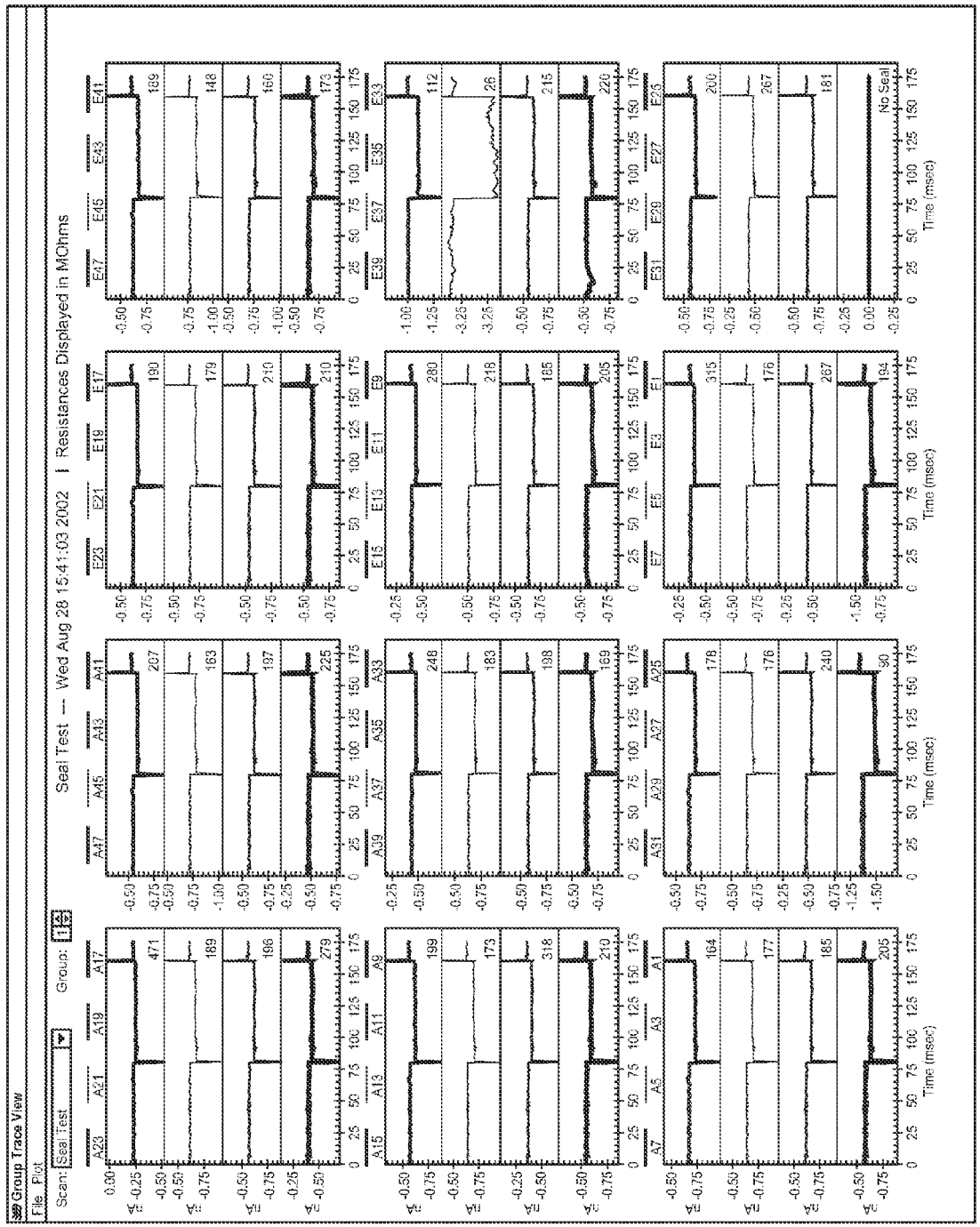
FIG. 18 is a screen shot from an exemplary graphical user interface showing 48 time traces from a "seal test" electrical measurement, in accordance with aspects of the invention.

FIG. 18 is a screendump from 48 wells of a measurement sequence. The average seal resistances have improved from approximately 3 MOhms during the "hole test" to approximately 150-200 MOhms during the "seal test". This difference in resistance is due to an individual cell lodging itself into the microhole, thereby increasing the resistance from the top-side chamber to the bottom side reservoir.

Following seal formation by the cell or biological membrane, the instrument typically exchanges fluids in the plenum reservoir beneath the substrate, replacing the high potassium internal solution with one containing a perforation solution. This exchange process is performed using the plenum peristaltic pump and at static differential vacuum, so as to maintain the previously achieved seal resistance between biological membrane and substrate.

The presence of a commonly used antibiotic for electrical permeabilization of the membrane has been reported to preclude the formation of a high-resistance seal between cells and a commonly used glass pipette. In a high-throughput system, this would require that the initial fluids on both sides of the measurement substrate be free from a perforation chemical solution until after a high-resistance electrical seal forms between the biological membrane and the measurement substrate, and that this solution be exchanged after the electrical seal has formed in a manner that does not disrupt the seal.

In contrast to the literature, we have found that it sometimes is desirable and feasible to include the perforation chemical in the initial internal solution, i.e., before a high-resistance seal has formed. This technique has the advantage of removing an entire fluid exchange step in the measurement protocol, as well as initiating the chemical process of electrical access through the cell membrane earlier in the process, greatly reducing the amount of time required before the system can make physiological ion channel measurements.

Typical plenum fluid exchange times are on the order of 60 seconds, after which the fluid in the plenum is "cycled" for several minutes. The perforation agent forms low-resistance electrical pathways through the accessible biological membrane at each micro-hole interface. Depending on the agent and the biological membrane of interest, this process can take anywhere from 5 minutes to 30 minutes to stabilize. Typical perforation times are on the order of 10 minutes.

Figure 19:
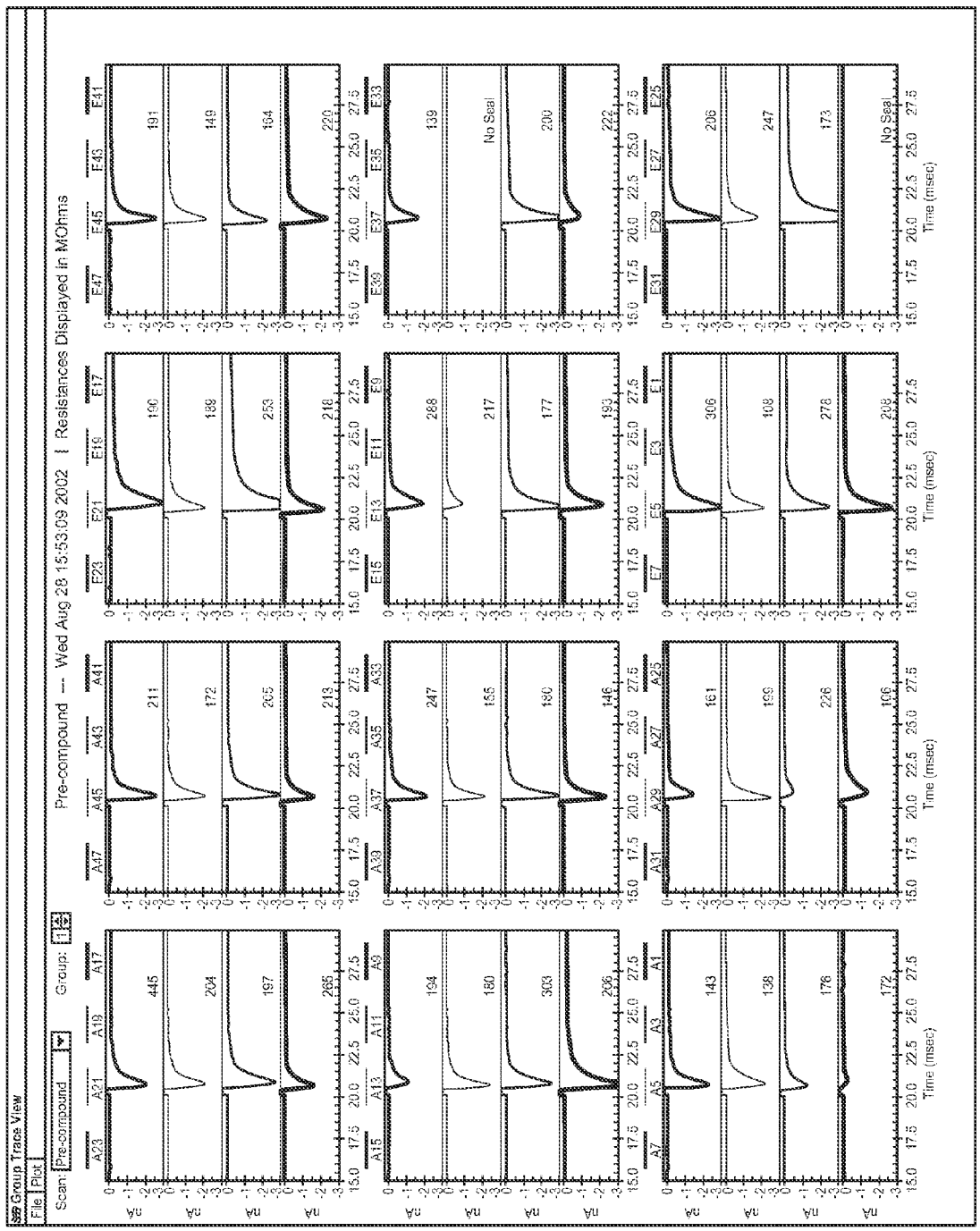
FIG. 19 is a screen shot from an exemplary graphical user interface showing 48 time traces from a electrophysiological recording of sodium channels in CHO cells, in accordance with aspects of the invention.

Once electrical access to the cell interior is achieved, the electronics head then is able to voltage clamp the biological membrane in each respective well, thereby enabling electrophysiological recordings. FIG. 19 consists of an electrical read made after achieving voltage clamp, whereby a voltage waveform was applied that depolarized the cells from a resting potential of −90 mV to 0 mV for approximately 100 msec. The biological membranes under study were CHO (Chinese Hamster Ovary) cells stably transfected with a sodium channel. As shown, upon depolarization, a small inward current measuring on the order of a few nA ($10^{-9}$ Amp) is present with the characteristic time signature of Na channel recordings. The time scale of FIG. 19 is only 15 milliseconds wide, reflecting the fact that the Na channels, once activated, quickly inactivate within about 3-5 milliseconds.

One measurement sequence comprises taking a pre-compound recording from each well, followed by the addition of an experimental compound by the fluidics head. Because of potential failures in making recordings in each well, the system must build in a level of redundancy to ensure that every experimental compound is tested. Depending on the cell type and assay, typical success rates are on the order of 50-80%. Failures may reflect a number of factors, including imperfect substrate priming, cell debris reaching the hole before a valid cell, and cells not having the particular ion channel current of interest. In the preferred embodiment, to ensure a valid measurement, a particular experimental compound is added to multiple wells of the multi-well substrate. This provides some system redundancy at the expense of compound throughput, i.e., the number of different compounds that can be analyzed per day. In the current implementation, the fluidics heads adds each well of a 96 well compound plate (or one quadrant of a 384 well compound plate) to each of the 384 (8×48) wells of the measurement substrate 4 times. After each successive and distinct compound addition, the fluidics head returns to the wash reservoir, where washing solution is supplied to each fluidics head needle. The fluidics head initiates a multiple aspirate/dispense cycle coincident with wash fluid being pumped to the needle in a process that ensures that both the inside and outside of the fluidics head needles are cleaned effectively before grabbing the next compound set.

After a short incubation time (during which the compound is in the presence of the biological membrane, typically 3-5 minutes), the electronics head revisits the substrate, initiating the same recording sequence to measure the effect of each compound on a post-compound recording. Measurements, in this manner allow the direct comparison of the same cell before and after the addition of an experimental compound. This makes the measurement "differential" in nature, allowing for good assay performance even in the presence of widely varying individual ion channel current levels, as each well can serve as its own control. In addition, differential measurements offer the advantage, in the case of inhibition-type assays, to discriminate between cells that have particular ion channel current expression and those that do not. Cells without expression on the pre-compound recording thus can be excluded from post-analysis. This type of measurement sequence is only one of many possible given the programmable functionality of the measurement system. In some cases, the experimental compounds may be added first, followed by a single electrical measurement read. Some protocols rely on two fluid additions, e.g., in the case of ligand-gated assays in which a known agonist is added to initiate a response, followed by an electronic read, compound read, and post read. In other cases, a second top side fluid addition can be used to add a known control, either for normalization of prior signals or to ensure that each well has the has the necessary ion channel currents of interest.

The apparatus may be used using any suitable set of steps, as determined by the cell, channel, test compound, assay format, and so on. The remainder of this section describes without limitation a few exemplary experimental protocols, or portions thereof, to supplement those presented above:

A. Assay 1. Pre-read, add test compound, post-read, and compare pre-read and post-read. This protocol may be used for typical inhibition assays, among others, and is good for voltage-gated assays. This approach assumes that there is a current to measure in the cell; if not, the results may be discarded.
B. Assay 2. Add agonist, pre-read, add test compound, post-read, and compare pre-read and post-read. This protocol may be used for slowly activated ligand-gated-channels, among others.
C. Assay 3. Add test compound, add agonist, and read. This protocol does not use a pre-read, but assumes that most cells have a current of known or average value.
D. Assay 4. Add caged compound, stimulate and pre-read simultaneously, add test compound, stimulate and post-read simultaneously, compare pre-read and post-read. This protocol may be used with caged (or activatable) compounds to initiate a simultaneous and rapid stimulation/read of a fast ligand-gated channel.
E. Assay 5. Add caged compound, add test compound, stimulate and post-read simultaneously. This protocol does not use a pre-read, but again assumes that most cells have a current of known or average value (e.g., due to known channel expression).
F. Assay 6. Pre-read, add test compound, post-read, add known compound (agonist or antagonist), re-read. The last read may be used for calibration of the data.

III.I Software Control and Analysis

This section describes exemplary aspects of software control and analysis, including (1) experiment set-up and control, (2) data analysis and reduction, and (3) leak reduction.

III.I.1 Experiment Set-up and Control

Figure 21:
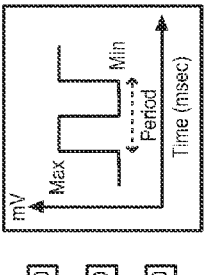
FIG. 21 is a screen shot from an exemplary graphical user interface regarding the setup and timing of a resistance "seal test," along with plate usage definitions, in accordance with aspects of the invention.
Figure 22:
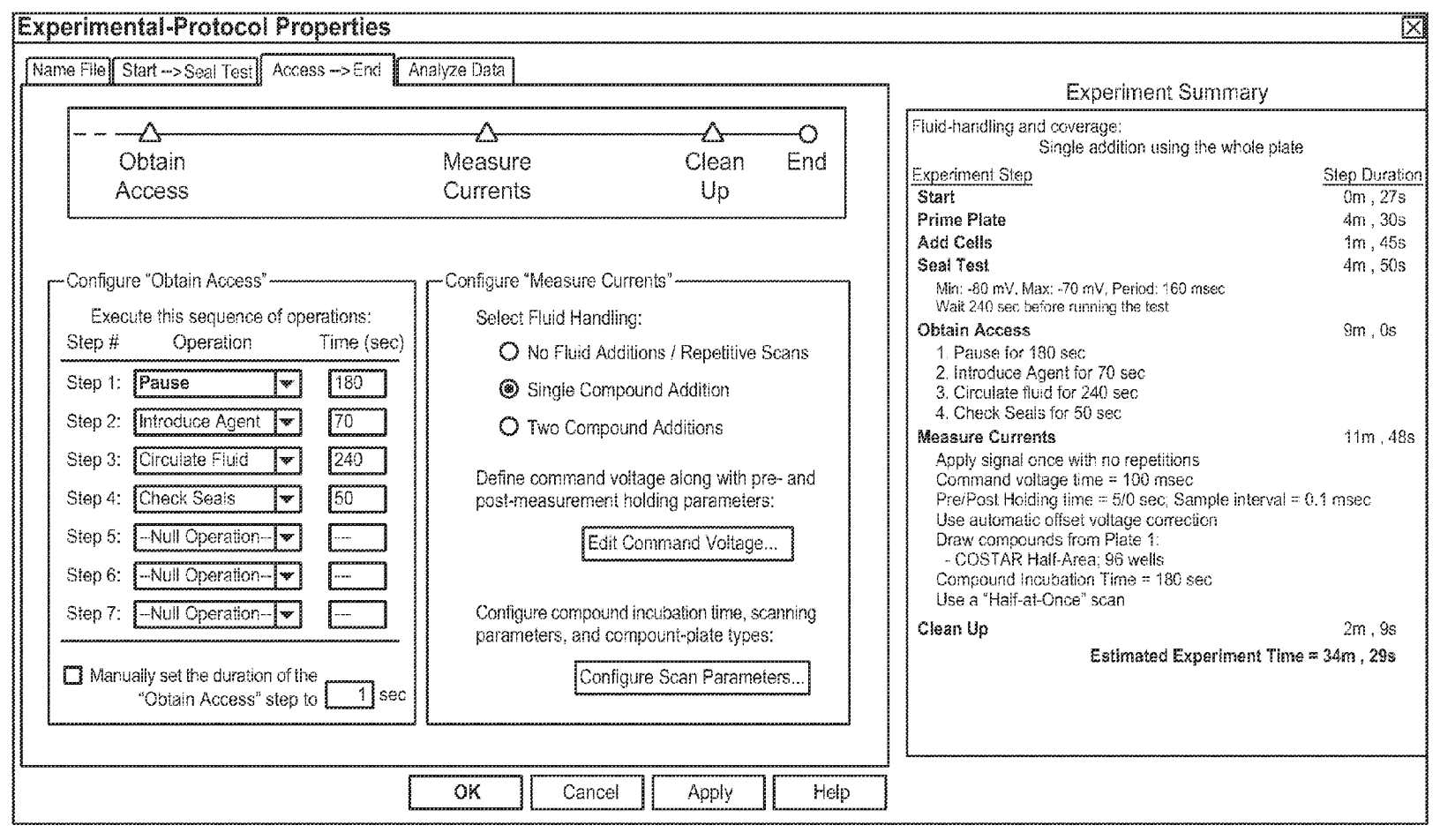
Figure 23:
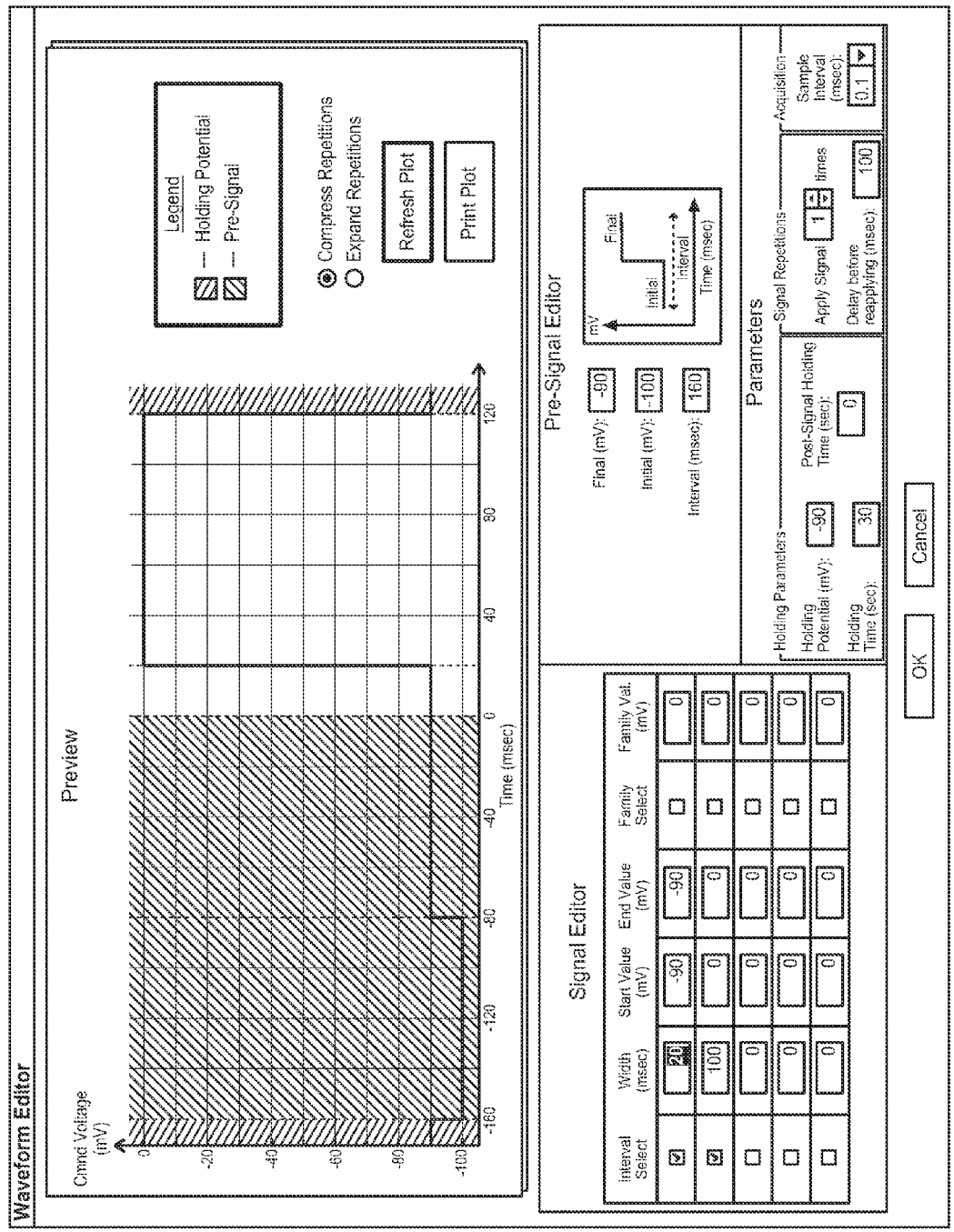
FIG. 23 is a screen shot from an exemplary graphical user interface regarding the setup and timing of the command voltage waveform protocols used in high-throughput electrophysiological recordings, in accordance with aspects of the invention.
Figure 24:
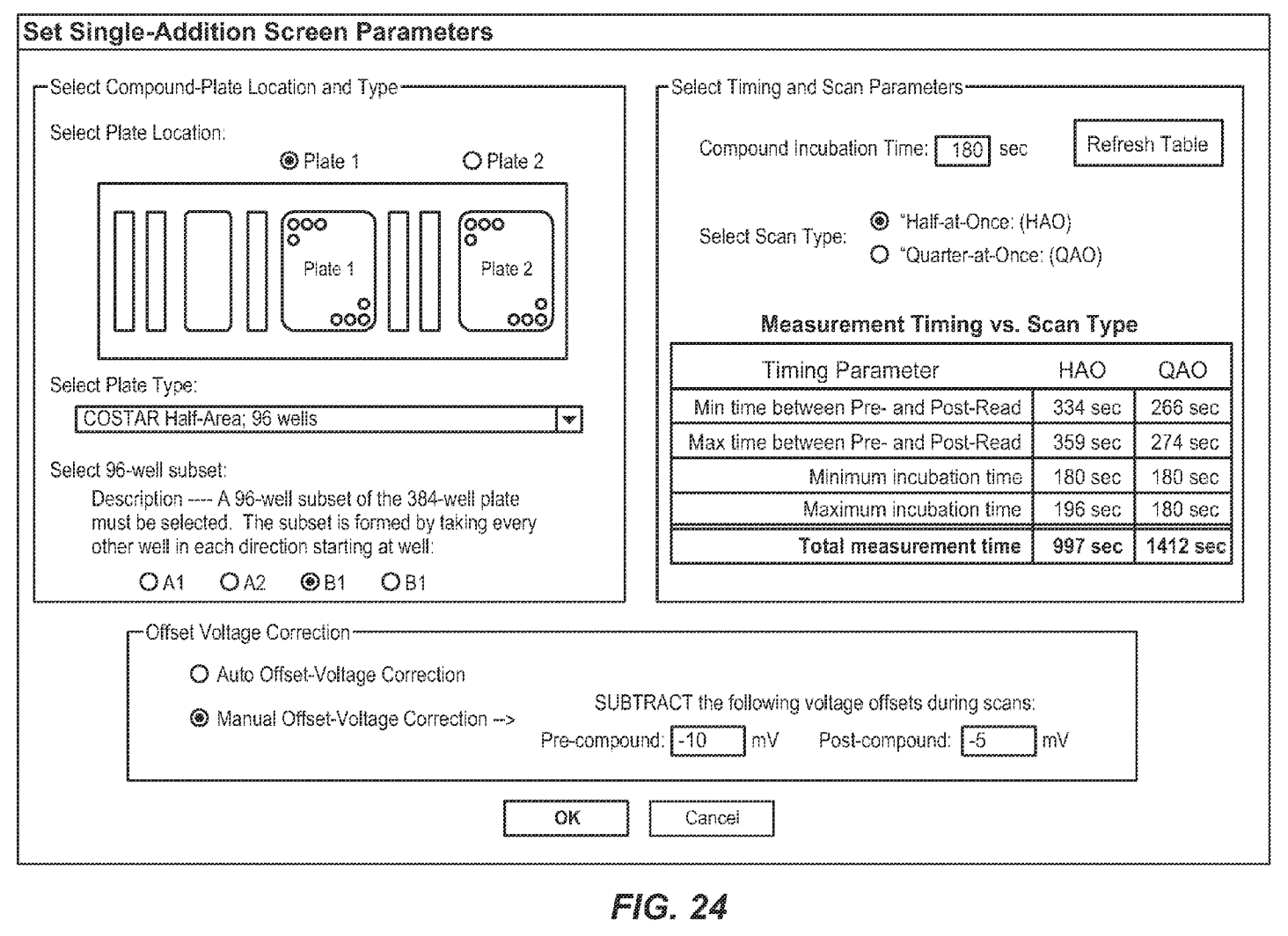

The system control software is presented as a graphical user interface, allowing the user to program various aspects of system control and data analysis. Examples of system control aspects include experiment scheduling, voltage waveform definition and timing, and compound addition scheduling and timing. FIG. 20 shows the GUI interface for overall experiment timing, as well as data file naming and directory designation. FIG. 21 shows the dialog box used to establish the number of wells to be tested (expressed as a percentage of the total), as well as the voltage waveform and timing to be associated with the "seal test" measurement. FIG. 22 shows the set-up and timing required for the addition of the perforation agent. FIG. 23 shows the dialog box associated with the definition of the voltage waveform, pre-holding voltages, and timing, as well as data sampling rates. Finally, FIG. 24 shows a dialog box used to define the compound addition sequence, timing, incubation time, and offset voltage corrections.

III.I.2 Data Analysis and Reduction

Figure 25:
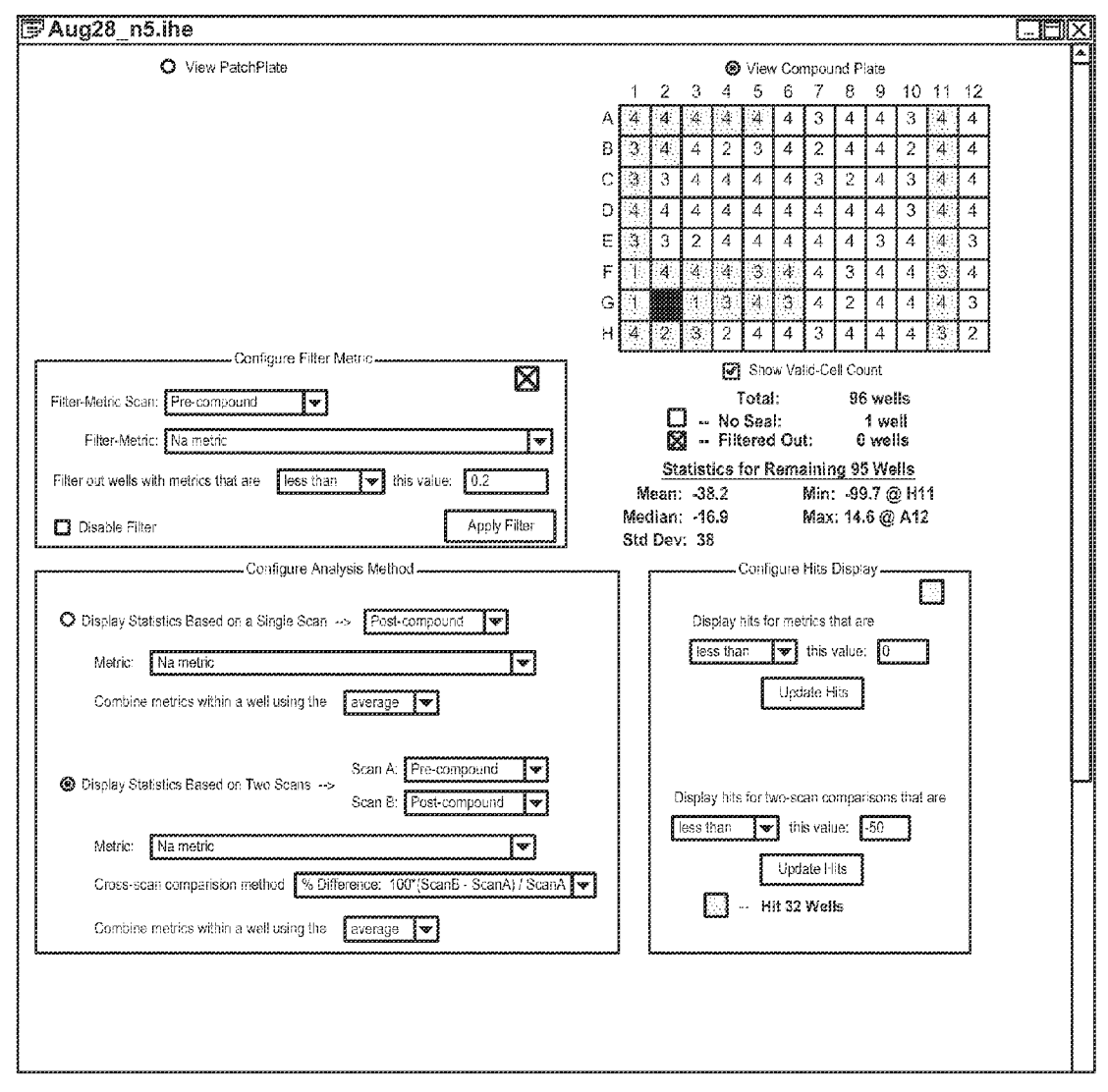

In addition to system control definitions, the system software also provides the means for analyzing data. Because the measurement process (prime, seal, measurable physiological current) does not have a 100% probability of success in each well, the system has built-in a level of redundancy, whereby a single experimental compound is added to multiple (typically 4) measurement wells. The software analysis includes in part the ability to deconvolve the various redundant measurement wells that are associated with a given experimental compound, analyze and scale the various time signatures associated with pre and post compound temporal recordings, and highlight areas of interest on the measurement plate according to various defined metrics. As an example, FIG. 25 depicts a compound plate view in which the software has been set up to compile the 4 individual compound measurements showing not only how many measurements (of the 4 possible) per compound were successful, but also to highlight according to % inhibition (post-read to pre-read comparison) the effects of the various compounds on the measurements. This latter feature is useful in tracking assay integrity as every plate can include positive and negative controls (wells which initiate a response and well that should not) so as to verify the robustness of the particular assay. In this particular example, FIG. 25 shows that column 11 represents wells that show a greater than 50% inhibition of signal, whereas column 12 represents wells that show less than 50% inhibition. This type of view can give the user a visual and efficient quantitative assessment of assay quality.

Figure 26:
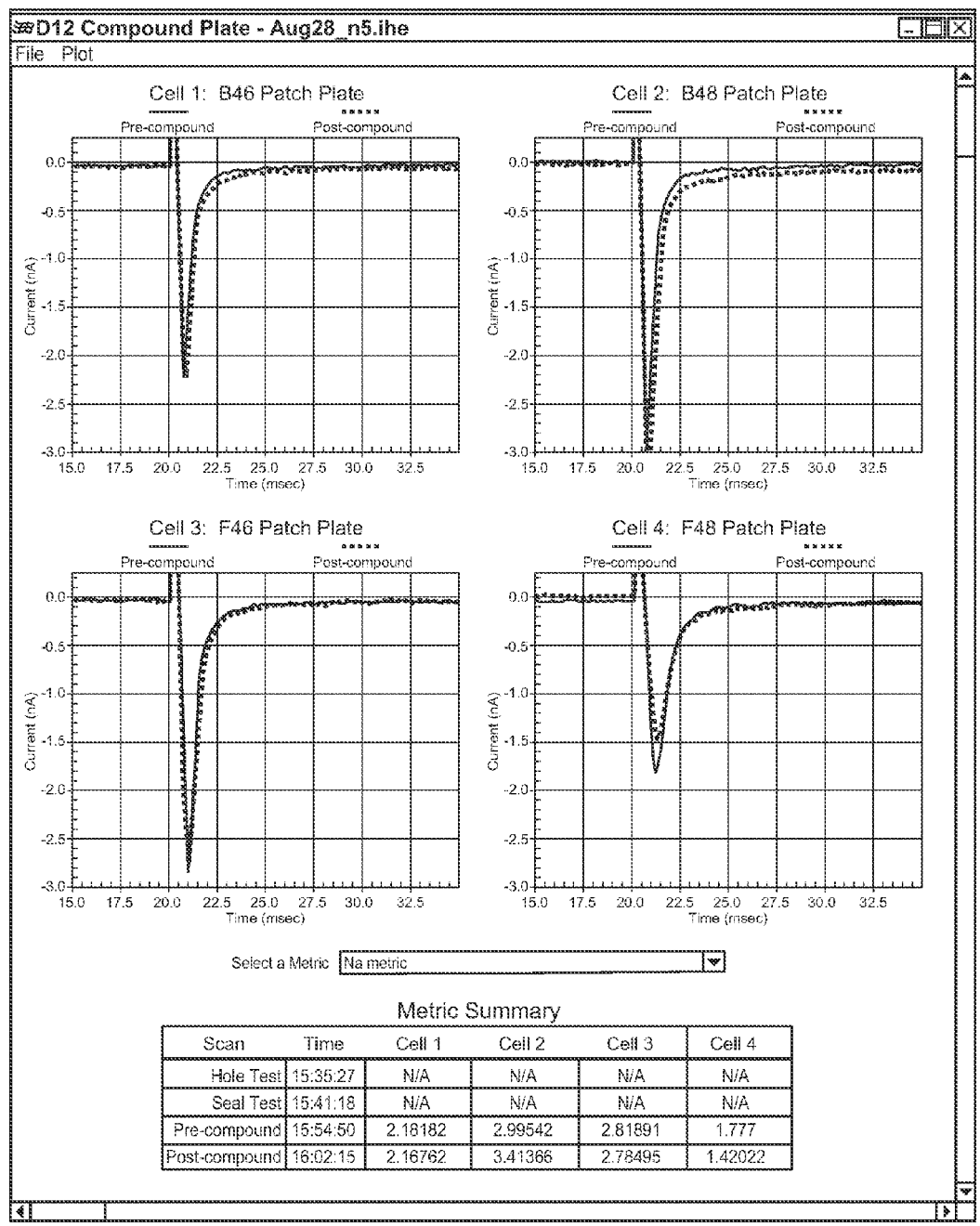
FIG. 26 is a screen shot from an exemplary graphical user interface showing four electrophysiological traces of sodium currents corresponding to one non-active compound from a high-throughput electrophysiological data set, in accordance with aspects of the invention.

In addition, the user can then "drill down" by double-clicking on each compound well to see the representative time traces that went into the analysis. FIG. 26 is the result from one such drill down on a "negative control well", i.e., a well which should initiate no post-read inhibition. Shown on the plot are the pre and post-compound time signals for the 4 associated measurement wells corresponding to this non-active compound.

Figure 27:
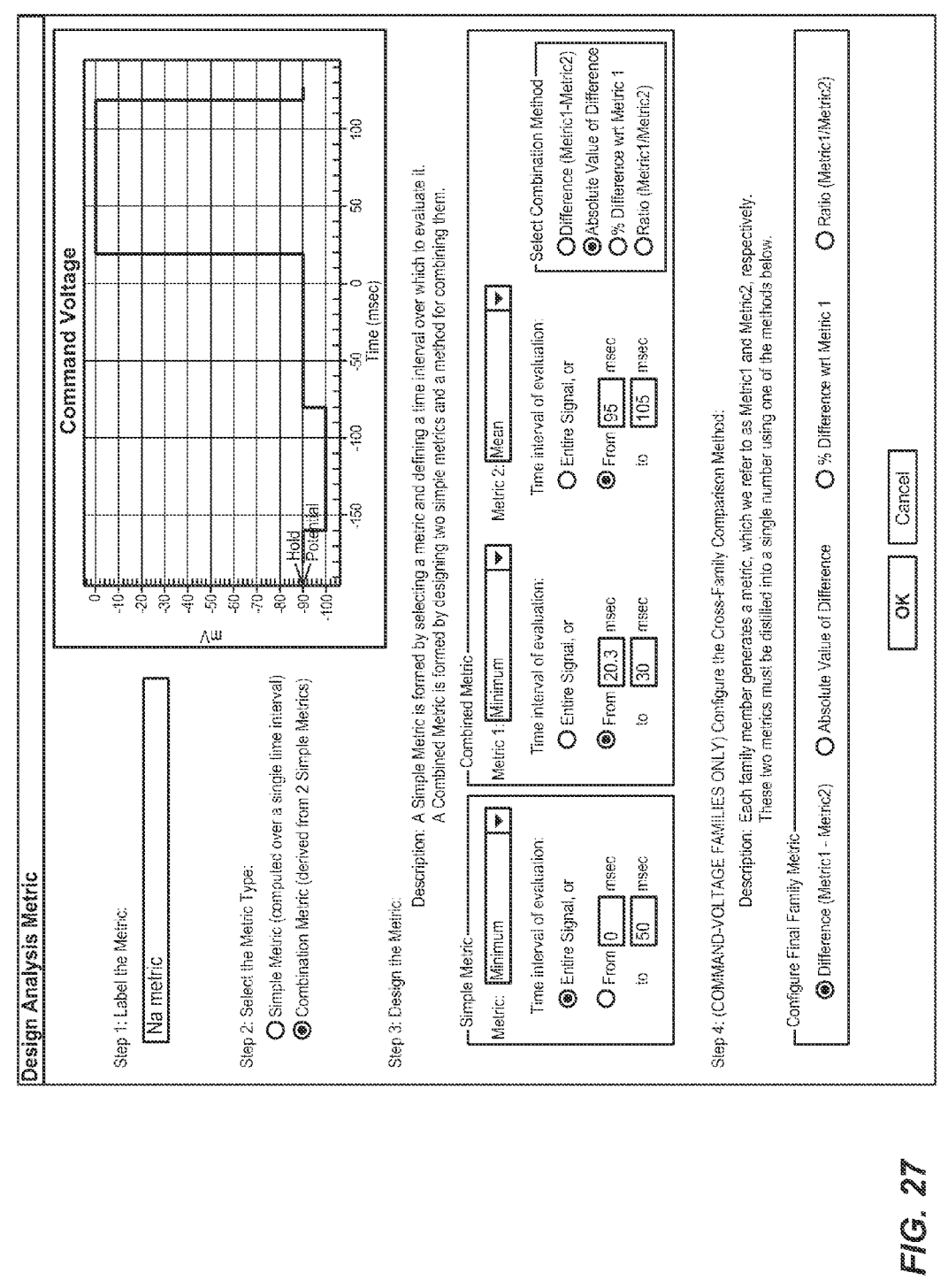

Another interesting and necessary feature of the data analysis software is the ability to define data "metrics" which compress the temporal signals according to user-defined mathematical expressions into simple numbers for post-analysis processing. Such metric definitions are essential in analyzing data from any high-throughput instrument, as it is difficult for an end-user to inspect hundreds of time traces generated every 30 minutes. FIG. 27 represents a metric definition window where the user has the ability to define various simple statistical measures, such as minimum, maximum, mean, etc., over a user-defined temporal region(s). In the example shown, the metric is defined as the maximum of the individual time curves between time points 20.3 and 30, as referenced to the mean of the same time curve between time points 95 and 105. This resultant difference is saved as an absolute value. The user then has the ability to take this simple process number (or metric) and export it to a file that easily can be accessed by various spreadsheet software packages for high-throughput plate-based analysis. This type of metric definition and processing is particularly advantageous for the assays described here, due to the measurement throughput of the apparatus and the inability for a user to look at all the raw time trace information gathered per run Another feature that is useful in the data acquisition software is the ability to change the data sampling rates during a voltage waveform, as well enabling user-definable "regions of interest" for data sampling. Due to the complex nature of ion channel gating, many assays require substantial and lengthy voltage setup protocols. However, in many of these cases, the useful and interesting physiological data is confined to a small interval or fraction of the entire protocol. Having the ability to down-select data acquisition to regions of interest greatly reduces the data handling and storage requirements of the system. Key examples of such protocols are those involving "use-dependent" pharmacological protocols, whereby the action of the drug increases the more times the channel is stimulated. During such protocols, it is not uncommon to want to stimulate the cell many times (10-50) over several minutes. However, the pharmacological data of interest may only be a small fraction of the total post-compound waveform protocol, e.g., the first pulse and the last pulse of the stimulation train. In these cases, the user could specify a very short and defined region in which the data is actually digitized and subsequently saved to reduce the demands of down-stream data handling. This also can be accomplished in part by changing data sampling rates (or "gear shifting"), whereby regions of greater interest are sampled more finely (e.g., at about 1 kHz) than regions of lesser interest.

III.I.3 Leak Reduction

One of many nonobvious results from this invention was the discovery that very successful electrophysiological recordings can be acquired with high-resistance seals much less than a GigaOhm (GOhm; $10^9$ Ohm). It generally has been accepted that, to achieve high quality whole-cell electrophysiological recordings from a traditional patch clamp, the leak current, i.e., the measure of the amount of current that can flow from the sense electrode to the ground electrode that does not flow through the cell membrane must, be very small. When expressed as a leak resistance (applied voltage divided by leak current), the preferred value for high quality recordings is thought to be near 1 GOhm and is referred to as a "GigaSeal". The reasons for this acceptance are that (i) if uncorrected, the current can be large compared to the true electrophysiological current, (ii) the large leak current contributes noise to the system, and (iii) the low resistance pathway to ground that the leak current offers greatly diminishes the ability of the system to voltage clamp, (i.e., control the voltage) of the biological membrane.

We have discovered that in making whole cell recordings of this type, high-resistance seals on the order of about 20 MOhms or higher will suffice in making quality whole-cell electrophysiological recordings. The leak current depends on the applied voltage waveform and the quality of the high-resistance seal. As an example, the leak current component would be approximately 1 nA for a 100 mV signal applied to a 100 MOhm seal. It has been determined, however, that leak currents of a few nA do not degrade the noise performance of a whole-cell clamp significantly, assuming that one can isolate the leak component from the rest of the signal. Furthermore, while the effect on the voltage clamp does create a voltage clamp error, such error is acceptable in most whole-cell recordings. For high-resistance seals, on the order of 100 MOhms, the error in voltage clamp as compared to that achieved under a GigaSeal is on the order of a few mV. Errors of a few millivolts have little impact on the performance of the system.

The biggest drawback to have large leak currents has to do with the ability to establish a true "baseline" from which to isolate the physiological current from the biological membrane from that of the leak component. It has been discovered, that in most cases with proper signal design, that the effects of the leak current can be corrected. FIG. 28 demonstrates two electrophysiological traces, with and without leak correction. Both signals were obtained using a command voltage having a depolarization step to +50 mV at time point 20 msec using the delayed rectifying potassium channel Kv1.5, after the application of the time-dependent blocking compound, tedisamil. As shown, depolarization step causes a time-decaying physiological current over the depolarization pulse. To correct the "leak current" component, the command voltage waveform also contains a "pre-pulse," comprising a small step voltage from −80 to −70 mV. (The pre-pulse may be conducted over any suitable voltage range, typically in the physiological (−100 to +60 mV) physiological range, in which there is little or no physiological current.) Relying on the fact that there is no physiological current triggered at these negative voltages, the measured current resulting from this pre-pulse can be used to isolate and subsequently estimate the leak current. This estimated value can then be used to "subtract" off the effects of the leak current during the entire voltage waveform, thereby yielding a true estimate of the baseline physiological current. Using this technique, we have been able to greatly increase the probability of success in making high-throughput electrophysiological recordings, by effectively lowering the acceptable high-resistance threshold from GOhms to tens of MOhms.

IV. Channel/Transporter Assays

The invention provides systems, including apparatus and methods, for monitoring the influence of effector agents and their modulators on membrane electrical activity. The effector agents may include activating/stimulatory agents and/or deactivating/inhibitory agents, among others, and modulators thereof. The system may be used to study any suitable electrophysiological process or event, particularly those involving ligand-gated ion channels and/or transporters. The system may be used with single samples, for example, using pipette-based or planar-substrate-based measurement devices. However, preferably, the invention may be used with multiple samples, sequentially and/or simultaneously, thereby enabling the study of fast ligand-gated electrophysiological events in a high-throughput manner.

IV.A Ion Channels/Transporters

The apparatus and methods provided by the invention may be used to study membrane components that are associated with or capable of bringing about measurable voltage changes and/or current flows across biological membranes. Suitable membrane components may include ion channels and ion transporters, among others, particularly ligand-gated channels and transporters.

IV.A.1 Ion Channels

Ion channels are membrane proteins that allow ions to flow across biological membranes, including the plasma membrane and organelle membranes. Ion channels are believed to create water-filled pores through which ions and some small hydrophilic molecules can pass by diffusion (i.e., the associated ion flow is passive, meaning that it occurs down a electrochemical gradient without requiring the input of energy.) Ligand-gated channels open or close in response to the binding, reaction, and/or other association of signaling molecules, termed "ligands." These channels may be gated by the binding of extracellular or intracellular ligands. In either case, the ligand is different than the substance that is transported when the channel opens.

IV.A.1.a Externally Gated Ion Channels

External ligands gate a variety of ion channels, including (1) ATP gated-channels, (2) glutamate-activated cationic channels, and (3) cys-loop superfamily channels. The ATP-gated channel superfamily includes the ATP2x and ATP2z receptors, among others. The glutamate-activated cationic receptor superfamily includes the NMDA, AMPA, and Kainate receptors, among others. Finally, the cys-loop receptor superfamily includes the nicotinic acetylcholine receptor, $GABA_A$ and $GABA_C$ receptors, glycine receptors, 5-$HT_3$ receptors, and anionic glutamate receptors, among others. These particular channels are controlled by the ligands that appear in the names of the channels.

External ligands most often are neurotransmitters, that is, chemical substances that transmit nerve impulses across a synapse, typically to another nerve cell or a muscle cell. Exemplary neurotransmitters include acetylcholine (Ach), amino acids (e.g., glutamic acid (Glu), glycine (Gly), and gamma aminobutyric acid (GABA)), catecholamines (e.g., noradrenaline and dopamine), miscellaneous monoamines (e.g., serotonin and histamine), and peptides (e.g., vasopressin (ADH), oxytocin, Gonadotropin-releasing hormone (GnRH), angiotensin II, cholecystokinin (CCK), substance P, and enkephalins such as Met-enkephalin and Leu-enkephalin), among others. These transmitters interact in the body with channels in the postsynaptic membrane to depolarize or hyperpolarize the postsynaptic membrane, depending on the transmitter and on whether the synapse is excitatory or inhibitory, respectively.

IV.A.1.b Internally Gated Ion Channels

Internal ligands also gate a variety of ion channels. These channels may include G-protein coupled receptors (GPCRs), chloride channels, and calcium-gated potassium channels, among others. These channels generally are controlled by second messengers, which are small signaling molecules such as cyclic AMP (cAMP), cyclic GMP (cGMP), and $Ca^{2+}$, among others. However, some of these channels are controlled by covalent modification, e.g., phosphorylation/dephosphorylation by kinases and phosphatases, respectively.

IV.A.2 Ion Transporters

Ion transporters are membrane proteins that use energy such as that derived from ATP to force ions or small molecules though the membrane up their electrochemical gradients. The transporters may be (1) direct active transporters, binding ATP directly and using the energy of its hydrolysis to drive active transport, or (2) indirect active transporters, using ATP indirectly by using the downhill flow of a different type of ion to drive active transport, where the gradient of the different type of ion is created by a direct active transporter, allowing another transporter to create a gradient of a different type of ion, and then using. Indirect transporters may be further subdivided into symporters and antiporters depending on whether the driving ion and the pumped ion (or other molecule) pass through the membrane in the same or opposite directions, respectively. Exemplary direct active transporters include the $Na^+/K^+$ ATPase and the H+ ATPase. Exemplary indirect active transporters include (1) symporters such as the Na+/glucose transporter, the various amino acid/Na+ transporters, and the Na+/iodide transporter, and (2) antiporters such as the $Na^+/K^+$ ATPase.

IV.B Activatable Compounds

Activatable compounds generally comprise any compounds, such as channel and/or transporter ligands, and modulators thereof, whose spatial and/or temporal release may be rapidly modulated by a suitable trigger, such as a change in light and/or voltage, among others.

Photoactivatable compounds, which are triggered by light, are preferred for many applications. Photoactivatable compounds are chemicals that are chemically altered such that the active nature of the compound is suppressed ("caged") until photoactivated, usually by a short pulse of ultra-violet (UV) light of wavelength in the range of 240 and 400 nm. The photolysis of such compounds is very fast and thereby can rapidly (in some cases in microseconds) release the active species of the compound. Suitable methods for producing these compounds and exemplary embodiments thereof are described in the following publication, which is incorporated herein by reference in its entirety for all purposes: Richard P. Haugland, HANDBOOK OF FLUORESCENT PROBES AND RESEARCH CHEMICALS ($6^{th}$ ed. 1996).

Photoactivatable compounds may be produced by derivatizing a ligand or modulator or other compound of interest with one or more photolabile protecting or caging groups. These caging groups, which collectively form a caging moiety, are selected and/or designed to interfere maximally with the binding, activity, and/or other function(s) of the derivatized compound. These groups may be detached rapidly (e.g., in microseconds to milliseconds) by appropriate illumination (e.g., flash photolysis at $\leq 360$ nm). The groups may be incorporated into biologically active molecules using any suitable mechanism, for example, by linkage to a hetero-atom (e.g., O, S, or N) as an ether, thioether, ester (including phosphate or thiophosphate esters), amine, or similar functional group. Exemplary caging groups may include (1) α-carboxy-2-nitrobenzyl (CNB) groups, (2) 1-(2-nitrophenyl)ethyl (NPE) groups, (3) 4,5-dimethoxy-2-nitrobenzyl (DMNB) groups, (4) 1-(4,5-dimethoxy-2-nitrophenyl)ethyl (DMNPE) groups, and (5) 5-carboxymethoxy-2-nitrobenzyl (CMNB) groups, among others. Significantly, when intracellular application is required, the caged compound often can be made cell permeable, such that it can be loaded into the cytoplasm of the cell for rapid intracellular activation at a later time.

Suitable photoactivatable compounds may include appropriately caged ligands, caged modulators, and the like, depending on the assay. Exemplary caged ligands include caged neurotransmitters and caged second messengers. Commercially available caged neurotransmitters include caged carbamylcholine, caged γ-aminobutyric acid (GABA), caged N-methyl-D-aspartic acid, and caged L-glutamic acid, all of which are biologically inactive before photolysis (Molecular Probes, Eugene, Oreg., USA). Commercially available caged second messengers include caged cAMP, caged inositol 1,4,5-triphosphate, caged cADP-ribose, and caged $Ca^{2+}$, at least several of which are membrane permeant (Molecular Probes). Exemplary caged modulators include caged ligand chelators, which can bind up ligand already present so that it no longer can bind to channels. Commercially available caged ligand chelators include caged $Ca^{2+}$ chelators (Molecular Probes).

IV.C Assays

The invention provides among others electrophysiological assays involving the use of activatable compounds, particularly for the study of ligand-gated membrane components such as ligand-gated channels and transporters. Activatable compounds may be especially useful in high-throughput applications, because they can be used to "introduce" compounds into solution, near an appropriate receptor, without requiring that the compound be pipetted into the solution at the time of the electrical measurement. This capability may be especially useful in systems such as the specific embodiment described above, in which rapid introduction or perfusion, on the time scale of typical channel or transporter kinetics, is difficult.

The assays may have any suitable design. Typically, caged versions of a ligand or modulator will be introduced into a system, and then activated at a suitable time using a suitable trigger, such as application of light. The electrical activity of the sample may be measured before, during, and/or after activation, so that the kinetic effects of the uncaged compound on the phenomenon of interest can be studied. Thus, in some assays, the caged compound may be a caged ligand, with the assay monitoring the effects of the ligand on a channel or transporter, typically in the presence of a candidate modulator. In other assays, the caged compound may be a caged ligand chelator or caged ligand degrader, with the assay monitoring the effects of removing the ligand from a system potentially habituated to the ligand, for example, by binding it up or destroying it. In yet other assays, the caged compound may be a caged modulator, with the assay monitoring the effects of the modulator on a system already exposed to the ligand.

V. EXAMPLES

The following numbered paragraphs describe additional and/or alternative aspects of the invention:

1. Electrophysiological measurement apparatus, comprising (A) a measurement platform including a moveable electronics head equipped with one or more sensing electrodes in communication with a signal processor and output device, and a moveable fluidics head equipped with one or more fluid-dispensing needles; (B) the platform including a plurality of stations, at least one of the stations being an integrated measurement plenum accessible by both the electronics head and the fluidics head, the measurement plenum including (i) a multi-well plate having a plurality of fluid-carrying chambers, each chamber containing biological material under investigation, and (ii) a thin substrate having an array of apertures in alignment with the chambers of the multi-well plate; and (C) a fluidics system operative to control and regulate the differential pressure across the substrate to achieve a high-resistance electrical seal between the substrate and the biological material.

2. The high-throughput electrophysiological measurement apparatus of paragraph 1, wherein the fluidics system is further operative to remove trapped gas from both sides of the substrate to form a continuous fluid pathway for conducting electrical current.

3. The high-throughput electrophysiological measurement apparatus of paragraph 1, wherein the fluidics system is further operative to apply a vacuum so as to pneumatically isolate a region on one side of the substrate.

4. The high-throughput electrophysiological measurement apparatus of paragraph 1, further including reagent inputs for one or more of the following: an extracellular saline solution, intracellular saline solution, wash solution, and chemically altered intracellular saline solution used to achieve low resistance electrical access to the inside of a cell.

5. The high-throughput electrophysiological measurement apparatus of paragraph 4, wherein intracellular solutions are exchanged without introducing pressure changes that would disrupt the high-resistance electrical seal.

6. The high-throughput electrophysiological measurement apparatus of paragraph 1, wherein the signal processor includes a multiplexer operative to route electrical signals derived from one or more of the electrodes on a selective basis.

7. The high-throughput electrophysiological measurement apparatus of paragraph 1, wherein the fluidics head includes a multi-channel manifold segment and a spatially offset single channel segment facilitating multi-channel and single channel operation.

8. The high-throughput electrophysiological measurement apparatus of paragraph 1, wherein the signal processor includes a low-noise, high-gain trans-impedance operational amplifier circuit and one or more isolated recording amplifier circuits.

9. The high-throughput electrophysiological measurement apparatus of paragraph 1, further including one or more positions for washing for the electronics head and the fluidics head.

10. The high-throughput electrophysiological measurement apparatus of paragraph 9, wherein each position for washing is automatically filled and drained via a peristaltic pump and vacuum assisted waste line.

11. The high-throughput electrophysiological measurement apparatus of paragraph 9, wherein each position for washing is capable of washing an entire head or portions thereof to conserve conserving wash solution.

12. The high-throughput electrophysiological measurement apparatus of paragraph 1, wherein the stations include one or more compound microplates, each having a standard well format accessible by the fluidics head.

13. The high-throughput electrophysiological measurement apparatus of paragraph 12, wherein the stations include one or more saline solution reservoirs accessible by the fluidics head.

14. The high-throughput electrophysiological measurement apparatus of paragraph 1, wherein the stations include a removable boat position for cell slurry addition accessible by the fluidics head.

15. The high-throughput electrophysiological measurement apparatus of paragraph 1, wherein the electronics head uses silver sensing electrodes, and the apparatus includes a station accessible by the electronics head used for depositing chloride on the electrodes.

16. A fluidics apparatus, comprising (A) a fluidics head operatively positioned to provide fluid to an examination site; and (B) a first dispenser set and a second dispenser set, both dispenser sets being connected to the fluidics head, wherein the dispenser sets are spaced from each other such that fluid can be alternately delivered exclusively from the first dispenser set, and exclusively from the second dispenser set, to a multi-compartment sample holder located at the examination site.

17. The apparatus of paragraph 16, wherein multiple samples at the examination site may be arranged across a plane, a Z axis being defined perpendicular to the plane, the first and second dispense sets being positioned at different heights relative to the Z axis.

18. The apparatus of paragraph 17, wherein the second dispense set has a single dispenser element positioned lower than the first dispense set relative to the Z axis, so that when the single dispenser element is dispensing fluid to a sample at the examination site, the second dispense set avoids contact with any other samples at the examination site.

19. The apparatus of paragraph 16, wherein the first dispense set includes multiple dispenser elements, and the second dispense set includes a single dispenser element.

20. The apparatus of paragraph 16, wherein each of the first and second dispense sets includes multiple dispenser elements.

21. An apparatus for measuring an electric property of a membranous sample, comprising (A) a platform; (B) an examination station on the platform; (C) a container at the examination station including first and second compartments separated by a substrate having one or more apertures arranged and dimensioned for conducting a patch clamp experiment on a membranous sample in the first compartment; (D) one or more sample processing stations on the platform; (E) a fluidic transfer device mounted on the platform configured to move material from the reservoir station to the container at the examination station; and (F) an electrode device configured to move in and out of contact with the membranous sample in the first compartment of the container at the examination station.

22. The apparatus of paragraph 21, wherein the sample processing stations and the examination station are arranged along a linear processing path, so that the fluidic transfer device and the electrode device can move between stations along overlapping segments of the processing path.

23. The apparatus of paragraph 22, processing path has a detection segment and a preparation segment, the detection segment and the preparation segment overlapping in a region including the examination station.

24. The apparatus of paragraph 21, wherein the sample processing stations include one or more input stations for holding sample or reagent material to be transferred to the examination station.

25. The apparatus of paragraph 21, wherein the sample processing stations include one or more wash stations.

26. The apparatus of paragraph 21, wherein the sample processing stations include one or more renewal stations.

27. The apparatus of paragraph 21, further comprising a computer, program, and interface configured to allow a user to determine a processing routine including coordinated movement of the fluidic transfer device and the electrode device relative to the examination station.

28. The apparatus of paragraph 21, wherein the processing path has a first end portion configured for carrying out sample preparation, and a second end portion configured for carrying out sample analysis.

29. The apparatus of paragraph 28, wherein the first end portion and the second portion each include the examination station.

30. The apparatus of paragraph 21, wherein each of the fluidic transfer device and the electrode device has a portion that is moveable along a Z axis perpendicular to the platform.

31. An apparatus for conducting a biological experiment, comprising (A) a platform; (B) an examination station located on the platform along a linear processing path; (C) one or more sample preparation stations located along the processing path; (D) a guide rail structure mounted on the platform substantially parallel to the processing path; (E) a fluidics head moveable along the guide rail for transferring material between stations along the processing path; and (F) a detector head moveable along the guide rail, configured to sense a property of a biological sample located at the examination station.

32. The apparatus of paragraph 31, further comprising a container at the examination station including first and second compartments separated by a substrate having one or more apertures arranged and dimensioned for conducting a patch clamp experiment on a membranous sample in the first compartment.

33. The apparatus of paragraph 21, wherein a first electrode is connected to the second compartment, the detector head having a second electrode for contacting the membranous sample in the first compartment.

34. The apparatus of paragraph 31, further comprising a drive mechanism that drives each of the fluidics head and the detector head along the guide rail.

35. The apparatus of paragraph 31, further comprising (G) a first drive mechanism that drives the fluidics head along the guide rail, and (H) a second drive mechanism that drives the detector head along the guide rail.

36. The apparatus of paragraph 31, wherein the fluidic transfer device and the electrode device can move between stations along overlapping segments of the processing path.

37. The apparatus of paragraph 31, wherein the processing path has a detection segment and a preparation segment, the detection segment and the preparation segment overlapping in a region including the examination station.

38. The apparatus of paragraph 31, wherein the one or more sample processing stations include one or more input stations for holding sample or reagent material to be transferred to the examination station.

39. The apparatus of paragraph 31, further comprising a computer, program, and interface configured to allow a user to determine a processing routine including coordinated movement of the fluidic transfer device and the electrode device relative to the examination station.

40. A method for measuring an electrical property of a membranous sample, comprising (A) selecting an electrophysiological measurement apparatus comprising (i) a substrate having an aperture, (ii) first and second fluid compartments, separated by the substrate, in fluid communication via the aperture, and (iii) first and second electrodes, the first electrode in electrical contact with the first fluid compartment, and the second electrode in electrical contact with the second fluid compartment; (B) adding a perforation agent to the second compartment, the perforation agent being capable of forming an electrically conductive hole through the membranous sample; (C) adding the membranous sample to the first compartment, after the step of adding a perforation agent to the second compartment; (D) sealing the membranous sample across the aperture to form an electrically tight seal; and (E) measuring, using the electrodes, at least one of a current and a voltage across the aperture and at least a portion of the membranous sample.

41. The method of paragraph 40, the membranous sample including a trapped volume, wherein the perforation agent forms an electrically conductive hole through the membranous sample, such that the trapped volume is in fluid communication with the second fluid compartment but not with the first fluid compartment.

42. The method of paragraph 40, wherein the perforation agent is selected from the group consisting of amphotericin B and nystatin.

43. An electrophysiological measurement apparatus, comprising (A) a sample holder having a plurality of electrophysiological measurement sites; (B) a plurality of electrodes, each electrode in electrical contact with a different measurement site; and (C) a controller configured to set the electrodes for one of at least two functions, and to switch the electrodes between the at least two functions; wherein the controller has set a first set of electrodes for a first function, and a second set of electrodes for a second function, the first and second functions being different.

44. The method of paragraph 43, wherein the controller changes the function performed by the first set of electrodes from the first function to the second function.

45. The method of paragraph 43, wherein the controller interchanges the functions performed by the two sets of electrodes.

46. The method of paragraph 43, wherein the first function is to hold a voltage across a sample at the measurement site at a preselected value, and wherein the second function is to measure an electrical property of a sample at the measurement site.

47. The method of paragraph 46, wherein the electrical property is at least one of a current or a voltage across at least a portion of the sample.

48. The method of paragraph 43, wherein the controller includes a multiplexer configured to route electrical signals derived from the electrodes on a selective basis.

49. The method of paragraph 43, wherein the measurement sites comprise a substrate having an aperture, and first and second fluid compartments, separated by the substrate, in fluid contact via the aperture.

50. The method of paragraph 43, wherein the controller includes a low-noise, high-gain, trans-impedance operational amplifier circuit and at least one isolated recording amplifier circuit.

51. The method of paragraph 43, wherein the first function is performed by an analog-to-digital (A/D) converter.

52. The method of paragraph 43, wherein the electrodes are disposed in an electronics head, and wherein the electronics head is moveable so that the electrodes can be moved to bring them into contact with a different set of measurement sites within the sample holder.

53. The method of paragraph 43, the apparatus including 48 electrodes, wherein 36 of the electrodes are set to perform the first function, and wherein 12 of the electrodes are set to perform the second function.

54. A method of performing an electrophysiological experiment, comprising (A) positioning a plurality of samples at a corresponding plurality of measurement sites, in an electrophysiological measurement apparatus; (B) positioning a plurality of electrodes at least a subset of the measurement sites, each electrode in electrical contact with a different measurement site; (C) setting a first set of electrodes to perform a first function; (D) setting a second set of electrodes to perform a second function, wherein the second function is different than the first function; and (E) changing the function performed by the first set of electrodes from the first function to the second function.

55. The method of paragraph 54, further comprising changing the function performed by the second set of electrodes from the second function to the first function.

56. The method of paragraph 55, wherein the steps of changing the function performed by the first set of electrodes and the function performed by the second set of electrodes are performed simultaneously.

57. The method of paragraph 54, further comprising setting the first and second set of electrodes to perform the same function.

58. The method of paragraph 54, wherein the first function is to hold a voltage across a sample at the measurement site at a preselected value, and wherein the second function is to measure an electrical property of a sample at the measurement site.

59. The method of paragraph 58, wherein the electrical property is at least one of a current or a voltage across at least a portion of the sample.

60. The method of paragraph 54, wherein the first function is performed by an analog-to-digital (A/D) converter.

61. The method of paragraph 54, further comprising moving the electrodes to bring them into contact with a different set of measurement sites within the sample holder.

62. The method of paragraph 61, further comprising repeating, for the different set of measurement sites, the steps of setting the first set of electrodes to perform a first function, setting the second set of electrodes to perform the second function, and changing the function performed by the first set of electrodes from the first function to the second function.

63. The method of paragraph 54, there being 48 electrodes, wherein 36 of the electrodes are set to perform the first function, and wherein 12 of the electrodes are set to perform the second function.

64. A method for measuring an electrical property of a membranous sample, the membranous sample enclosing a trapped volume, the method comprising (A) selecting an electrophysiological measurement apparatus comprising (i) a substrate having an aperture, (ii) first and second fluid compartments, separated by the substrate, in fluid communication via the aperture, and (iii) first and second electrodes, the first electrode in electrical contact with the first fluid compartment, and the second electrode in electrical contact with the second fluid compartment; (B) adding the membranous sample to the first fluid compartment, the membranous sample forming an electrically tight seal across the aperture; (C) permeabilizing at least a portion of the membranous sample, after it is sealed across the aperture, such that the trapped volume is in fluid communication with the second fluid compartment but not with the first fluid compartment; (D) exchanging at least a portion of the fluid in the second fluid compartment, while maintaining the electrically tight seal; and (E) measuring, using the electrodes, at least one of a current and a voltage across the aperture and at least a portion of the membranous sample.

65. The method of paragraph 64, wherein the membranous sample is selected from the group consisting of cells, subcellular organelles, and vesicles.

66. The method of paragraph 64, wherein the electrophysiological measurement apparatus further comprises an automated fluid exchange system configured to exchange fluid in the second compartment.

67. The method of paragraph 66, wherein the fluid exchange system maintains the second fluid compartment at a slightly lower pressure than the first fluid compartment.

68. The method of paragraph 64, wherein the step of measuring at least one of a current and a voltage is performed before and after the step of exchanging at least a portion of the fluid in the second fluid compartment.

69. The method of paragraph 64, wherein the step of permeabilizing the portion of the membranous sample sealed across the aperture includes contacting the portion with a pore former.

70. The method of paragraph 64, wherein the step of permeabilizing the portion of the membranous sample sealed across the aperture includes disrupting the portion using an electrical pulse.

71. The method of paragraph 64, wherein the step of permeabilizing the portion of the membranous sample sealed across the aperture includes disrupting the portion using a pressure pulse.

72. The method of paragraph 64, wherein the step of exchanging at least a portion of the fluid in the second fluid compartment results in the exchange of at least a portion of the fluid in the trapped volume.

73. The method of paragraph 64, wherein the portion of the substrate adjacent the aperture is at least substantially planar.

74. The method of paragraph 64, the electrophysiological measurement apparatus further comprising (1) a second aperture, (2) third and fourth fluid compartments, separated by the substrate, in fluid communication via the second aperture, and (3) third and fourth electrodes, the third electrode in electrical contact with the third fluid compartment, the fourth electrode in electrical contact with the fourth fluid compartment, further comprising (A) adding a second membranous sample to the third fluid compartment, such that the second membranous sample forms an electrically tight seal across the second aperture; (B) permeabilizing at least a portion of the membranous sample sealed across the aperture, such that the trapped volume is in fluid communication with the second fluid compartment; (C) exchanging at least a portion of the fluid in the second fluid compartment, while maintaining the electrically tight seal; and (D) measuring, using the electrodes, at least one of a current and a voltage across the aperture and at least a portion of the membranous sample.

75. The method of paragraph 74, wherein the second and fourth fluid compartments are joined to form a single fluid compartment, and wherein the second and fourth electrodes are the same.

76. Electrophysiological measurement apparatus, comprising (A) a multi-well plate having a plurality of fluid chambers, each configured to support a biological material to be measured; (B) a thin substrate having an array of apertures in alignment with the chambers of the multi-well plate, wherein the substrate is joined to the multi-well plate such that the chambers are open at the top and sealed at the bottom, except for the apertures, and wherein the diameter of the apertures is less than the diameter of the biological material, thereby enabling a high-resistance seal to be formed between the biological material in each chamber and a corresponding aperture; (C) a fluid plenum to receive the multi-well plate such that one side of the substrate is immersed; (D) a first electrode disposed in the fluid plenum; (E) at least one second electrode moveable into the top openings of the fluid chambers of the multi-well plate; and (F) electrophysiological measurement circuitry in electrical communication with the electrodes.

77. The electrophysiological measurement apparatus of paragraph 76, wherein there is a single aperture associated with each chamber of the multi-well plate.

78. The electrophysiological measurement apparatus of paragraph 76, wherein each compartment contains a biological material to be measured.

79. The electrophysiological measurement apparatus of paragraph 76, wherein the substrate is a plastic substrate having a glass coating at least in the region where the high-resistance seal is formed between the material and the substrate.

80. The electrophysiological measurement apparatus of paragraph 79, wherein the substrate is selected from the group consisting of polyethylene terephthalate (PET) and polyimide.

81. The electrophysiological measurement apparatus of paragraph 76, wherein the diameter of the apertures is in the range of about 1 to 10 micrometers.

82. The electrophysiological measurement apparatus of paragraph 76, wherein the apertures are tapered.

83. The electrophysiological measurement apparatus of paragraph 76, wherein the multi-well plate is sealed to the fluid plenum, enabling a differential pressure to be applied relative to the fluid in each chamber, thereby causing the material in each chamber to migrate to a respective aperture.

84. The electrophysiological measurement apparatus of paragraph 76, wherein the multi-well plate is sealed to the fluid plenum, enabling a differential pressure to be maintained relative to the fluid in each chamber until between the material in each chamber forms the high-resistance seal to the corresponding aperture.

85. The electrophysiological measurement apparatus of paragraph 76, wherein the fluid plenum includes a chemical reagent causing the material in each chamber to electrically permeabilize in the vicinity of the aperture.

86. The electrophysiological measurement apparatus of paragraph 76, wherein a high voltage is temporarily applied across the electrodes to permeabilize the material in each chamber, at least in the vicinity of the apertures.

87. The electrophysiological measurement apparatus of paragraph 76, further comprising a mechanism for moving the electrode into the chambers of the multi-well plate so as to automate the measurement of the material contained therein.

88. The electrophysiological measurement apparatus of paragraph 76, further comprising (G) a plurality of electrodes in alignment with a plurality of the chambers of the multi-well plate; and (H) a mechanism for moving the electrodes into the chambers of the multi-well plate to perform simultaneous measurements on the material contained therein.

89. The electrophysiological measurement apparatus of paragraph 76, further comprising a system for transferring fluids from one or more sources to the chambers of the multi-well plate.

The disclosure set forth above may encompass multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and nonobvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements. It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

REFERENCES

[1] Denyer, J., Worley J., Cox B., Allenby G., and Banks M., HTS Approaches to Voltage-gated Ion Channel Drug Discovery, *Drug Discovery Today*, Vol. 3., No. 7, July 1998, pp. 323-332.

[2] Ausubel, F. M., Brent, R., Kingston, R. E., Moore, D. D., Seidman, J. G., Smith, J. A., and Struhl, K. (eds.). 1987. *Current Protocols in Molecular Biology*, John Wiley & Sons, New York.

[3] Berger, S. L., and Kimmel, A. R. (eds.). 1987. *Guide to Molecular Cloning Techniques*, Academic Press, San Diego.

[4] Kelly M. L., Woodbury D. J. Ion channels from synaptic vesicle membrane fragments reconstituted into lipid bilayers, *Biophysical Journal* 70:2593-2599.

[5] Neher E., Sakmann B. 1976. Single channel currents recorded from membrane of denervated frog muscle fibers. *Nature* 260:799-802.

[6] Neher E., Sakmann B., Steinbach J. H. 1978. The Extracellular Patch Clamp: A method for resolving currents through individual open channels in biological membranes. *Pflugers Arch* 375:219-228.

[7] Hammill O. P., Marty A., Neher E., Sakmann B., and Sigworth F. J. 1981. Improved Patch-Clamp Techniques for High-Resolution Current Recording from Cells and Cell-Free Membrane Patches, *Pflugers Arch* 391:85-100.

[8] Sherman-Gold, Rivka (ed.). 1993. The Axon Guide for Electrophysiology & Biophysics.

[9] Rae, J., Cooper K., Gates P., Watsky, M. 1991. Low access resistance perforated patch recordings using amphotericin B, *Journal of Neuroscience Methods* 37:15-26.

[10] Sakmann B., Neher E. (eds.). 1995. Single-Channel Recording, $2^{nd}$ Edition, Plenum Press, NY.

We claim:

1. Electrophysiological measurement apparatus, comprising:
    a multi-well plate having a plurality of fluid chambers, each configured to support a biological material to be measured;
    a thin substrate having an array of apertures in alignment with the chambers of the multi-well plate, wherein the substrate is joined to the multi-well plate such that the chambers are open at the top and sealed at the bottom, except for the apertures, and wherein the diameter of the apertures is less than the diameter of the biological material, thereby enabling a high-resistance seal to be formed between the biological material in each chamber and a corresponding aperture;
    a fluid plenum to receive the multi-well plate such that one side of the substrate is immersed;
    a transfer device configured to move material into the fluid chambers of the multi-well plate while it is in contact with the fluid plenum:
    a first electrode disposed in the fluid plenum;
    at least one second electrode that can be selectively connected with and disconnected from the fluid chambers of the multi-well plate, wherein the second electrode disconnects from the fluid chambers when the transfer device moves material into the fluid chambers; and
    electrophysiological measurement circuitry in electrical communication with the electrodes;
    wherein the substrate is selected from the group consisting of polyethylene terephthalate (PET) and polyimide and further wherein the substrate has a glass coating at least in the region where the high-resistance seal is formed between the material and the substrate.

2. The apparatus of claim 1, wherein there is a single aperture associated with each chamber of the multi-well plate.

3. The apparatus of claim 1, wherein each fluid chamber contains a biological material to be measured.

4. The apparatus of claim 1, wherein the diameter of the apertures is in the range of about 1 to 10 micrometers.

5. The apparatus of claim 1, wherein the apertures are tapered.

6. The apparatus of claim 1, wherein the multi-well plate is sealed to the fluid plenum, enabling a differential pressure to be applied relative to the fluid in each chamber, thereby causing the material in each chamber to migrate to a respective aperture.

7. The apparatus of claim 1, wherein the multi-well plate is sealed to the fluid plenum, enabling a differential pressure to be maintained relative to the fluid in each chamber until between the material in each chamber forms the high-resistance seal to the corresponding aperture.

8. The apparatus of claim 1, wherein the fluid plenum includes a chemical reagent causing the material in each chamber to electrically permeabilize in the vicinity of the aperture.

9. The apparatus of claim 1, wherein a high voltage is temporarily applied across the electrodes to permeabilize the material in each chamber, at least in the vicinity of the apertures.

10. The apparatus of claim 1, further comprising a mechanism for moving the electrode into the chambers of the multi-well plate so as to automate the measurement of the material contained therein.

11. The apparatus of claim 1, wherein the at least one second electrode is moveable into and out of the top openings of the fluid chambers of the multi-well plate.

12. The apparatus of claim 1, further comprising a plurality of electrodes in alignment with a plurality of the chambers of the multi-well plate.

13. The apparatus of claim 12, further comprising a mechanism for moving the electrodes into the chambers of the multi-well plate to perform simultaneous measurements on the material contained therein.

14. The apparatus of claim 1, further comprising a system for transferring fluids from one or more sources to the chambers of the multi-well plate.

15. The apparatus of claim 1, wherein the second electrode is configured to move out from the fluid chambers to disconnect from the fluid chambers.

16. Electrophysiological measurement apparatus, comprising:
    a multi-well plate having a plurality of fluid chambers, each configured to support a biological material to be measured;
    a thin substrate having an array of apertures in alignment with the chambers of the multi-well plate, wherein the substrate is joined to the multi-well plate such that the chambers are open at the top and sealed at the bottom, except for the apertures, and wherein the diameter of the apertures is less than the diameter of the biological material, thereby enabling a high-resistance seal to be formed between the biological material in each chamber and a corresponding aperture;
    a fluid plenum to receive the multi-well plate such that one side of the substrate is immersed;
    a first electrode disposed in the fluid plenum;
    at least one second electrode that can be connected with and disconnected from the fluid chambers of the multi-well plate; and
    electrophysiological measurement circuitry in electrical communication with the electrodes,
    wherein the substrate is a plastic substrate having a glass coating at least in the region where the high-resistance seal is formed between the material and the substrate,
    wherein the substrate is selected from the group consisting of polyethylene terephthalate (PET) and polyimide.

17. The apparatus of claim 16, further comprising a fluidics system operative to control and regulate the differential pressure across the substrate to achieve a high-resistance electrical seal between the substrate and the biological material.

18. The apparatus of claim 17, wherein the fluidics system is further operative to remove trapped gas from both sides of the substrate to form a continuous fluid pathway for conducting electrical current.

19. The apparatus of claim 17, wherein the fluidics system is further operative to apply a vacuum so as to pneumatically isolate a region on one side of the substrate.

20. The apparatus of claim 16, further comprising reagent inputs for at least one of an extracellular saline solution, an intracellular saline solution, a wash solution, and a chemically altered intracellular saline solution used to achieve low resistance electrical access to the inside of a cell.

21. The apparatus of claim 20, wherein intracellular solutions are exchanged without introducing pressure changes that would disrupt the high-resistance electrical seal.

22. The apparatus of claim 16, further comprising a signal processor in communication with the electrodes, wherein the signal processor includes a multiplexer operative to route electrical signals derived from one or more of the electrodes on a selective basis.

23. The apparatus of claim 22, wherein the signal processor includes a low-noise, high-gain trans-impedance operational amplifier circuit and one or more isolated recording amplifier circuits.

24. The apparatus of claim 16, further comprising a moveable electronics head equipped with one or more sensing electrodes in communication with a signal processor, a moveable fluidics head equipped with one or more fluid-dispensing needles, the apparatus further including one or more positions for washing for the electronics head and/or the fluidics head.

25. The apparatus of claim 24, wherein each position for washing is automatically filled and drained via a peristaltic pump and vacuum-assisted waste line.

26. The apparatus of claim 24, wherein each position for washing is capable of washing an entire head or portions thereof to conserve conserving wash solution.

27. The apparatus of claim 24, further comprising one or more compound microplates, each having a standard well format accessible by the fluidics head.

28. The apparatus of claim 27, further comprising one or more saline solution reservoirs accessible by the fluidics head.

29. The apparatus of claim 24, further comprising a removable boat station for cell slurry addition accessible by the fluidics head.

30. The apparatus of claim 16, further comprising an electronics head using silver sensing electrodes, wherein the apparatus includes a station accessible by the electronics head used for depositing chloride on the electrodes.

31. The apparatus of claim 16, wherein there is a single aperture associated with each chamber of the multi-well plate.

32. The apparatus of claim 16, wherein each fluid chamber contains a biological material to be measured.

33. The apparatus of claim 16, wherein the substrate has a glass coating at least in the region where the high-resistance seal is formed between the material and the substrate.

34. The apparatus of claim 16, wherein the diameter of the apertures is in the range of about 1 to 10 micrometers.

35. The apparatus of claim 16, wherein the apertures are tapered.

36. The apparatus of claim 16, wherein the multi-well plate is sealed to the fluid plenum, enabling a differential pressure to be applied relative to the fluid in each chamber, thereby causing the material in each chamber to migrate to a respective aperture.

37. The apparatus of claim 16, wherein the multi-well plate is sealed to the fluid plenum, enabling a differential pressure to be maintained relative to the fluid in each chamber until between the material in each chamber forms the high-resistance seal to the corresponding aperture.

38. The apparatus of claim 16, wherein the fluid plenum includes a chemical reagent causing the material in each chamber to electrically permeabilize in the vicinity of the aperture.

39. The apparatus of claim 16, wherein a high voltage is temporarily applied across the electrodes to permeabilize the material in each chamber, at least in the vicinity of the apertures.

40. The apparatus of claim 16, further comprising a mechanism for moving the electrode into the chambers of the multi-well plate so as to automate the measurement of the material contained therein.

41. The apparatus of claim 16, wherein the at least one second electrode is moveable into and out of the top openings of the fluid chambers of the multi-well plate.

42. The apparatus of claim 16, further comprising a plurality of electrodes in alignment with a plurality of the chambers of the multi-well plate.

43. The apparatus of claim 42, further comprising a mechanism for moving the electrodes into the chambers of the multi-well plate to perform simultaneous measurements on the material contained therein.

44. The apparatus of claim 16, further comprising a system for transferring fluids from one or more sources to the chambers of the multi-well plate.

* * * * *